United States Patent [19]
Akimoto et al.

[11] Patent Number: 5,403,843
[45] Date of Patent: Apr. 4, 1995

[54] PYRROLOPYRIMIDINYLGLUTAMINATE DERIVATIVES AND THEIR USE

[75] Inventors: Hiroshi Akimoto, Kobe; Koichiro Ootsu, Mishima; Fumio Itoh, Toyonaka, all of Japan

[73] Assignee: Takeda Chemical Industries, Ltd., Osaka, Japan

[21] Appl. No.: 926,170

[22] Filed: Aug. 7, 1992

[30] Foreign Application Priority Data

Aug. 12, 1991 [JP] Japan ................. 3-202042
Mar. 27, 1992 [JP] Japan ................. 4-071513
Jun. 5, 1992 [JP] Japan ................. 4-145851

[51] Int. Cl.$^6$ ............. A61K 31/505; C07D 487/04
[52] U.S. Cl. ......................... 514/258; 514/183;
514/212; 514/252; 514/255; 540/452; 540/465;
540/481; 540/485; 540/486; 540/600; 544/116;
544/117; 544/238; 544/253; 544/280
[58] Field of Search ........... 514/183, 212, 252, 255,
514/258; 540/481, 452, 465, 485, 486, 600;
544/116, 117, 238, 253, 280

[56] References Cited

U.S. PATENT DOCUMENTS

| | | | |
|---|---|---|---|
| 4,767,761 | 8/1988 | Rosowsky | 514/249 |
| 4,895,946 | 1/1990 | Taylor et al. | 544/279 |
| 4,946,846 | 8/1990 | Nomura et al. | 514/258 |
| 4,996,206 | 2/1991 | Taylor et al. | 514/258 |
| 4,997,838 | 3/1991 | Akimoto et al. | 544/280 |

FOREIGN PATENT DOCUMENTS

| | | | |
|---|---|---|---|
| 0334636 | 7/1989 | European Pat. Off. | 544/280 |
| 0400562 | 12/1990 | European Pat. Off. | |
| 0402903 | 12/1990 | European Pat. Off. | |
| 0418924 | 3/1991 | European Pat. Off. | |
| 0431953 | 6/1991 | European Pat. Off. | |
| 0434426 | 6/1991 | European Pat. Off. | |
| 0438261 | 7/1991 | European Pat. Off. | |

Primary Examiner—Mukund J. Shah
Assistant Examiner—Y. N. Gupta
Attorney, Agent, or Firm—Foley & Lardner

[57] ABSTRACT

A condensed pyrimidine derivative of the formula (I):

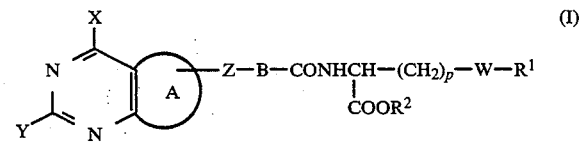

wherein the ring A stands for an optionally substituted 5-membered ring; B stands for an optionally substituted divalent 5- or 6-membered homo- or hetero-cyclic group; X stands for, among others, amino group; Y stands for, among others, hydrogen atom, halogen atom or amino group; Z stands for a divalent aliphatic group having five or less atoms forming straight chain, optionally having nitrogen, whose chain portion may optionally have a hetero-atom; W stands for, among others, —NH—CO— or —CO—NH—; $R^1$ stands for an optionally substituted cyclic or chain-like group; $COOR^2$ stands for an optionally esterified carboxyl group; and p denotes an integer of 1 to 4, provided that when —W—$R^1$ denotes a moiety represented by the formula:

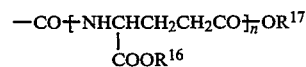

wherein $COOR^{16}$ and $COOR^{17}$ are, independently, an optionally esterified carboxyl group and n denotes an integer of 1 to 5, p denotes 1, 3 or 4, or a salt thereof, exhibiting highly specific toxicities to various tumor cells and excellent therapeutic effects on methotrexate-resistant tumor cells as well.

56 Claims, No Drawings

PYRROLOPYRIMIDINYLGLUTAMINATE DERIVATIVES AND THEIR USE

This invention relates to a novel condensed pyrimidine derivative useful as an anti-tumor agent, its production and use.

Folic acid and its related compounds are carriers of a C1 unit in a living body, derived from formic acid or formaldehyde, acting as a coenzyme in various enzymatic reactions such as those in biosynthesis of nucleic acid, in metabolism of amino acids and peptides and in generation of methane. Particularly for metabolism and transition reaction of C1 units in biosynthesis of nucleic acid, i.e. the purine synthetic pathway and the thymidine synthetic pathway, folic acid and its related compounds are essential. In order for folic acid to demonstrate its biological activities, normally, it is required to undergo two steps of reduction to be transformed into its active coenzyme form. As a drug substance which binds strongly to the enzyme (dihydrofolate reductase: DHFR) governing the second reduction step to thereby inhibit the reduction of dihydrofolate to tetrahydrofolate, there are known amethopterine (methotrexate: MTX) and its analogous compounds. These drugs, that act to exert damage to DNA synthesis, eventually bringing about cell death, have been developed as an antitumor agent and occupy a clinically important position as therapeutic agent of, mainly, leukemia. Furthermore, with remarkable developments of research work in the field of biochemistry, especially in the field of folic acid and relating compounds for the therapy of cancers, reports have been made of a novel DHFR inhibitor, namely a 10-deazaaminopterin-based antitumor agent (10-ethyl-10-deazaaminopterin: 10-EDAM) [NCI Monograph, 5, 127 (1987)] or an aminopteroyl type ornithine derivative, namely an N($\alpha$)-(4-amino-4-deoxypteroyl)-N($\delta$)-hemiphthaloyl-L-ornithine: PT523 [Japanese Publish unexamined Patent Application No. 502095/1990], and an U.S. Pat. No. 4,917,951 antagonism inhibiting agent aiming at an enzyme different from DHFR, namely a 5-deazatetrahydro folic acid-based antitumor agent, which can act principally through a mechanism to inhibit glycinamide-ribonucleotide transformylase, namely 5,10-dideaza-5,6,7,8-tetrahydro folic acid: DDATHF [Journal of Medicinal Chemistry, 28, 914 (1985)] or a quinazoline-based antitumor agent, which can work principally through a mechanism to inhibit thymidylate synthetase (2-desamino-2-methyl-10-propargyl-5,8-dideazafolate: DMPDDF) [British Journal of Cancer, 58, 241 (1988)]. All of these compounds are, however, within the category of heterocyclic compounds having a basic skeleton of a condensed ring of 6-membered rings (6—6 condensed ring). On the other hand, it was also reported that the folic acid antagonistic agents having the pyrrolo[2,3-d]pyrimidine ring as the basic skeleton which is a condensed ring from a 6-membered ring and a 5-membered ring has excellent antitumor activity, as well. However, there has been described that it is essential for the above-mentioned pyrrolo[2,3-d]pyrimidine derivatives to have glutamic acid mainly at the terminal side chain [U.S. Pat No. 4,997,838, EP-A-400,562, EP-A-402,903, EP-A-418,924, EP-A-431,953, EP-A-434,426, EP-A-438,261 and U.S. Pat. No. 4,996,206].

What is now specifically desired in the field of cancer therapy is the creation of drugs which have toxicities highly specific to cancer cells based on the action mechanism having excellent therapeutic effects. The MTX whose principal action mechanism consists in inhibition of dihydrofolate reductase is clinically used widely, though the therapeutic effect is still unsatisfactory because it has relatively strong toxicity with little effect on solid cancer. Further, acquired resistance against MTX has now been taken up as a great problem. As the resistance mechanism against MTX, there are counted, for example, rise of DHFR level, lowering of cell membrane capability of carrying drugs and lowering of the level of folylpolyglutamate synthetase (FPGS). By overcoming at least one of these resistance factors, development of drugs showing excellent therapeutic effect against MTX-resistant cancers has been expected.

This invention provides a novel condensed heterocyclic compounds which have not only 6-5 condensed ring as the basic skeleton but also, at the terminal side-chain, no two coexisting carboxyl groups derived form glutamic acid inhibit not less than one of the enzymatic reactions involving folic acid, exhibit highly selective toxicity against various tumors (especially human lung cancer cells) and also produce excellent antitumor effect which also overcome MTX-resistance.

This inventors of present invention explored compounds which could be of use as medicament for inhibiting tumor and particularly compounds of value for inhibiting cell-proliferation and succeeded in the creation of a condensed pyrimidine derivative of the formula (I):

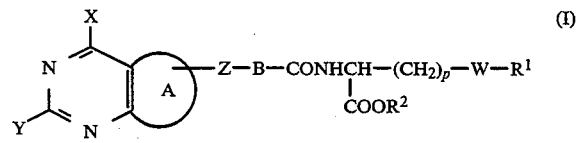

wherein the ring A stands for an optionally hydrogenated 5-membered ring optionally having substituents; B stands for an optionally substituted divalent 5- or 6-membered homo- or hetero-cyclic group; X stands for an amino group, hydroxyl group or mercapto group; Y stands for hydrogen atom, halogen atom or a group bonded through carbon, nitrogen, oxygen or sulfur atom; Z stands for an optionally substituted divalent aliphatic group having five or less atoms constituting the straight-chain optionally including one hetero-atom; W stands for a group represented by

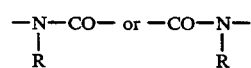

(wherein R stands for a hydrogen atom or an optionally substituted $C_{1-4}$ hydrocarbon group or may form a 3- to 13-membered ring with $R_1$, taken together with adjacent

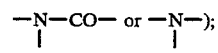

$R^1$ stands for an optionally substituted cyclic or chain-like group; $COOR^2$ stands for an optionally esterified carboxyl group; and p denotes an integer of 1 to 4 provided that when —W—$R^1$ denotes a moiety represented by the formula:

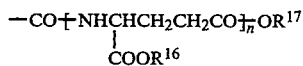

wherein $COOR^{16}$ and $COOR^{17}$ are, independently, an optionally esterified carboxyl group and n denotes an integer of 1 to 5, p denotes 1, 3 or 4, or its salt.

In the above formulae, the compounds of this invention can exist as an equilibrium mixture with their tautomeric isomers. Illustrated below are the partial structural formulae capable of undergoing tautomerism, with the equilibria among them being shown as well.

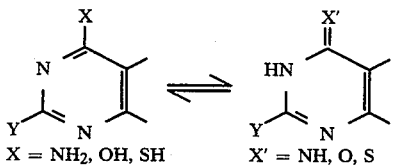

Throughout this specification, for the purpose of convenience of expression, the amino, hydroxyl and mercapto forms are to be described, with the corresponding designations being adopted, and in either case, their tautomers or the imino, oxo and thioxo forms are understood to be included in the scope of this invention.

And, in the compounds of this invention, the presence of a plural number of asymmetric centers is possible, but except that the absolute configuration of the partial structural formula:

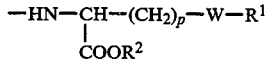

is S(L), the absolute configurations of other asymmetric centers may be either of S, R or a mixture of RS. In such a case, a plurality of diastereomers exist, and they can be easily separated by conventional purification means, if necessary.

All the above-described diastereomers that can be separated by such procedures are included in the scope of this invention.

Referring to the above formulae, the 5-membered rings of optionally hydrogenated 5-membered rings shown by the ring A include, for example, 5-membered rings being composed of carbon atoms alone or both carbon atoms and one hetero atom (for example, optionally oxidized nitrogen atom, oxygen atom or optionally oxidized sulfur atom). Examples of such optionally hydrogenated 5-membered rings include a cyclopentadiene, cyclopentene, furan, dihydrofuran, thiophene, dihydrothiophene, thiophen-1-oxide, dihydrothiophen-1-oxide, thiophene-1,1-dioxide, dihydrothiophene-1,1-dioxide, pyrrole, pyrroline and so on. The more preferable examples include a pyrrole, furan, thiophene and so on. These 5-membered rings may have one or two substituents at their replaceable, and examples of such substituents include $C_{1-4}$ alkyl group (e.g. methyl, ethyl, propyl, iso-propyl group), $C_{2-4}$ alkenyl group (e.g. vinyl, 1-methylvinyl, 1-propenyl, aryl, allenyl group), $C_{2-4}$ alkynyl group (e.g. ethynyl, 1-propynyl, propargyl group), $C_{3-8}$ cycloalkyl group (e.g. cyclopropyl group), halogen atom (e.g. fluorine, chlorine, bromine, iodine), $C_{1-4}$ alkanoyl group (e.g. formyl, acetyl, propionyl, butyryl, isobutyryl group), benzoyl group, substituted benzoyl group (e.g. halogenobenzoyl group such as p-chlorobenzoyl, p-methoxybenzoyl or 3,4,5-trimethoxybenzoyl group, or mono-, di- or tri-$C_{1-4}$ alkoxy benzoyl), cyano group, carboxyl group, carbamoyl group, nitro group, hydroxyl group, hydroxy-$C_{1-4}$ alkyl group (e.g. methoxymethyl group, ethoxymethyl group, methoxyethyl group, ethoxyethyl group), $C_{1-4}$ alkoxy-$C_{1-4}$ alkyl (e.g. methoxymethyl, ethoxymethyl, methoxyethyl, ethoxyethyl) $C_{1-4}$ alkoxy group (e.g. methoxy, ethoxy, propoxy group), mercapto group, $C_{1-4}$ alkylthio group (e.g. methylthio, ethylthio, propylthio group), amino group, mono- or di-$C_{1-4}$ alkylamino group (e.g. methylamino, ethylamino, dimethylamino, diethylamino groups), $C_{1-4}$ alkanoylamino group (e.g. formamide, acetamide group) and so on. In the case where the ring A is pyrrole or pyrroline ring, as substituent(s) optionally substituted at N-position, use is made of, besides the above-mentioned $C_{1-4}$ alkyl group, $C_{2-4}$ alkenyl group, $C_{2-4}$ alkenyl group, $C_{3-6}$ cycloalkyl group, $C_{1-4}$ alkanoyl group, benzoyl group, substituted benzoyl group, hydroxy $C_{1-4}$ alkyl group, $C_{1-4}$ alkoxy-$C_{1-4}$ alkyl group (especially methoxyethyl group, ethoxyethyl group), phenyl group, substituted phenyl groups (e.g. halogenophenyl such as p-chlorophenyl, p-methoxyphenyl, 3,4,5-trimethoxyphenyl, or mono-, di- or tri- $C_{1-4}$ alkoxyphenyl), benzyl group, substituted benzyl group (e.g. halogenobenzyl such as p-chlorobenzyl, $C_{1-4}$ alkoxy benzyl such as p-methoxybenzyl, diphenylmethyl group) and so on.

The bonding between the ring A and Z may take place at any feasible positions, and, in the case where the ring A is pyrrole or pyrroline ring, the bonding may take place at N-position.

B stands for an optionally substituted divalent 5- or 6-membered homocyclic or heterocyclic group. As the homocyclic groups represented by B, use is made of, for example, a divalent 5- or 6-membered hydrocarbon group. As such hydrocarbon group, use is often made of a 5- or 6-membered aliphatic hydrocarbon group (e.g. cyclopentylene, cyclohexylene, 1,3- or 3,5-cyclopentadien-1,3-ylene, cyclopenten-(1,3-, 1,4- or 3,5-)ylene, cyclopentan-1,3-ylene, phenyl-(1,3- or 1,4-)ylene, cyclohexan-(1,3- or 1,4-)ylene, cyclohexen-(1,3-, 1,4-, 1,4-, 3,5- or 3,6-)ylene, 1,3-cyclohexadien-(1,3-, 1,4-, 1,5-, 2,4-, 2,5- or 2,6-)ylene, 1,4-cyclohexadien-(1,3-, 1,4- or 1,5-)ylene,) or phenylene (1,2-phenylene, 1,3-phenylene, 1,4-phenylene), especially 1,4-phenylene. As the heterocyclic groups represented by B, use is made of a divalent 5- or 6-membered heterocyclic group containing one to three hetero-atoms (e.g. N, O, S), having bonding hands at positions which are not adjacent to each other in the ring. As the said 5-membered heterocyclic group represented by B, use is made of, for example, thiophen-(2,4-, 2,5- or 3,4-)ylene, furan-(2,4-, 2,5- or 3,4-)ylene, pyrrole-(1,3-, 2,4-, 2,5- or 3,4-)ylene, thiazol-(2,4- or 2,5-)ylene, imidazole-(1,4-, 2,4- or 2,5-)ylene, thiadiazol-2,5-ylene, their partially reduced forms (multiple bond being partially reduced) or completely reduced forms (multiple bond being completely reduced). Examples of the said 6-membered heterocyclic ring include, pyridin-(2,4-, 2,5-, 2,6- or 3,5-)ylene, pyran-(2,4-, 2,5-, 2,6-, 3,5-, 3,6- or 4,6-)ylene, pyrazin-(2,5- or 2,6-)ylene, pyrimidin-(2,4- or 2,5-)ylene, pyridazin-3,5-ylene, or their partially reduced forms or completely reduced forms. As especially preferable examples of B include a phenyl-1,4-ylene, thiophen-2,5-ylene, thiazol-2,5-ylene, pyridin-2,5-ylene and so on. The divalent 5- or 6-membered homo or heterocyclic group represented by B may have one or two substituents at its replaceable positions. Examples of the said substituents include a $C_{1-4}$ alkyl group (e.g. methyl, ethyl, propyl, iso-propyl group), $C_{2-4}$ alkenyl group (e.g. vinyl, 1-methylvinyl, 1-propenyl, aryl, allenyl group), $C_{2-4}$ alkinyl group (e.g. ethynyl, 1-propynyl, propargyl group), $C_{3-8}$ cycloalkyl group (e.g. cyclopropyl group), halogen atom (e.g. chlorine, bromine, fluorine, iodine) hydroxyl group, $C_{1-4}$ alkoxy group (e.g. methoxy group), di-$C_{1-4}$ alkylamino group (e.g. dimethylamino group), halogeno-$C_{1-4}$ alkyl group (e.g. trifluoromethyl group), oxo group, $C_{1-4}$ acyl group (e.g. formyl group), and $C_{1-4}$ alkoxy-$C_{1-4}$ alkyl group (e.g. methoxymethyl, 2-ethoxyethyl group). The more preferable examples of the said substituents include halogen atom (e.g. chlorine, bromine, fluorine, iodine) and so on.

X stands for an amino, hydroxy or mercapto group. More preferable examples of X include an amino or hydroxy group.

Y stands for a hydrogen atom, halogen atom or group bonded through carbon, nitrogen or sulfur atom.

The halogen atom represented by Y includes fluorine, chlorine, bromine or iodine.

The group represented by Y, which is bonded through carbon, nitrogen or sulfur atom, may be a cyano, carboxyl, carbamoyl, amino, nitro, hydroxyl, mercapto or lower hydrocarbon group, such as a $C_{1-4}$ alkyl group (e.g. methyl, ethyl propyl, iso-propyl group), $C_{2-4}$ alkenyl group (e.g. vinyl, 1-methylvinyl, 1-propenyl, aryl, allenyl group), $C_{2-4}$ alkynyl group (ethynyl, 1-propynyl, propargyl group), $C_{3-8}$ cycloalkyl group (e.g. cyclopropyl group) and so on, $C_{6-10}$ aryl group (e.g. phenyl group, naphthyl group), 5- or 6-membered heterocyclic group containing one to four of heteroatoms such as N, S, O (e.g. pyrrolyl, imidazolyl, pyrazolyl, thenyl, furyl, thiazolyl, thiadiazolyl, oxazolyl, oxadiazolyl, pyridyl, pyranyl, pyrazinyl, pyrimidinyl, pyridazinyl, their partially reduced forms or completely reduced forms, dioxolanyl, piperidino, morpholino, N-methylpiperazinyl, N-ethylpiperazinyl, dioxanyl) and so on. In cases where Y is a lower hydrocarbon group, aryl group or 5- or 6-membered heterocyclic group, Y may have one or two substituents. Examples of such substituents include a $C_{1-4}$ alkyl group (e.g. methyl, ethyl, propyl, iso-propyl group), a $C_{2-4}$ alkenyl group (e.g. vinyl, 1-methylvinyl, 1-propenyl, aryl, allenyl group), a $C_{2-4}$ alkynyl group (e.g. ethynyl, 1-propynyl, propargyl group) or $C_{3-8}$ (e.g. cyclopropyl group), and, besides, halogen atom (e.g. fluorine), hydroxyl, oxo, a $C_{1-4}$ alkoxy group (e.g. methoxy group), di-$C_{1-4}$ alkyl group (e.g. trifluoromethyl group), a $C_{1-4}$ acyl group (e.g. formyl group), hydroxy-$C_{1-4}$ alkyl group (e.g. hydroxymethyl, 2-hydroxyethyl group), $C_{1-4}$ alkoxy-$C_{1-4}$ alkyl group (e.g. methoxymethyl, 2-ethoxyethyl group) and so on.

The group represented by Y, which is bonded through carbon, nitrogen, oxygen or sulfur atom, may be also (1) an alkoxy group, alkylthio group, alkylcarbonylamino group or alkylcarbonyloxy group, and group specifically described referring to the above-mentioned lower hydrocarbon group is used as the alkyl moiety of these groups, (2) aryloxy group, arylthio group, aroylamino group or aroyloxy group, and phenyl group, naphthyl group or the like is used as the alkyl moiety of these groups, (3) heterocyclic oxy group, heterocyclic thio group, heterocyclic carbonylamino group or heterocyclic carbonyloxy group, and the group shown by the above-mentioned 5- or 6-membered heterocyclic group represented by Y is used as the heterocyclic moiety of these groups or (4) a substituted amino group such as a mono-substituted or di-substituted amino group, and the above-mentioned lower hydrocarbon group, aryl group and 5- or 6-membered heterocyclic group represented by Y are used as the substituted moiety.

The more preferable examples of Y include an amino group and so on.

Z stands for an optionally substituted divalent straight-chained aliphatic group having 5 or less chain-composing atoms, which is optionally bonded through one hetero-atom (nitrogen atom, oxygen atom, sulfur atom or the like) at the site of chain. Examples of the divalent straight-chained aliphatic group having 5 or less chain-composing atoms include a $C_{1-5}$ alkylene group such as methylene, ethylene, trimethylene, tetramethylene, pentamethylene groups and so on, $C_{2-5}$ alkenylene group such as vinylene, propenylene, 1- or 2-butenylene, butadienylene, 1- or 2-pentenylene, and 1,3- or 1,4-pentadienylene groups, $C_{2-5}$ alkynylene group such as ethynylene, 1- or 2-propynylene, 1- or 2-butynylene, 1-, 2- or 3-pentynylene groups and so on.

And, as the optionally substituted divalent straight-chained aliphatic group having 5 or less chain-composing atoms, which is optionally bonded through one hetero atom at the site of chain, use is made of a group represented by the formula —$Z^1$—$Z^2$—$Z^3$— wherein $Z^1$ and $Z^3$ independently stand for a bond or an optionally substituted divalent $C_{1-4}$ lower hydrocarbon group (provided that the total number of carbon atoms in $Z^1$ and $Z^3$ is one to four), and $Z^2$ stands for —O—, the formula —S(O)n$^1$— (wherein n$^1$ denotes an integer of 0 to 2) or the formula

($R^4$ stands for a hydrogen atom, an optionally substituted lower hydrocarbon group or a $C_{1-4}$ alkoxycarbonyl group). Examples of the divalent lower hydrocarbon group in the optionally substituted divalent lower hydrocarbon groups represented by $Z^1$ and $Z^3$ include a $C_{1-4}$ alkylene groups such as methylene, ethylene, trimethylene, tetramethylene and so on, $C_{2-4}$ alkenylene group such as vinylene, propenylene, 1- or 2-butenylene, butadienylene and so on, $C_{2-4}$ alkynylene group such as ethynylene, 1- or 2-propynylene, 1- or 2-butynylene and so on, and so on. As the lower hydrocarbon group of the optionally substituted lower hydrocarbon group represented by $R^4$, use is made of $C_{1-4}$ alkyl group (e.g. methyl, ethyl, propyl, iso-propyl group), $C_{2-4}$ alkenyl group (e.g. vinyl, 1-methylvinyl, 1-propenyl, aryl, allenyl groups), $C_{2-4}$ alkynyl group (e.g. ethynyl, 1-propynyl, propargyl groups), $C_{3-8}$ cycloalkyl group (e.g. cyclopropyl group) and so on. The divalent aliphatic group having straight chained 5 or less chain-composing atoms represented by Z, the divalent lower hydrocarbon groups represented by Z1 and Z3 and the lower hydrocarbon group represented by R4 may have 1 to 2 substituents. Examples of such substituents include, besides a $C_{1-4}$ alkyl group (e.g. methyl, ethyl, propyl, iso-propyl groups), $C_{2-4}$ alkenyl groups (e.g. vinyl, 1-methylvinyl, 1-propenyl, aryl, allenyl groups), $C_{2-4}$ alkynyl group (e.g. ethynyl, 1-propynyl, propargyl groups), $C_{3-8}$ cycloalkyl group (e.g. cyclopropyl group) or like this, halogen atom (e.g. fluorine), hydroxyl group, oxo group, $C_{1-4}$ alkoxy group (e.g. methoxy group), di-$C_{1-4}$ alkylamino group (e.g. dimethylamino, diethylamino group), halogeno-$C_{1-4}$ alkyl group (e.g. trifluoromethyl group), $C_{1-4}$ acyl group (e.g. formyl group), hydroxy-$C_{1-4}$ alkyl group (e.g. hydroxymethyl, 2-hydroxyethyl group), $C_{1-4}$ alkoxy-$C_{1-4}$ alkyl group (e.g. methoxymethyl, 2-ethoxyethyl groups), $C_{1-4}$ alkoxy-carbonyl (e.g. methoxycarbonyl, ethoxycarbonyl, n-propoxycarbonyl, n-butyoxycarbonyl, tert-butoxycarbonyl) and so on.

The $C_{1-4}$ alkoxy-carbonyl represented by $R^4$ include a methoxycarbonyl, ethoxycarbonyl, n-propoxycarbonyl, n-butoxycarbonyl, tert-butoxycarbonyl and so on.

As Z, use is made of, for example $C_{1-5}$ alkylene (e.g. methylene, ethylene, trimethylene) or a group represented by the formula

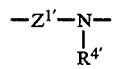

($Z^{1'}$ stands for a $C_{1-4}$ alkylene group, and $R^{4'}$ stands for a hydrogen atom, a $C_{1-4}$ alkyl group which may be substituted by a $C_{1-4}$ alkoxy-carbonyl group, formyl group or a $C_{1-4}$ alkoxy-carbonyl group.). As the $C_{1-4}$ alkylene represented by $Z^{1'}$, use is made of, for example methylene, ethylene, trimethylene, tetraethylene and so on, more especially ethylene, trimethylene. As the $C_{1-4}$ alkyl of the $C_{1-4}$ alkyl group which may be substituted by a $C_{1-4}$ alkoxycarbonyl group, use is made of, for example, methyl, ethyl, n-propyl, n-butyl and so on. As the $C_{1-4}$ alkoxy-carbonyl, use is made of, for example, methoxycarbonyl, ethoxycarbonyl, n-propoxycarbonyl, n-butoxycarbonyl, tert-butoxycarbonyl and so on. As $R^{4'}$, use is made of, for example, methyl or tert-butoxycarbonyl.

W represents

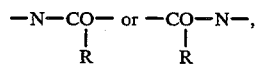

wherein R stands for a hydrogen atom or optionally substituted $C_{1-4}$ hydrocarbon group, or may form a 5- to 13-membered cyclic group, taken together with

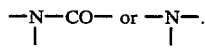

As the $C_{1-4}$ hydrocarbon group in the optionally substituted $C_{1-4}$ hydrocarbon group represented by R, use is made of $C_{1-4}$ alkyl group (e.g. methyl, ethyl, propyl, isopropyl, butyl, isobutyl, sec-butyl and tert-butyl group), $C_{2-4}$ alkenyl group (e.g. vinyl, allyl, 1-methylvinyl and 2-methylvinyl group) and $C_{3-4}$ cycloalkyl group (e.g. cyclopropyl and cyclobutyl group). Examples of such substituents include, besides $C_{1-4}$ alkyl group (e.g. methyl, ethyl, propyl and iso-propyl group), $C_{2-4}$ alkenyl group (e.g. vinyl, 1-methylvinyl, 1-propenyl, aryl and allenyl group), $C_{2-4}$ alkynyl group (e.g. ethynyl, 1-propynyl and propargyl group) or $C_{3-8}$ cycloalkyl group (e.g. cyclopropyl group), halogen atoms (e.g. fluorine, chlorine, bromine, fluorine, iodine), hydroxyl group, oxo group, $C_{1-4}$ alkoxy group (e.g. methoxy group), di-$C_{1-4}$ alkylamino group (e.g. dimethylamino and diethylamino group), halogeno-$C_{1-4}$ alkyl group (e.g. trifluoromethyl group), $C_{1-4}$ acyl group (e.g. formyl group), hydroxy-$C_{1-4}$ alkyl group (e.g. hydroxymethyl, 2-hydroxyethyl group) and $C_{1-4}$ alkoxy-$C_{1-4}$ alkyl group (e.g. methoxymethyl, 2-ethoxyethyl group). The number of these substituents is preferable one to three.

Examples of the 5- to 13-membered heterocyclic group optionally formed by R1 and the adjacent

group or

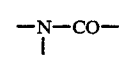

group include the 5 to 13-membered heterocyclic group being composed of carbon atoms and one to four hetero atoms selected from the group consisting of a nitrogen, oxygen, sulfur atom and so on. The examples of the 13-membered heterocyclic group include pyrrolyl, imidazolyl, pyrazolyl, piperidino, morpholino, dihydropyridyl, tetrahydropyridyl, N-$C_{1-4}$ alkylpiperazinyl (e.g. N-methyl piperazinyl, N-methyl piperazinyl group), azacycloheptyl, azacyclooctyl, isoindolyl, indolyl or their partially reduced or completely reduced group, 2-pyrrolidinon-1-yl, 2-piperazinon-1-yl, hexahydro-2-azepinon-1-yl, octahydro-2-azocinon-1-yl, 2-oxoindolin-1-yl, 1-oxoisoindolin-2-yl, 2-oxo-1,2,3,4-tetrahydroquinolin-1-yl, 1-oxo-1,2,3,4-tetrahydroisoquinolin-2-yl, 1-oxo-5H-benzo-1,2,3,4-tetrahydro-2-azepin-2-yl, 1-oxobenzo-1,2,3,4,5,6-hexahydro-2-azocin-2-yl, 2-oxo-5H-benzo-1,2,3,4-tetrahydro-1-azepin-1-yl, 2-oxobenzo-1,2,3,4,5,6-hexahydro-1-azocin-1-yl, succinimide, glutarimide, 1,4-butanedicarboximide, 1,5-pentanedicarboximide, 1,2-cyclohexanedicarboximide, phthalimide or their partially reduced or completely reduced group. These group may optionally be further cyclized with $C_{6-10}$ aromatic hydrocarbon (e.g. phenyl such as benzene ring, naphthalene ring or their partially reduced or completely reduced ring) or 5- or 6-membered heterocyclic ring (thiophene, furan, pyrrol, imidazole, pyrazole, thiazole, isothiazole, thiadiazole, oxazole, isoxazole, oxadiazole, furazane, pyran, pyridine, pyrazine, pyrimidine, pyridazine or their partially reduced or completely reduced compounds, dioxolan, dioxane, piperidine, morpholine, N-methylpiperazine and N-ethylpiperazine).

The 5- to 13-membered cyclic group formed by R, $R^1$ and the adjacent

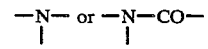

group may optionally have one or two substituents. Examples of such substituents include, besides $C_{1-4}$ alkyl group (e.g. methyl, ethyl, propyl and iso-propyl group), $C_{2-4}$ alkenyl group (e.g. vinyl, 1-methylvinyl, 1-propenyl, aryl and allenyl group), $C_{2-4}$ alkynyl group (e.g. ethynyl, 1-propynyl and propargyl group) or $C_{3-8}$ cycloalkyl group (e.g. cyclopropyl group), halogen atoms (e.g. fluorine, chlorine, bromine, iodine), hydroxyl group, oxo group, $C_{1-4}$ alkoxy group (e.g. methoxy group), di-$C_{1-4}$ alkylamino group (e.g. dimethylamino and diethylamino group), halogeno-$C_{1-4}$ alkyl group (e.g. trifluoromethyl group), $C_{1-4}$ acyl group (e.g. formyl group), hydroxy-$C_{1-4}$ alkyl group (e.g. hydroxymethyl, 2-hydroxyethyl group) and $C_{1-4}$ alkoxy-$C_{1-4}$ alkyl group (e.g. methoxymethyl, 2-ethoxyethyl group).

As R, use is made of, for example hydrogen atom and so on.

Examples of the cyclic group of the optionally substituted cyclic group represented by $R^1$ include 5- or 6-membered cyclic hydrocarbon group or 5- or 6-membered heterocyclic groups being composed of carbon atoms and one to four hetero-atoms selected from the group consisting of a nitrogen, oxygen and sulfur atom in the ring, or their condensed cyclic group. Examples of the 5-membered cyclic group represented by $R^1$ include cyclopentadienyl, cyclopentenyl, cyclopentyl, thienyl, furyl, pyrrolyl, thiazolyl, imidazolyl, thiadiazolyl, tetrazolyl or their partially reduced or completely reduced compounds; examples of the 6-membered cyclic group include phenyl, cyclohexyl, cyclohexenyl, cyclohexanedienyl, pyridyl, pyranyl, pyrazinyl, pyrimidinyl, pyridazinyl or their partially reduced or completely reduced compounds; and examples of the condensed cyclic group of the 5- or 6-membered cyclic hydrocarbon or heterocyclic group include naphthyl, indenyl, benzothiazolyl, benzooxazolyl, quinolyl, isoquinolyl, quinazolyl or their partially reduced or completely reduced compounds. Especially, as the cyclic groups represented by $R^1$ phenyl, cyclohexyl, naphthyl, thienyl, cyclopentyl, tetrazolyl or the like are preferable.

The preferable examples of chain group of the optionally substituted chain group represented by $R^1$ are $C_{1-4}$ lower chain-like hydrocarbon group, as exemplified by $C_{1-4}$ alkyl group such as methyl, ethyl, propyl, isopropyl, butyl, isobutyl, sec-butyl and tert-butyl group, $C_{2-4}$ alkenyl group such as vinyl, allyl, 1-methylvinyl and 2-methylvinyl group, and $C_{3-4}$ cycloalkyl group such as cyclopropyl and cyclobutyl group. The cyclic or chainlike group represented by $R^1$ may optionally have one or two substituents. Examples of such substituents include $C_{1-4}$ alkyl group (e.g. methyl, ethyl, propyl, isopropyl, butyl, isobutyl, sec-butyl and tert-butyl group), $C_{2-4}$ alkenyl group (e.g. vinyl, 1-methylvinyl, 1-propenyl, aryl and allenyl group), $C_{2-4}$ alkynyl group (e.g. ethynyl, 1-propynyl and propargyl group), $C_{3-6}$ cycloalkyl group (e.g. cyclopropyl, cyclobutyl, cyclopentyl and cyclohexyl group), $C_{5-6}$ cycloalkenyl group (e.g. cyclopentenyl and cyclohexenyl group), $C_{7-8}$ aralkyl group (e.g. benzyl, alpha-methylbenzyl and phenetyl group), phenyl group, optionally substituted 5- or 6-membered heterocyclic ring (e.g. tetrazolyl, triazolyl, imidazolyl, oxazolyl, furanyl, thiazolyl, pyridyl, pirazyl triazyl), $C_{1-4}$ alkoxy group (e.g. methoxy, ethoxy, propoxy, iso-propoxy, n-butoxy, iso-butoxy, sec-butoxy and tert-butoxy group), phenoxy group, $C_{1-4}$ alkanoyl group (e.g. formyl, acetyl, propionyl, n-butyryl and iso-butyryl group), benzoyl group, $C_{1-4}$ alkanoyloxy group (e.g. formyloxy, acetyloxy, ethyryloxy propionyloxy, n-butyryloxy and iso-butyryloxy group), benzoyloxy group, carboxyl group, $C_{1-4}$ alkoxy-carbonyl group (e.g. methoxycarbonyl, ethoxycarbonyl, n-propoxycarbonyl, iso-propoxycarbonyl, n-butoxycarbonyl, isobutoxycarbonyl and tert-butoxycarbonyl group), $C_{1-4}$ alkoxy-carbonyl-$C_{1-4}$ alkyl (e.g. methoxycarbonylmethyl, ethoxycarbonylmethyl, carboxyl-$C_{1-4}$ alkyl (e.g. carboxylmethyl, carboxylethyl), carbamoyl group, N-substituted carbamoyl group (e.g. N-$C_{1-4}$ alkyl carbamoyl group such as N-methylcarbamoyl, N-ethylcarbamoyl, N-propylcarbamoyl, N-isopropylcarbamoyl and N-butylcarbamoyl), N,N-disubstituted carbamoyl group (e.g. 1-aziridinylcarbonyl, 1-azetidinylcarbonyl, 1-pyrrolidinylcarbonyl, 1-piperidinylcarbonyl, N-methylpiperazinylcarbonyl and morpholinocarbonyl group, besides N,N-dimethylcarbamoyl, N,N-diethylcarbamoyl, N,N-dipropylcarbamoyl and N,N-dibutylcarbamoyl), halogen atoms (e.g. fluorine, chlorine, bromine and iodine), mono-, di- or tri-halogeno-$C_{1-4}$ alkyl group (e.g. trifluoromethyl group) oxo group, amidino group, imino group, amino group, mono-substituted amino group (e.g. mono-$C_{1-4}$ alkylamino group such as methylamino, ethylamino, propylamino, isopropylamino and butyl amino), di-substituted amino group (e.g. di-$C_{1-4}$ alkylamino group such as dimethylamino, diethylamino, dipropylamino, diisopropylamino and dibutylamino), 3- to 6-membered cyclic amino group (e.g. aziridinyl, azetidinyl, pyrrolidinyl, pyrrolynyl, pyrrolyl, imidazolyl, pyrazolyl, imidazolidinyl, piperidino, morpholino, dihydropyridyl, pyridyl, N-methylpiperazinyl and N-ethylpiperazinyl group) alkanoylamido group (e.g. $C_{1-4}$ alkanoylamido group such as formamide, acetamide, trifluoroacetamido, propionylamido, butyrylamido and isobutyrylamido), benzamido group, carbamoylamino group, N-substituted carbamoylamino group (e.g. N-$C_{1-4}$ alkyl carbamoylamino group such as N-methylcarbamoylamino, N-ethylcarbamoylamino, N-propylcarbamoylamino, N-isopropylcarbamoylamino and N-butylcarbamoylamino), N,N-disubstituted carbamoylamino group (e.g. 1-aziridinylcarbonylamino, 1-azetidinylcarbonylamino, 1-pyrrolidinylcarbonylamino, 1-piperidinylcarbonylamino, N-methylpiperazinylcarbonylamino and morpholinocarbonylamino group, besides N,N-dimethylcarbamoylamino, N,N-diethylcarbamoylamino, N,N-dipropylcarbamoylamino and N,N-dibutylcarbamoylamino), $C_{1-3}$ alkylene dioxy (e.g. methylene dioxy, ethylene dioxy), —B(OH)$_2$, hydroxyl group, epoxy group (—O—), nitro group, cyano group, mercapto group, sulfo group, sulfino group, phosphono group, dihydroxyboryl group, sulfamoyl group, N-substituted sulfamoyl group (e.g. $C_{1-4}$ alkyl sulfamoyl group such as N-methylsulfamoyl, N-ethylsulfamoyl, N-propylsulfamoyl, N-isopropylsulfamoyl and N-butylsulfamoyl), N,N-disubstituted sulfamoyl group (e.g. 1-pyrrolidinylsulfonyl, 1-piperidinylsulfonyl, N-methyl-1-piperazinylsulfonyl and morpholinosulfonyl group, besides di-$C_{1-4}$ alkyl sulfamoyl group such as N,N-dimethylsulfamoyl, N,N-diethylsulfamoyl, N,N-dipropylsulfamoyl and N,N-dibutylsulfamoyl), $C_{1-4}$ alkylthio group (e.g. methylthio, ethylthio, propylthio, isopropylthio, n-butylthio, sec-butylthio and tert-butylthio group), phenylthio group, $C_{1-4}$ alkyl sulfinyl group (e.g. methylsulfinyl, ethylsulfinyl, propylsulfinyl and butylsulfinyl group), phenylsulfinyl group, $C_{1-4}$ alkyl sulfonyl group (e.g. methylsulfonyl, ethylsulfonyl, propylsulfonyl and butylsulfonyl group) and phenylsulfonyl group, especially preferable ones being hydroxy group, carboxyl group, sulfo group; phosphono group, dihydroxyboryl group or the like. Among these substituents, those which are capable of being further substituted may have further one or two substituents, as exemplified by $C_{1-4}$ alkyl group (e.g. methyl, ethyl, propyl, isopropyl, butyl, isobutyl, sec-butyl, tert-butyl group), $C_{1-4}$ alkoxy group (e.g. methoxy group and ethoxy group), halogen atoms (e.g. fluorine, chlorine, bromine and iodine) and water-soluble group (e.g. hydroxyl group, carboxyl group, sulfo group, phosphono group, amidino group, amino group, methylamino group, ethylamino group, dimethylamino group, diethylamino group, morpholino group, piperidyl group, N-methylpiperazyl group, pyridyl group, trimethylammonium group, triethylammonium group, pyridinium group tetrazolyl group, carboxylmethyl group and so on.) Especially, the carboxyl group may be esterified by a $C_{1-4}$ alkyl group.

As $R^1$, use is made of, for example, a $C_{1-4}$ alkyl, $C_{2-4}$ alkenyl, $C_{2-4}$ alkynyl, phenyl, naphthyl and tetrazolyl which may be substituted by the substituent(s) selected from the group consisting of a hydroxy group, carboxyl group, $-B(OH)_2$, tetrazolyl, methylene dioxy, $C_{1-4}$ alkyl (e.g. methyl), $C_{1-4}$ alkoxy (e.g. methoxy), carboxy-$C_{1-4}$ alkyl (e.g. carboxymethyl), $C_{1-4}$ alkoxy-carbonyl-$C_{1-4}$ alkyl (e.g. methoxycarbonylmethyl, ethoxycarbonylmethyl), $C_{1-4}$ alkanoylamide (e.g. formamide, acetamide), 1-pyrolidynylcarbonyl group.

$COOR^2$ stands for an optionally esterified carboxy group. The $COOR^2$ includes one which may be used as intermediate for synthesis, pharmaceutically acceptable one, one which can change to be pharmaceutically acceptable only in body, and so on.

As the optionally esterified carboxyl group represented by $COOR^2$, use is especially made of carboxyl group optionally esterified with, for example, a $C_{1-5}$ alkyl group, an optionally substituted benzyl group or an optionally substituted phenyl group. Examples of the lower alkyl group include methyl, ethyl, propyl, isopropyl, n-butyl, iso-butyl, tert-butyl, n-pentyl, iso-pentyl, sec-pentyl, neo-pentyl and tert-pentyl; examples of the optionally substituted benzyl group include benzyl group having one to three substituents of nitro or $C_{1-4}$ alkoxy such as benzyl, nitrobenzyl and methoxybenzyl; and examples of the optionally substituted phenyl include phenyl group having one to three substituents of nitro or $C_{1-4}$ alkoxy such as phenyl, nitrophenyl and methoxyphenyl. The more preferable examples of $COOR^2$ include a carboxyl group which may be esterified by a $C_{1-5}$ alkyl, especially methyl, and so on.

P denotes an integer of 1 to 4. When $-W-R^1$ denotes a moiety represented by the formula:

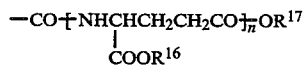

wherein $COOR^{16}$ and $COOR^{17}$ are, independently, an optionally esterified carboxyl group and n denotes an integer of 1 to 5, P denotes 1, 3 or 4. As the optionally esterified carboxyl group represented by $COOR^{16}$ and $COOR^{17}$, use is made of a carboxyl group which may be esterified by the group selected from the group consisting of a $C_{1-5}$ alkyl (e.g. methyl, ethyl, propyl, iso-propyl, n-butyl, iso-butyl, sec-butyl, tert-butyl, n-pentyl, iso-pentyl, sec-pentyl, neo-pentyl, tert-pentyl), optionally substituted benzyl preferably such as benzyl which may be substituted by a nitro or $C_{1-4}$ alkoxy (e.g. benzyl, nitrobenzyl, methoxybenzy), optionally substituted phenyl preferably such as phenyl which may be substituted by a nitro or $C_{1-4}$ alkoxy (e.g. phenyl, nitrophenyl, methoxyphenyl) and so on. When P is 2 and W is $-CO-NH-$, the optionally substituted cyclic group is more preferable as $R^1$.

Below described is the process for producing the compounds (I) of this invention or their salts.

The compound (I) or its salt can be obtained by acylating a compound (III) or its salt with a compound (II), its salt or reactive derivative at the carboxyl group. The above-mentioned acylating means includes, for example, a procedure of acylating the compound (III) or its salt with the compound (II), its salt or reactive derivative. It is advantageous to conduct this reaction in the presence of, for example, carbodiimides, diphenylphosphoric azide or diethyl cyanophosphate. The amount of the compound (III) or its salt to be used ranges usually from about 1 to 20 mole equivalents relative to the compound (II) or its salt, reactive derivative at the carboxyl group, preferably about 1 to 5 mole equivalents. The amount of carbodiimides, diphenylphosphoric azide and diethyl cyanophosphate to be used is usually in the range from about 1 to 25 mole equivalents, preferably about 1 to 5 mole equivalents relative to the compound (II) or its salt, reactive derivative at the carboxyl group.

As the carbodiimides, dicyclohexylcarbodiimide is desirable from the stand of practical use, while any other carbodiimides, for example, diphenylcarbodiimide, di-o-tolylcarbodiimide, di-p-tolylcarbodiimide, di-tert-butylcarbodiimide, 1-cyclohexyl-3-(2-morpholinoethyl)carbodiimide, 1-cyclohexyl-3-(4-diethylaminocyclohexyl)carbodiimide, 1-ethyl-3-(2-diethylaminopropyl)carbodiimide and 1-ethyl-3-(3-diethylaminopropyl)carbodiimide may be used.

This acylation reaction may be conducted in the presence of an adequate solvent, as exemplified by water, alcohols (e.g. methanol and ethanol), ethers (e.g. dimethyl ether, diethyl ether, tetrahydrofuran, dioxane, monoglyme and diglyme), nitriles (e.g. acetonitrile), esters (e.g. ethyl acetate), halogenated hydrocarbons (e.g. dichloromethane, chloroform and carbon tetrachloride), aromatic hydrocarbons (e.g. benzene, toluene and xylene), acetone, nitromethane, pyridine, dimethyl sulfoxide, dimethylformamide, hexamethylphosphoramide, sulfolane or suitable mixtures of them. This reaction is conducted at a pH usually in the region of about 2 to 14, preferably about 6 to 9, at temperatures usually ranging from about $-10°$ C. to the boiling point (up to about $100°$ C.) of the solvent then used, preferably about $0°$ to $50°$ C., usually for about 1 to 100 hours. The pH of the reaction solution is, upon necessity, adequately adjusted with, for example, acids (e.g. hydrochloric acid, sulfuric acid, phosphoric acid, nitric acid and acetic acid), bases (e.g. sodium methylate, sodium ethylate, sodium hydroxide, potassium hydroxide, lithium hydroxide, sodium carbonate, potassium carbonate, barium carbonate, calcium carbonate, sodium hydrogencarbonate, trimethylamine, triethylamine, triethanolamine and pyridine) or buffers (e.g. phosphate buffer, borate buffer and acetate buffer). This reaction can be allowed to proceed more advantageously by the aid of a catalyst capable of accelerating acylation. As such catalysts, use is made of, for example, base catalysts and acid catalysts. Examples of the base catalysts include tertiary amines (e.g. aliphatic tertiary amines such as triethylamine; aromatic tertiary amines such as pyridine, $\alpha$-, $\beta$- or $\gamma$-picoline, 2,6-lutidine, 4-dimethylaminopyridine, 4-(1-pyrrodinyl)pyridine, dimethylaniline and diethylaniline), while examples of the acid catalysts include Lewis acids [e.g. anhydrous zinc chloride, anhydrous aluminum chloride ($AlCl_3$), anhydrous ferric chloride, titanium tetrachloride ($TiCl_4$), tin tetrachloride ($SnCl_4$), antimony pentachloride, cobalt chloride, cupric chloride and boron trifluoride etherate].

Among the above-exemplified catalysts, 4-dimethylaminopyridine or 4-(1-pyrrolidinyl)pyridine is preferably employed in many cases. The amount of the catalysts to be employed ranges usually from about 0.1 to 10 mole equivalents relative to the compound (II) or its salt, reactive derivative at the carboxyl group, preferably from about 0.1 to 1 mole equivalent. Examples of the reactive derivative of the compound (II) in regard to the carboxyl group include derivative of the compound (II), such as its acid halide (e.g. fluoride, chloride, bromide and iodide), its acid anhydride (e.g. iodoacetic anhydride and isobutyric anhydride), its mixed acid anhydride with lower monoalkyl carbonate (e.g. monomethyl carbonate, monoethyl carbonate, monopropyl carbonate, monoisopropyl carbonate, monobutyl carbonate, monoisobutyl carbonate, mono-sec-butyl carbonate and mono-tert-butyl carbonate), its active esters (e.g. cyanomethyl ester, ethoxycarbonylmethyl ester, methoxymethyl ester, phenyl ester, o-nitrophenyl ester, p-nitrophenyl ester, p-carbomethoxyphenyl ester, p-cyanophenyl ester, phenylthio ester and succinimide ester), its acid azide, its mixed acid anhydride with diester of phosphoric acid (e.g. dimethyl phosphate, diethyl phosphate, dibenzyl phosphate and diphenyl phosphate) and its mixed anhydrides with diester of phosphorous acid (e.g. dimethyl phosphite, diethyl phosphite, dibenzyl phosphite and diphenyl phosphite). In the acylation process using these reactive derivatives, the reaction conditions such as the solvent, catalyst, reaction temperatures and reaction time are substantially the same as those described previously referring to the acylation conducted in the presence of carbodiimide and so on.

Incidentally, in the case of producing the compound or a salt thereof which has a hydroxyl group, amino group, mercapto group or carboxyl group in the compound (I) or its salt, the object compound (I) or its salt can be produced by protecting the hydroxyl group, amino group, mercapto group or carboxyl group of the starting compound with a per se known protective group according to a per se known method (e.g. J. F. W. McOmine, Protective Groups in Organic Chemistry, Plenum Press, London and New York (1973)) followed by subjecting the reaction product to a per se known deprotection reaction.

Described in the following is the procedure of producing the starting compound (II), its salt or reactive derivative at the carboxyl group.

The reactive derivative at the carboxyl group of the compound (II) include, among others, acid halide (e.g. acid chloride, acid bromide, etc.), acid anhydride, mixed acid anhydride (e.g. anhydride with methyl carbonate, anhydride with ethyl carbonate, anhydride with isobutyl carbonate, etc.), active ester (e.g. N-hydroxysuccinimide ester, 1-hydroxybenzotriazole ester, N-hydroxy-5-norbornene-2,3-dicarboximide ester, p-nitrophenol ester, 8-oxyquinoline ester, etc.). Among them, acid halide is preferable.

The compound (II), its salt or reactive derivative at the carboxyl group can be produced by, for example, the following reaction steps.

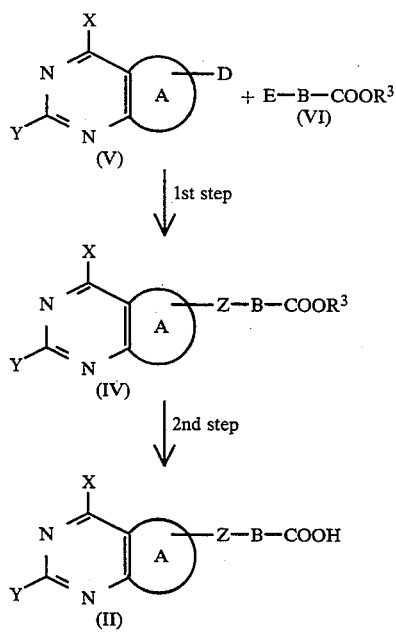

In the above formulae, the ring A, B, D, Y and Z are of the same meaning as defined above, and examples of $R^3$ at the optionally esterified carboxyl group represented by $COOR^3$ include hydrogen atom, or a $C_{1-5}$ alkyl group, optionally substituted benzyl group or an optionally substituted phenyl group specifically described referring to $COOR^2$; D and E are group being capable of combining with each other to form Z. In the above reaction steps, the covalent bond can be allowed to form between D and E to thereby produce a straight-chain divalent aliphatic group having five or less chain-composing atoms optionally bonded through a heteroatom at the site of chain. Referring to the synthetic method which permits formation of the covalent bond between the compound (V) or its salt and the compound (VI) or its salt, wherein Z is an optionally substituted divalent aliphatic group having five or less straight-chain atoms, the compound (V) or its salt and the compound (VI) or its salt can be subjected to the so-called reaction causing carbon-carbon bond, followed by subjecting the resultant to reduction, when necessary, to thereby produce the compound (V) or its salt, in case, for example, where D is

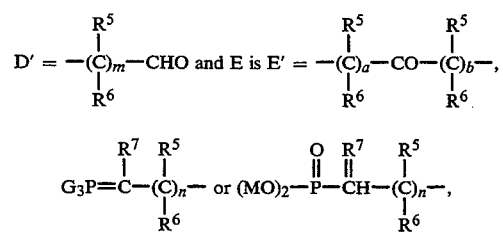

or in the case of vice versa $D=E'$ and $E=D'$.

In the above formulae, a, b, m, n ($=a+b$) and $m+n$ each denotes an integer in the range of 0 to 3; G stands for phenyl, butyl or cyclohexyl; M stands for ethyl or phenyl; $R^5$, $R^6$ and $R^7$ independently stand for a bond, a hydrogen atom, the divalent lower hydrocarbon group represented by $Z^1$ and $Z^2$ described specifically, or the lower hydrocarbon group represented by $R^4$, and they may be different from one another in repeating units m and n.

In the case of Z being a group composed of Z=—Z$^1$—Z$^2$—Z$^3$—, in the case of, for example,

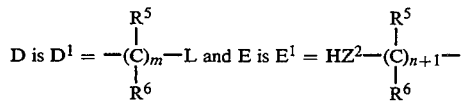

D is D$^1$ = —(C)$_m$—L and E is E$^1$ = HZ$^2$—(C)$_{n+1}$— or in the case of vice versa D=E and E=D', the so-called alkylation reaction is employed, and in the case of, for example, where D is

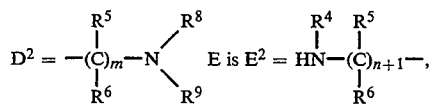

D$^2$ = —(C)$_m$—N(R$^8$)(R$^9$)    E is E$^2$ = HN—(C)$_{n+1}$—, or in the case of vice versa D=E$^2$, E=D$^2$, so-called amine exchange reaction (glamine decomposition reaction) is advantageously employed, and in cases where D is

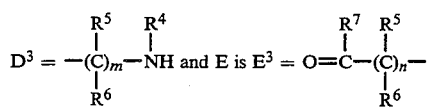

D$^3$ = —(C)$_m$—NH and E is E$^3$ = O=C—(C)$_n$— or in the case of vice versa D=E$^3$ and E=D$^3$, a Schiff base or enamine is allowed to form, followed by reduction, when necessary, or subjecting directly to a reductive alkylation reaction.

In the above formulae, m, n, m+n, R$^4$, R$^5$, R$^6$, R$^7$ and Z$^2$ are of the same meaning as defined hereinbefore; L stands for a leaving group; and R$^8$ and R$^9$ independently stand for a hydrogen atom or a hydrocarbon group. The leaving group represented by L include, for example, halogen atom (e.g. chlorine, bromine, iodine) or removable group derived easily from hydroxyl group (e.g. methanesulfonyloxy group, benzenesulfonyloxy group, p-toluenesulfonyloxy group and trifluoromethanesulfonyl group). The hydrocarbon group represented by R$^8$ and R$^9$ may have substituents, and R$^8$ and R$^9$ may form a cyclic amino group, taken together with adjacent nitrogen atom.

Examples of the hydrocarbon group represented by R$^8$ and R$^9$ include C$_{1-18}$ alkyl group (e.g. methyl, ethyl, propyl, isopropyl, butyl, isobutyl, sec-butyl, tert-butyl, pentyl, isopentyl, hexyl, isohexyl, heptyl, octyl, nonyl, decyl, undecyl, dodecyl, tetradecyl, hexadecyl, octadecyl, 1,2-dimethylpropyl, 1-ethylpropyl, 1,2,3-trimethylpropyl, 1-propylbutyl and 2-ethylhexyl group), C$_{1-12}$ alkenyl group (e.g. vinyl, allyl, 1-methylvinyl, 2-methylvinyl, 1-octenyl, 1-decenyl group), C$_{3-12}$ cycloalkyl group (e.g. cyclopropyl, cyclobutyl, cyclopentyl, cyclohexyl, cycloheptyl, cyclooctyl, adamantyl group), C$_{3-8}$ cycloalkenyl group (e.g. cyclopentenyl, cyclohexenyl, cycloheptenyl, cyclooctenyl, cyclopentadienyl, cyclohexadienyl, cycloheptadienyl, cyclooctadienyl group), C$_{7-13}$ aralkyl group (e.g. benzyl, alpha-methylbenzyl, phenethyl and diphenylmethyl group) and C$_{6-10}$ aryl group (e.g. phenyl, alpha-naphthyl and beta-naphthyl group). Preferred examples of the cyclic amino group which R$^8$ and R$^9$ cooperate with the adjacent nitrogen atom to form include 4- to 10-membered ring such as azetidinyl, pyrrolidinyl, pyrrolinyl, pyrrolyl, imidazolyl, pyrazolyl, imidazolinyl, piperidino, morpholino, dihydropyridyl, tetrahydropyridyl, N-methylpiperazinyl, azacycloheptyl, azacyclooctyl, isoindolyl, indolyl, indolinyl, 2-isoindolinyl, azacyclononyl and azacyclodecyl group.

The hydrocarbon group represented by R$^8$ and R$^9$ and the the rings formed by R$^8$ and R$^9$ in cooperation with the adjacent nitrogen atom may have one or two substituents.

Examples of these substituents include C$_{1-4}$ alkyl group (e.g. methyl, ethyl, propyl, isopropyl, butyl, isobutyl, sec-butyl and tert-butyl group), C$_{1-4}$ alkoxy group (e.g. methoxy, ethoxy, propoxy, iso-propoxy, n-butoxy, isobutoxy, sec-butoxy, tert-butoxy group), C$_{1-4}$ alkanoyl group (e.g. formyl, acetyl, propionyl, n-butyryl, isobutyryl group), C$_{1-4}$ alkanoyloxy group (e.g. formyloxy, acetyloxy, propionyloxy, n-butyryloxy, isobutyryloxy group), carboxyl group, C$_{2-4}$ alkoxycarbonyl group (e.g. methoxycarbonyl, ethoxycarbonyl, n-propoxycarbonyl, iso-propoxycarbonyl, n-butoxycarbonyl, isobutoxycarbonyl, tert-butoxycarbonyl group), halogen atom (e.g. fluorine, chlorine, bromine, iodine), hydroxyl group, nitro group, cyano group, trifluoromethyl group, amino group, mono-substituted amino group (e.g. methylamino, ethylamino, propylamino, isopropylamino, butylamino group), di-substituted amino group (e.g. dimethylamino, diethylamino, dipropylamino, diisopropylamino and dibutylamino group), alkanoylamido group (e.g. formamido, acetamido, trifluoroacetamido, propionylamido, butyrylamido, isobutyrylamido group), carbamoyl group, N-substituted carbamoyl group (e.g. N-methylcarbamoyl, N-ethylcarbamoyl, N-propylcarbamoyl, N-isopropylcarbamoyl, N-butylcarbamoyl group), N,N-disubstituted carbamoyl group (e.g. N,N-dimethylcarbamoyl, N,N-diethylcarbamoyl, N,N-dipropylcarbamoyl, N,N-dibutylcarbamoyl, 1-aziridinylcarbonyl, 1-azetidinylcarbonyl, 1-pyrrolidinylcarbonyl, 1-piperidinylcarbonyl, N-methylpiperazinylcarbonyl, morpholinocarbonyl group), carbamoylamino group, N-substituted carbamoylamino group (e.g. N-methylcarbamoylamino, N-ethylcarbamoylamino, N-propylcarbamoylamino, N-isopropylcarbamoylamino and N-butylcarbamoylamino group), N,N-disubstituted carbamoylamino group (e.g. N,N-dimethylcarbamoylamino, N,N-diethylcarbamoylamino, N,N-dipropylcarbamoylamino, N,N-dibutylcarbamoylamino, 1-aziridinylcarbonylamino, 1-azetidinylcarbonylamino, 1-pyrrolidinylcarbonylamino, 1-piperidinylcarbonylamino, N-methylpiperazinylcarbonylamino, morpholinocarbonylamino group), mercapto group, sulfo group, sulfino group, phosphono group, sulfamoyl group, N-substituted sulfamoyl group (e.g. N-methylsulfamoyl, N-ethylsulfamoyl, N-propylsulfamoyl, N-isopropylsulfamoyl, N-butylsulfamoyl group), N,N-disubstituted sulfamoyl group (e.g. N,N-dimethylsulfamoyl, N,N-diethylsulfamoyl group (e.g. N,N-dimethylsulfamoyl, N,N-diethylsulfamoyl, N,N-dipropylsulfamoyl, N,N-diethylsulfamoyl, N,N-dipropylsulfamoyl, N,N-dibutylsulfamoyl, 1-pyrrolidinylsulfonyl, 1-piperidinylsulfonyl, N-methyl-1-piperazinylsulfonyl, morpholinosulfonyl group), C$_{1-4}$ alkylthio group (e.g. methylthio, ethylthio, propylthio, isopropylthio, n-butylthio, sec-butylthio, tert-butylthio group), C$_{1-4}$ alkylsulfinyl group (methylsulfinyl, ethylsulfinyl, propylsulfinyl and butylsulfinyl group) and C$_{1-4}$ alkylsulfonyl group (e.g. methylsulfonyl, ethylsulfonyl, propylsulfonyl, butylsulfonyl group).

Below given is the detailed description of the first step:

First step:

For the condensation reaction through the formation of carbon-carbon bonding, is employable according to a known reaction (e.g. aldol reaction, Reformatsky reaction or Wittig reaction), and, as the reduction reaction, catalytic reduction or hydride reduction is usually employed advantageously. In the case of employing aldol reaction for the condensation reaction, as the base catalyst, use is made of, for example, a metal hydroxide such as sodium hydroxide, potassium hydroxide, lithium hydroxide or barium hydroxide; a metal alkoxide such as sodium methoxide, sodium ethoxide or potassium tert-butoxide; a metal amide such as sodium amide or lithium diisopropylamide; a metal hydride such as sodium hydride or potassium hydride; an organometallic compound such as phenyllithium or butyllithium; and an amine such as triethylamine, pyridine, alpha-, beta- or gamma-picoline, 2,6-lutidine, 4-dimethylaminopyridine, 4-(1-pyrrolidinyl)pyridine, dimethylaniline or diethylaniline; while as the acid catalyst, use is made of, for example, a mineral acid such as hydrochloric acid, sulfuric acid, nitric acid, phosphoric acid or boric acid; and n organic acid such as oxalic acid, tartaric acid, acetic acid, trifluoroacetic acid, methanesulfonic acid, benzenesulfonic acid, p-toluenesulfonic acid or camphorsulfonic acid. Alternatively, the condensation can be conducted by, in accordance with a known method [Ei-Ichi Negishi, Organometallic in Organic Synthesis Vol. 1, John Wiley & Sons, New York, Chichester, Brisbane, Tronto (1980)], deriving a silylenol ether compound from ketone, which is subjected to condensation with aldehyde or its equivalent in the presence of a Lewis acid [e.g. anhydrous zinc chloride, anhydrous aluminum chloride ($AlCl_3$), anhydrous ferric chloride, titanium tetrachloride ($TiCl_4$), tin tetrachloride ($SnCl_4$), antimony pentachloride, cobalt chloride, cupric chloride or boron trifluoride etherate], fluorine anion (e.g. tetrabutyl ammonium fluoride) or trityl perchlorate, or by processing the ketone compound with a metal triflate [e.g. dialkyl boron triflate or tin(II) triflate] in the presence of an amine [e.g. triethylamine, pyridine, $\alpha$-, $\beta$- or $\gamma$-picoline, 2,6 -lutidine, 4-dimethylaminopyridine, 4-(1-pyrrolidinyl)pyridine, dimethylaniline or diethylaniline] to convert into the enolate, then by subjecting the enolate to condensation with aldehdye or its equivalent. The condensation reaction can be carried out in an appropriate solvent at temperatures ranging from $-100°$ C. to the boiling point of the solvent then employed, preferably $-78°$ to $100°$ C., for a period ranging from one minute to three days. Examples of the reaction solvent include water, liquid ammonia, alcohol (e.g. methanol, ethanol, propanol, iso-propanol, butyl alcohol, sec-butyl alcohol tert-butyl alcohol, ethylene glycol, methoxyethanol or ethoxyethanol), ether (e.g. dimethyl ether, diethyl ether, tetrahydrofuran, dioxane, monoglyme or diglyme), halogenated hydrocarbon (e.g. dichloromethane, chloroform or carbon tetrachloride), aliphatic hydrocarbon (e.g. pentane, hexane or heptane), aromatic hydrocarbon (e.g. benzene, toluene or xylene), acetonitrile, nitromethane, dimethylformamide, dimethyl sulfoxide, hexamethylphosphoramide, sulfolane or a suitable mixture of them. In the case of resorting to Wittig reaction for the condensation, reagents to be employed are exemplified by a metal hydroxide such as sodium hydroxide, potassium hydroxide, lithium hydroxide or barium hydroxide; a metal alkoxide such as sodium methoxide, sodium ethoxide or potassium tert-butoxide; a metal amide such as sodium amide or lithium diisopropylamide; a metal hydride such as sodium hydride or potassium hydride; an organometallic compound such as phenyllithium or butyl lithium; and an amine such as trimethylamine, pyridine, alpha-, beta- or gamma-picoline, 2,6-lutidine, 4-dimethylaminopyridine, 4-(1-pyrrolidinyl)pyridine, dimethylaniline or diethylaniline. The reaction is carried out in an appropriate solvent at temperatures ranging from $-20°$ C. to the boiling point of the solvent then used, preferably $0°$ to $150°$ C., for a period ranging from one minutes to ten days. As the solvent, use is made of, for example, liquid ammonia, alcohol (e.g. methanol, ethanol, propanol, iso-propanol, butyl alcohol, sec-butyl alcohol, tert-butyl alcohol, ethylene glycol, methoxyethanol or ethoxyethanol), ether (dimethyl ether, diethyl ether, tetrahydrofuran, dioxane, monoglyme or diglyme), aliphatic hydrocarbon (e.g. benzene, toluene or xylene), dimethylformamide, dimethyl sulfoxide, hexamethyl phosphoramide, sulfolane or a suitable mixture of them. Furthermore, Reformatskii reaction can be employed for causing the condensation. Referring to the conditions for Reformatskii reaction, the reagent which is usable includes, for example, zinc, magnesium, aluminum or tin, and the reaction itself can be conducted at temperatures ranging from $-20°$ C. to the boiling point of the solvent then used, preferably $0°$ to $150°$ C., for a period ranging from 30 minutes to three days. As the solvent, there may be used, for example, ether (e.g. dimethyl ether, diethyl ether, tetrahydrofuran, dioxane, monoglyme or diglyme) aliphatic hydrocarbon (e.g. pentane, hexane or heptane), aromatic hydrocarbon (e.g. benzene, toluene or xylene) or a suitable mixture of them.

The alkylation type reaction or amine exchange type reaction is conducted by allowing a compound (V) or its salt and a compound (VI) or its salt to undergo reaction, as such or in an appropriate reaction solvent, at temperatures ranging from about $-10°$ C. to the boiling point of the solvent then employed, preferably about $10°$ to $80°$ C., for a period ranging from about ten minutes to 48 hours. The ratio of the compound (VI) or its salt to be used ranges from 1 to 50 moles relative to 1 mol of the compound (V) or its salt, more preferably about 1 to 10 moles. The reaction solvent is exemplified by water, alcohol (e.g. methanol, ethanol, propanol, iso-propanol, butyl alcohol, sec-butyl alcohol, tert-butyl alcohol, ethylene glycol, methoxyethanol or ethoxyethanol), ether (e.g. diethyl ether, tetrahydrofuran, dioxane, monoglyme or diglyme), halogenated hydrocarbon (e.g. dichloromethane, chloroform or carbon tetrachloride), nitrile (e.g. acetonitrile), aliphatic hydrocarbon (e.g. pentane, hexane, heptane or octane), cyclic aliphatic hydrocarbon (e.g. cyclopentane or cyclohexane), aromatic hydrocarbon (e.g. benzene, toluene or xylene), nitromethane, pyridine, dimethylformamide, dimethyl sulfoxide, hexamethyl phosphoramide, sulfolane or a suitable mixture of them. And, it is, in some instances, desirable to carry out the reaction in the presence of a base, when necessary. Furthermore, when a phase-transfer catalyst (e.g. cetyl trimethylammonium chloride) is used in an amount of 0.01 to 0.2 equivalent, preferably about 0.02 to 0.05 equivalent, relative to the compound (V) or its salt, or the compound (VI) or its salt, the reaction can be allowed to proceed advantageously as well. In the case of the amine exchange type reaction, the reaction can in some instances be allowed to proceed under milder conditions, when a compound (V) or its salt is converted into a quaternary salt, such as the salt with methyl bromide, methyl iodide, methyl methanesulfonate, methyl benzenesulfonate or methyl p-toluenesulfonate. The above-mentioned reaction causing a Schiff base to be formed is conducted by allowing a compound (V) or its salt and a compound (VI) or its salt, as such or in an appropriate solvent, to undergo reaction at a molar ratio of (V)/(VI)=about 10 to 0.1 at temperatures ranging from −10° C. to the boiling point of the solvent then used, preferably 0° to 50° C. for a period of time in the region of about ten minutes to 48 hours. In this reaction, the compound (V) or its salt and (VI) or its salt, after having their aldehyde or ketone moieties protected in the form of acetal or ketal, may be used as well. As the reaction solvent, a non-aqueous one is preferable, which is exemplified by alcohol (e.g. methanol, ethanol, propanol, isopropanol, butyl alcohol, sec-butyl alcohol, tert-butyl alcohol, ethylene glycol, methoxyethanol or ethoxyethanol) ether (e.g. dimethyl ether, diethyl ether, tetrahydrofuran, dioxane, monoglyme or diglyme), ester (e.g. methyl acetate or ethyl acetate), halogenated hydrocarbon (e.g. dichloromethane, chloroform or carbon tetrachloride), nitrile (e.g. acetonitrile), aliphatic hydrocarbon (e.g. pentane, hexane, heptane or octane), cyclic aliphatic hydrocarbon (e.g. cyclopentane or cyclohexane), aromatic hydrocarbon (e.g. benzene, toluene or xylene), acetone, nitromethane, pyridine, dimethylformamide, dimethyl sulfoxide, hexamethyl phosphoramide, sulfolane or a suitable mixture of them. As a dehydrating agent, for example, molecular sieves, calcium chloride, magnesium sulfate, sodium sulfate or calcium sulfate is added, or the pH value of the reaction mixture is adequately adjusted with an acid (e.g. hydrochloric acid, hydrobromic acid, hydriodic acid, sulfuric acid, nitric acid or phosphoric acid), a base (e.g. a metal hydroxide such as sodium hydroxide, potassium hydroxide, lithium hydroxide or barium hydroxide; sodium methoxide, sodium ethoxide, potassium tert-butoxide, sodium carbonate, potassium carbonate, barium carbonate, calcium carbonate, sodium hydrogencarbonate, trimethylamine, triethylamine, triethanolamine or pyridine) or a buffer solution (e.g. phosphate buffer, borate buffer or acetate buffer) to thereby enhance and improve the reaction rate and yields. The reduction and reductive alkylation of the Schiff base are carried out through hydride reduction or catalytic reduction in an appropriate solvent at temperatures ranging from about −40° C. to the boiling point of the solvent then employed, more preferably about 0° to 50° C. As the solvent employable, mention is made of, besides the solvents usable in the alkylation type reaction or amine exchange type reaction as described previously, acetic acid ester (e.g. methyl acetate or ethyl acetate). The catalytic reduction is carried out by using an adequate solvent at temperatures ranging form about −40° C. to the boiling point of the solvent, more preferably about 0° to 50° C. As the solvent, use is made of, for example, water, alcohol (e.g. methanol, ethanol, propanol, iso-propanol, butyl alcohol sec-butyl alcohol, tert-butyl alcohol, ethylene glycol, methoxyethanol or ethoxyethanol), acetic acid ester (e.g. methyl acetate or ethyl acetate), ether (e.g. dimethyl ether, diethyl ether, tetrahydrofuran, dioxane, monoglyme or diglyme), aromatic hydrocarbon (e.g. benzene, toluene or xylene), pyridine, dimethylformamide or a suitable mixture of them. As the catalyst for catalytic reduction, use is made of, for example, palladium, platinum, rhodium or Raney nickel. In this case, the reaction can, in some instances, be allowed to proceed advantageously by adding a small amount of acetic acid, trifluoracetic acid, hydrochloric acid or sulfuric acid. Examples of the reagent in the hydride reduction include lithium aluminum hydride, sodium borohydride, lithium borohydride or sodium cyanoborohydride, and the amount of the reagent to be employed ranges from about equimole to 100-fold moles, usually 2-fold to 20-fold the molar quantity.

And, when the ring A is furan, thiophene, thiophen-1-oxide, thiophene-1,1-dioxide or N-substituted pyrrole ring and —$Z^2$— is —NH—, the said group —NH—, in some instances, undergoes ring-closure with the ring A to form a tricyclic compound (e.g. pyrrolo[3',2':4,5]pyrrolo[2,3-d]pyrimidine derivative). In this case, the tricyclic compound can be easily converted to the object dicyclic compound by processing with an acid or a base.

Second Step:

The compound (IV) or its salt as obtained in the first step can be converted into, the compound (II) or its salt by allowing its ester residual group [—$COOR^3$] to undergo the per se known deprotection reaction as employed in the production of the compound (I) or its salt.

And, the starting compound (II) or its salt can be produced also by the reaction steps as shown in the following.

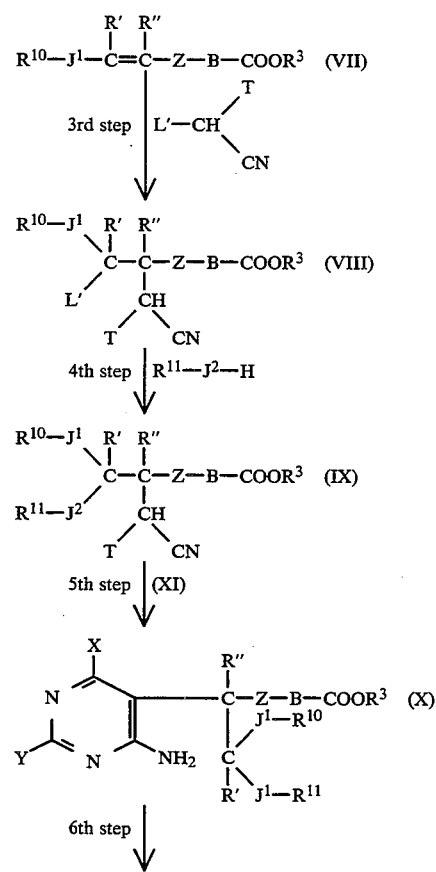

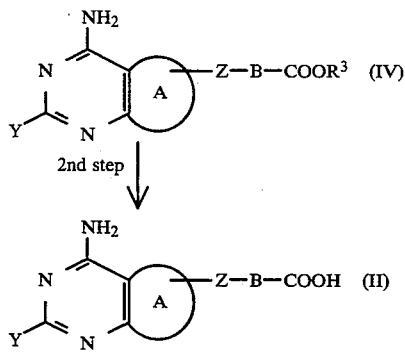

In the above reaction steps, the ring A, B, R³, X, Y and Z are of the same meaning as defined above; J¹ and J² independently stand for oxygen or sulfur; R¹⁰ and R¹¹ independently stand for a hydrocarbon group; L' stands for a halogen atom (e.g. chlorine, bromine or iodine); T stands for a cyano group or a group represented by —COOR¹², —CSOR¹² or —CSSR¹² [wherein R¹² stands for a hydrocarbon residual group]; R' and R" independently stand for hydrogen atom or a $C_{1-3}$ alkyl group, a $C_{2-3}$ alkenyl group, a $C_{2-3}$ alkynyl group or a cyclopropyl group as described in detail as the substituents on the ring A. Examples of the hydrocarbon residue represented by R¹⁰, R¹¹ and R¹² include $C_{1-5}$ lower alkyl group (e.g. methyl, ethyl, propyl, iso-propyl, n-butyl, iso-butyl, sec-butyl, tert-butyl, n-pentyl, iso-pentyl, sec-pentyl, neo-pentyl and tert-pentyl group). These lower alkyl, benzyl and phenyl group may have one to three substituents. Such substituents include, for example, halogen atom (e.g. fluorine, chlorine, bromine, iodine), nitro group, cyano group, alkoxy group having about one to four carbon atoms (e.g. methoxy, ethoxy, propoxy, iso-propoxy, n-butoxy, iso-butoxy, sec-butoxy, tert-butoxy group), $C_{1-4}$ alkyl group (e.g. methyl, ethyl, propyl, isopropyl, butyl, iso-butyl, sec-butyl, tert-butyl group), alkanoyl group of about one to four carbon atom (e.g. formyl, acetyl, propionyl, n-butyryl, iso-butyryl group), trifluoromethyl group and so on.

Given below is detailed description on the above reaction steps:

Third Step:

This is a step of producing the compound (VIII) or its salt by subjecting the double bond $$(R^{10}-J^1-\overset{R'}{\underset{|}{C}}=\overset{R''}{\underset{|}{C}}-)$$

of the compound (VII) or its salt to addition reaction to

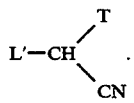

The amount of

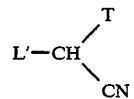

relative to the starting compound (VII) or its salt. The amount to be used ranges generally from about 0.5 to 4 mole equivalents, preferably about 0.8 to 1.5 mole equivalents. This reaction can be carried out in an adequate solvent at temperatures ranging from about $-10°$ C. to the boiling point of the solvent (up to about 100° C.), preferably about 0° to 50° C., for about 30 minutes to 48 hours. Examples of the solvent include alcohol (e.g. methanol and ethanol), ether (e.g. dimethyl ether, diethyl ether, tetrahydrofuran, dioxane, monoglyme and diglyme), nitrile (e.g. acetonitrile), ester (e.g. ethyl acetate), halogenated hydrocarbon (e.g. dichloromethane, chloroform and carbon tetrachloride), aromatic hydrocarbon (e.g. benzene, toluene and xylene) or a suitable mixture of them. In conducting the reaction, irradiation of light or addition of an organic peroxide can, in some instances, permit the reaction to proceed more advantageously. Examples of the organic peroxide include t-butyl hydroperoxide, peracetic acid, perbenzoic acid and m-chloroperbenzoic acid. The compound (VIII) or its salt as obtained by the above procedure is of relatively high reactivity and may be isolated in this stage, while it can also be used directly in the following step without being isolated.

Fourth step:

The compound (VIII) or its salt as obtained in the third step can be led to the compound (IX) or its salt by allowing the former to react with alcohol or thiol represented by R¹¹—J²—H in an appropriate solvent at temperatures ranging from about $-10°$ C. to the boiling point (up to about 100° C.) of the solvent then employed, preferably about 0° to 50° C., for about 10 minutes to 24 hours. Examples of the solvent to be employed include ether (e.g. dimethyl ether, diethyl ether, tetrahydrofuran, dioxane, monoglyme or diglyme), nitrile (e.g. acetonitrile), ester (e.g. ethyl acetate), halogenated hydrocarbon (e.g. dichloromethane, chloroform or carbon tetrachloride), aromatic hydrocarbon (e.g. benzene, toluene or xylene) or a suitable mixture of them. Incidentally, the alcohol or thiol represented by R¹¹—J²—H may be used in excess to utilize for the solvent as well.

Fifth step:

The compound (IX) or its salt, upon reaction with a compound represented by the formula

[wherein Y is of the same meaning as defined above] or a salt thereof, is led to the compound (X) or its salt by the reaction through the cyano, ester or thioester group to cause cyclization to form the pyrimidine ring.

The acid salt of the compound (XI) or its salt includes, for example, salts with a mineral acid such as hydrochloric acid, hydrobromic acid, hydriodic acid, sulfuric acid, nitric acid, phosphoric acid or boric acid, and with an organic acid such as oxalic acid, tartaric acid, lactic acid, citric acid, acetic acid, trifluoroacetic acid, methanesulfonic acid, ethanesulfonic acid, benzenesulfonic acid or camphorsulfonic acid, while the base salt of the compound (XI-1: Y'=hydroxyl or mercapto group) include, for example, salts formed with sodium, potassium, lithium, calcium, magnesium, aluminum, zinc, ammonium, trimethyl ammonium, triethyl ammonium, pyridinium or substituted pyridinium.

The reaction for ring-closure can, in some instances, be allowed to proceed advantageously under basic conditions. As the base, use is made of, for example, metal alkoxide such as sodium methoxide, sodium ethoxide or potassium tert-butoxide. Examples of the reaction solvent include methanol, ethanol, propanol, tert-butyl alcohol, dimethyl sulfoxide or hexamethyl phosphoramide. The reaction temperatures range from 0° to 150° C., preferably 20° to 100° C., and the reaction time ranges from one to 48 hours. Examples of the reaction solvent include methanol, ethanol, propanol, tert-butyl alcohol, dimethyl sulfoxide, hexamethyl phosphoramide or a suitable mixture of them.

Sixth step:

When necessary, the group of the formula

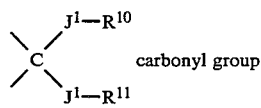
carbonyl group in the compound (X) or its salt is restored to a carbonyl group ($>C=O$), bringing about spontaneously an intramolecular ring-closure reaction and dehydration reaction to thereby convert the compound (X) or its salt into the compound (IV) or its salt. The restoration reaction to the carbonyl group can be carried out by subjecting the compound (X) or its salt, as such or in a suitable solvent, to a per se known restoration reaction at temperatures ranging from about $-10°$ C. to the boiling point (up to about 100° C.) of the solvent then employed, preferably about 0° to 50° C. for about 10 minutes to 100 hours. The intramolecular ring-closure and dehydration reactions in the step of producing the compound (IV) or its salt normally allow the group X on the pyrimidine ring to condense spontaneously to the carbonyl group ($>C=O$) in the course of or after restoration to thereby form the ring A. In conducting the the reaction, it is also possible to allow the the reaction to proceed promptly and in an improved yield by permitting an acid catalyst to present in the reaction system. As the acid catalyst, use is made of, for example, mineral acids, organic acids or Lewis acids as described in detail referring to the aldol reaction. Also the carbonyl group ($>C=O$) can be reduced to a hydroxymethyl group ($>CHOH$), whose hydroxy moiety is converted into a leaving group L, followed by alkylation reaction with the group X in the same molecule to thereby product the compound (IV) or its salt having the ring A reduced partially. The carbonyl-group reduction, conversion of the hydroxyl group into the leaving group and the intramolecular alkylation are carried out according to per se known procedures. In addition, the compound (II) or its salt, or (IV) or its salt can be subjected to a catalytic reduction according to a per se known procedure to perform partial reduction to thereby to convert into the compound (II) or its salt, or the compound (IV) or its salt wherein the ring A is partially reduced. In the case of the compound (II) or its salt whose ring A is pyrrole or pyrroline ring, the compound (X) or its salt, or the compound (IV) or its salt can be subjected to a per se known alkylation or acylation reaction to thereby convert into a compound having an N-substituted pyrrole or N-substituted pyrroline ring, which falls into the scope of this invention. Furthermore, the compound of this invention whose ring A is an N-substituted pyrrole or N-substituted pyrroline ring can be produced also by conducting the above-mentioned alkylation or acylation reaction employing the compound (IV), (II) or its salt whose the ring A is an unsubstituted pyrrole or unsubstituted pyrroline ring which is described in Japanese Patent Publication Laid Open No. 167281/1990.

The starting compound (II) or its salt, whose ring A consists solely of carbon atoms, can be produced by, for example, the reaction steps as shown in the following:

Chemical Formula 21

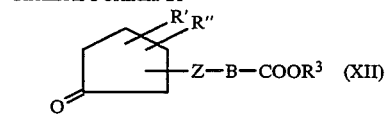

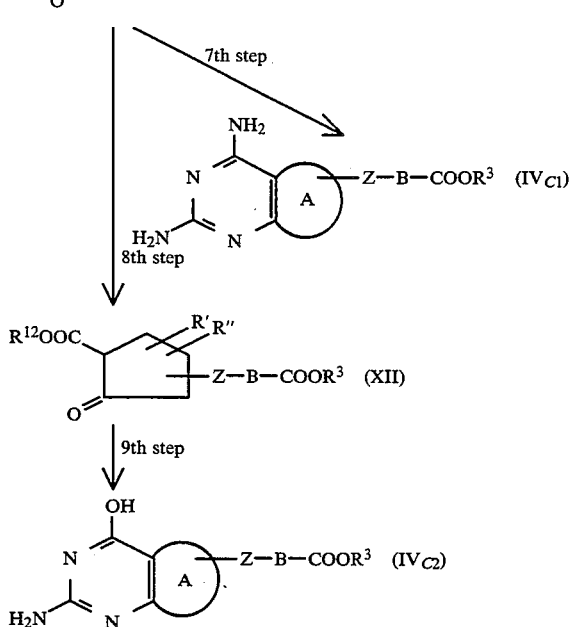

In the above reaction steps, the ring A, B, $R^3$, $R^{12}$, R', R" and Z are of the same meaning as defined hereinbefore, and R', R" and $-Z-B-COOR^3$ are to be understood to form bonding in the consecutive three positions on the cyclopentane ring.

Seventh step:

The compound (XII) or its salt as synthesized by a conventional procedure, upon treatment under heating with dicyandiamide, undergoes cyclization to form a condensed pyrimidine ring, thus yielding the compound ($IV_{C1}$) or its salt. In this case, the reaction temperatures ranges form 100° to 300° C., more preferably 150° to 250° C., and the suitable reaction time ranges from one to 24 hours. When required further, dehydrogenation can be effected by following a per se known procedure with a known reagent to introduce an unsaturated bond into the ring A.

Eighth step:

Out of the two alpha-positions adjacent to the carbonyl group in the compound (XII) or its salt, the hydrogen at the alpha-position, which is not substituted with R', R" or —Z—B—COOR³, is drawn in accordance with a conventional method to cause formation of carbanion, and an ester residue (e.g. carboxyl group which is esterified by a $C_{1-6}$ alkyl such as methyl, ethyl, n-propyl, iso-propyl, n-butyl, tert-butyl, or $C_{7-8}$ aralkyl such as benzyl) is introduced into the activated position to thereby produce the compound (XIII) or its salt.

Ninth step:

The compound (XIII) or its salt, upon treatment with the compound of the general formula (XI), reacts with its carbonyl group and ester residue to cause ring-closure and cyclization to form a condensed pyrimidine ring anew to thereby produce the compound ($IV_{C2}$) or its salt. As the reaction conditions, those employed in the fifth step are applied as such. When necessary furthermore, dehydrogenation can be performed in accordance with a per se known method by using a known reagent to introduce an unsaturated bond into the ring A.

The ester derivatives ($IV_{C1}$), ($IV_{C2}$) or its salt, as obtained in the 7th and 9th reaction steps, can be converted into respectively corresponding carboxylic acid derivatives by subjecting to deesterification.

In cases where B is a cycloalkenylene group or a substituted phenylene group, such group may be subjected to a catalytic reduction in any suitable one of the first to the ninth steps according to a per se known procedure to thereby convert into corresponding cycloalkylene group.

In cases Y is a hydroxyl, alkoxyl, aryloxy, 5- or 6-membered heterocyclic-oxy, mercapto, alkylthio, arylthio, 5- or 6-membered heterocyclic-thio, substituted amino, alkanoylamino, aroylamino or 5- or 6-membered heterocyclic-carbonylamino group, such group may be subjected to a conversion reaction in any suitable one of the second, sixth, seventh and ninth steps according to a per se known procedure to thereby convert into a 5- or 6-membered heterocyclic group, halogen atom, cyano group, carboxyl group, carbamoyl group, nitro group, hydroxyl group, alkoxyl group, aryloxy group, 5- or 6-membered heterocyclic-oxy group, mercapto group, alkylthio group, arylthio group, 5- or 6-membered heterocyclic-thio group, substituted amino group, alkanoylamino group, aroylamino group, 5- or 6-membered heterocyclic-carbonylamino group, alkanoyloxy group, aroyloxy group or 5- or 6-membered heterocyclic-carbonyloxy group as exemplified by Y.

In cases where the ring A and B contain a sulfur atom or —Z²— is —S— (sulfur atom), the compound (I) or its salt of this invention can be converted into the compound wherein the sulfur atom of the ring A, B and —Z²— is changed into S(O)n [n=1 or 2] by subjecting the compound (I) or its salt to oxidation directly or in an optional one of the feasible steps. The reaction for oxidation can be carried out in an appropriate solvent, usually in the presence of an oxidizing agent of 0.3 to 3.0 equivalents relative to the compound to be oxidized, preferably 0.5 to 2.5 equivalents at temperatures ranging from −10° to +100° C., preferably 0° to +50° C. for 10 minutes to 48 hours, preferably 30 minutes to 24 hours. Preferred examples of the oxidizing agent to be used for the reaction include peracids (e.g. sodium metaperiodate, hydrogen peroxide, peracetic acid, perbenzoic acid and m-chloroperbenzoic acid). Examples of the reaction solvent to be employed include water, acetic acid ketone (e.g. acetone and ethyl methyl ketone), ether (e.g. dimethyl ether, diethyl ether, dioxane, monoglyme and diglyme), halogenated hydrocarbon (e.g. dichloromethane, chloroform and carbon tetrachloride), aliphatic hydrocarbon (e.g. pentane, hexane, heptane and octane), cyclic aliphatic hydrocarbon (e.g. cyclopentane and cyclohexane), aromatic hydrocarbon (e.g. benzene, toluene and xylene), acetonitrile or a suitable mixture of them.

Furthermore, the amino, hydroxyl or mercapto group as represented by X in the compounds (I), (II), (IV) or its salt can be converted into one another, as the case may be, according to a known reaction for substituent replacement on the pyrimidine ring [Supplement volume of "Tanpakushitsu/Kakusan/Kouso (Proteins/Nucleic Acids/Enzymes)", Chemical Synthesis of Nucleic Acid, Published by Kyoritsu Publishing Co. of Japan (1968)].

The method of the starting compound (III) or its salt will be described hereinafter. The starting compound (III) or its salt can be produced by, for example, the reaction steps as shown below:

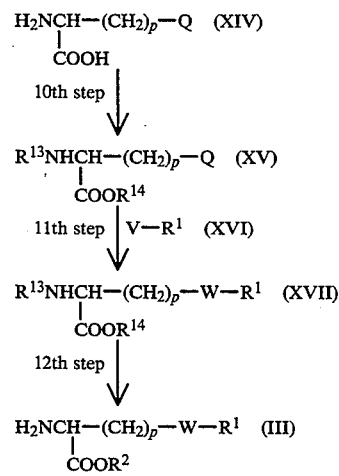

In the above reaction scheme, W, R¹, R² and p are of the same meaning as defined hereinbefore, Q and V are group capable of forming the amido-linkage W by bonding to each other. R¹³ stands for amino group and R¹⁴ stands for carboxyl group.

Tenth step:

This is the method of producing the compound (IV) or its salt after protecting the amino group and carboxyl group or the alpha-amino acid (VIV) with a per se known protective group. As the protecting group of amino group, use is made of, for example, salts with an acid (e.g. hydrochloride, sulfate, nitrate, phosphate, acetate, trifluoroacetate, p-toluenesulfonate and methanesulfonate), amides (e.g. formyl, acetyl, chloroacetyl, trichloroacetyl, trifluoroacetyl, pivaloyl, benzoyl, p-nitrobenzoyl and p-methoxybenzoyl), imides (e.g. phthaloyl and dithiosuccinoyl), carbamates (e.g. methoxycarbonyl, ethoxycarbonyl, isobutyroxycarbonyl, tert-butoxycarbonyl, cyclohexyloxycarbonyl, benzyloxycarbonyl, p-nitrobenzyloxycarbonyl and phenoxycarbonyl), benzyl group (e.g. benzyl, o-nitrobenzyl, diphenyl methyl and trityl) and silyl group (e.g. trimethyl silyl, triethyl silyl, dimethyl-tert-butyl silyl, diphenyl-tert-butyl silyl and diisopropylmethyl silyl), while, as the protecting group of carboxylic group, use is made of, for example, esters (e.g. methyl, ethyl, propyl, isopropyl, butyl, sec-butyl, isobutyl, tert-butyl, benzyl, p-nitrobenzyl and phenyl), amides (e.g. N,N-dimethyl amide, pyrrolidinylamide and piperazinyl amide), silyl esters (e.g. trimethyl silyl, triethyl silyl, dimethyl-tert-butyl silyl, diphenyl-tert-butyl silyl and diisopropylmethyl silyl), metal salts (e.g. sodium, lithium, potassium, calcium, barium, magnesium, copper and silver) and ammonium salts. This reaction can be carried out in an appropriate solvent at temperatures ranging from about 20° C. to the boiling point of the solvent, preferably 0° to 80° C., for about 10 minutes to 48 hours. Examples of the solvent to be used for the reaction include water, alcohol (e.g. methanol, ethanol and t-butanol), ether (e.g. diethyl ether, tetrahydrofuran, dioxane, monoglyme and diglyme), nitrile (e.g. acetonitrile), ester (e.g. ethyl acetate), halogenated hydrocarbon (e.g. dichloromethane, chloroform and carbon tetrachloride), aromatic hydrocarbon (e.g. benzene, toluene and xylene), pyridine, dimethylformamide, dimethyl sulfoxide or a mixture of them.

Eleventh step:

For the formation of amido-linkage of W, a known reaction is employed. In the compounds (XV), (XVI) or its salt, when Q is $NH_2$, V is carboxyl group or its reactive derivative, while, when Q is carboxyl group or its reactive derivative, V is $NH_2$. The reactive derivatives at the carboxyl group or its reactive derivatives are of the same meaning as those shown by the compound (II) or its salt. Especially, when introduction of the phthaloyl group is intended, it is advantageous to use the Nefken's reagent [Nature, 185, 309, (1960)].

Twelfth step:

The compound (XVII) or its salt obtained by the 11th step can be converted into the compound (III) or its salt by subjecting amino group thereof to a deprotection reaction according to a per se known procedure described in T. W. Green, Protective Group in Organic Synthesis, John Wiley & Sons, New York (1981). In the case where both the amino group and the carboxyl group were protected simultaneously by using the formation of copper chelate, the compound (XVII) or its salt can be converted into the compound (III) or its salt by subjecting the carboxyl group to esterification after removal of the copper by the aid of, for example, hydrogen sulfide, 6N HCl, ethylenediamine tetraacetate (EDTA) under acid conditions.

Incidentally, the reaction for formation of the amido linkage W can be conducted for the compound (XX) or its salt as well.

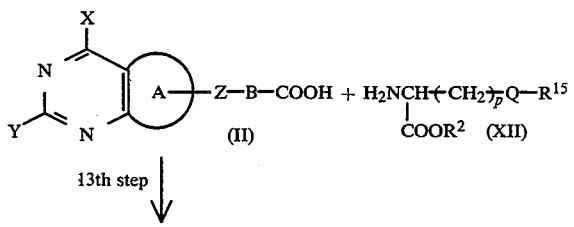

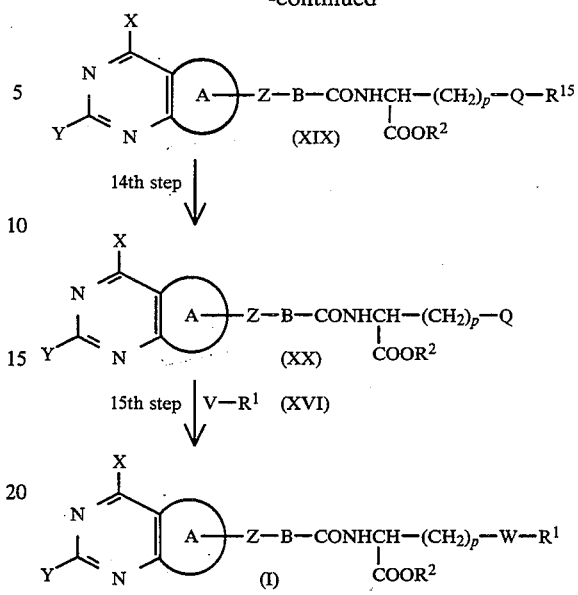

In the above formulae, X, Y, the ring A, Z, B, $R^1$, p, W, $R^2$, Q and V are of the same meaning as defined above. $R^{15}$ is a protecting group of the functional group Q, and, when Q is amino group, $R^{15}$ is, for example, carbamate (e.g. methoxycarbonyl, ethoxycarbonyl, propyloxycarbonyl, isopropyloxycarbonyl, tert-butoxycarbonyl, benzyloxycarbonyl or 9-fluorenylmethoxycarbonyl), amido (e.g. chloroacetyl), or silyl group (e.g. trimethylsilyl, triethylsilyl, dimethyl-tert-butylsilyl or diphenyl-tert-butylsilyl); while, when Q is carboxyl group, $R^{15}$ is, for example, ester (tert-butyl, benzyl, p-nitrobenzyl or 2-trimethylsilylethyl).

Thirteenth step:

The compound (XIX) or its salt can be produced by subjecting the compound (III) or its salt and the compound (XVIII) or its salt to substantially the same condensation as in the case of production of the compound (I) or its salt.

Fourteenth step:

The compound (XIX) or its salt obtained in the 13th step is subjected to the reaction for deprotection of the functional group Q, in substantially the same manner as in twelfth step to thereby produce the compound (XX) or its salt.

Fifteenth step:

The compound (XX) or its salt obtained in the 14th step is subjected to a per se known amido-forming reaction to allow the amido-bondage W through Q and V to thereby produce the compound (I) or its salt.

Incidentally stating, the reactions, reagents and reaction conditions as well as the protective group as employed upon necessity, which are carried out or employed in the 1st step through 15th step or in the step of producing the starting compound, are conducted by the known methods described in detail in the following literature references. [J. F. M. McOmine, "Protective Groups in Organic Chemistry" Plenum Press, London and New York (1973)], [Pine, Hendrickson and Hammond, "Organic Chemistry" (4th edition), [I] to [II], Hirokawa Shoten of Japan] and [M. Fieser and L.

Fieser, "Reagent for Organic Synthesis" Vol. 1 to 13, Wiley-Interscience, New York, London, Sydney and Toronto (1969-1988)].

Each of the intermediates of the compounds of this invention as well as the compound (I) or its salt of this invention produced by the methods described in the foregoing can be isolated from the reaction mixture by conventional separating means, for example, concentration, solvent extraction, chromatography and recrystallization. The resultant mixed can be used as materials in next step without separating.

Examples of salts of the compounds (I), (II), (III), (IV), (IV$_{c1}$), (IV$_{c2}$), (V), (VI), (VII), (VIII), (IX), (X), (XII), (XIII), (XIV), (XV), (XVI), (XVII), (XVIII), (XIX) and (XX) obtainable by the above production method include the salts formed with bases such as alkali metals, alkaline earth metals, non-toxic metals, ammonium or substituted ammonium, more specifically, salts with sodium, potassium, lithium, calcium, magnesium, aluminum, zinc, ammonium, trimethylammonium, triethylammonium, triethanolammonium, pyridinium and substituted pyridinium, or salts formed with acids such as mineral acids, such as hydrochloric acid, sulfuric acid, nitric acid, phosphoric acid and boric acid, and salts formed with organic acids, such as oxalic acid, tartaric acid, acetic acid, trifluoroacetic acid, methanesulfonic acid, benzenesulfonic acid, p-toluenesulfonic acid and camphorsulfonic acid.

Incidentally stating, the compounds (V), (VI), (VII), (X), (XI), (XII), (XIV), (XVI), (XVIII) or its salt can be easily produced by conventional methods or per se conventional methods.

Action

The compound (I) or its salt and their salts exhibit inhibitory effect on not less than one kind of the enzymes utilizing folic acid and its related compounds as substrate. Consequently, these compounds can be used in safety and with low toxicity either alone or in combination with any other antitumor agents for the purpose of treatment of chorio-carcinoma, leukemia, breast adenocarcinoma, capital and cervical epithelioma, squamous cell carcinoma, cellule lung cancer and lymphosarcoma that have been treated so far with MTX, as well as other various tumors resistant to MTX. The compound (I) or its salt of this invention perform excellent antitumor effects on, for example, mouse tumor cell strains (e.g. P388, L1210, L5178Y, B16 melanoma, MethA, Lewis Lung Carcinoma, S180 sarcoma, Ehrlich Carcinoma, Colon 26 and 38) and human tumor cell strains (e.g. A549, HL60 and KB), and also have actions of reducing tumors of warm blooded animals (e.g. leukemia, melanoma, sarcoma, mastocytoma and neoplasia) as well as prolonging the life span of cancer-bearing warm blooded animals.

Moreover, the compound (I) or its salt of this invention can be used in safety and with lower toxicity as a agent for antirheumatism.

Given below is description on the experimental results showing pharmacological effects of the compound (I) or its salt in the present invention.

Cell-proliferation inhibitory effects (IC$_{50}$) of the compound obtained in the first of Example 5 described hereafter against A549 cells were determined by the following method.

Each hole of a 96-hole microwell plate was inoculated with 1 ml of human lung cancer A549 cells ($5 \times 10^3$/ml) prepared by a conventional method. The plate was incubated statically for 24 hours at 37° C. in 5% $CO_2$, to which was added a 10% MEM (Nissui Seiyaku, JAPAN) solution of the said compound, and the incubation was continued for further 5 days under the same conditions as above. The culture solution was removed with a micropippete, then 0.1 ml each of a fresh 10% MEM solution (1.0 mg/ml) of MTT (Dojin Kagaku, JAPAN) was added to holes and the plate was incubated at 37° C. for 24 hours. Then 0.1 ml each of a 10% SDS (Wako Pure Chemicals Industries, Ltd., JAPAN) was added to holes and the plate was incubated at 37° C. for further 24 hours. The absorbance at the wavelength of 590 nm was determined. The concentration of the drug required for decreasing the cell number in the control group by 50% was assumed to be IC$_{50}$ value of the compound. The results were shown in Table 1.

Table 1

Test compound IC$_{50}$ ($\mu$g/ml)
1st compound of Example 5 0.0012.

As is apparent from results of the above experiment, the compound (I) or its salt show excellent inhibitory effects against cell proliferation. And, the compound (I) or its salt of this invention or their salts are less toxic and have remarkable anti-tumor activities. Therefore, preparations containing a compound (I) or its salt can be used as antitumor agent aiming at the therapy of tumors of warm-blooded animals, especially mammals (e.g. mouse, rat, cat, dog and rabbit).

The compounds (I) or its salt, when intended to use as as an antitumor agent or antirheumatism, can be administered orally or non-orally, as such or after being processed into such dosage forms as powder, granule, tablet, capsule, suppository and injectable solution by means of conventional procedures with use of pharmaceutically acceptable carriers, excipients, diluents and the like. Their dosage amount varies with the species of subject animals, type of diseases, severity of symptoms, kind of compounds or route of administration, and their daily dose for the above warm-blooded animals is about 2.0 to 200 mg/kg body weight, preferably 4.0 to 80 mg/kg body weight in terms of the compound of this invention in the case of oral administration, while the daily dose ranges from about 1.0 to 100, preferably 5-100 mg/kg in the case of non-oral administration. The method of administration for injectable solutions includes, for example, intramuscular injection, intraperitoneal injection, subcutaneous injection and intravenous injection.

The above-mentioned procedures of processing into pharmaceutical preparations are conducted in accordance with per se known methods. In manufacturing the above-mentioned oral preparations, for example, tablets, a binder (e.g. hydroxypropyl cellulose, hydroxypropyl methylcellulose or macrogol), a disintegrating agent (e.g. starch and carboxymethylcellulose calcium) and a lubricant (e.g. magnesium stearate and talc), among others, can be suitably incorporated. And, in manufacturing non-oral preparations, for example, injectable solutions, an isotonizing agent (e.g. glucose, D-sorbitol, D-mannitol and sodium chloride), a preservative (e.g. benzyl alcohol, chlorobutanol, methyl p-oxybenzoate and propyl p-oxybenzoate), and a buffer solution (e.g. phosphate buffer and sodium acetate buffer), among others, can be suitably incorporated.

With reference to a specific example of the manufacture of tablets, use is made of, for example, about 1.0 to 50 mg of a compound of this invention, 100 to 500 mg of lactose, about 50 to 100 mg of corn starch and about 5 to 20 mg of hydroxypropyl cellulose, being weighed out for use in the manufacture of one tablet, and they are mixed and tabletted to give a tablet weighing about 100 to 500 mg and measuring about 3 to 10 mm in diameter. And, the resulting tablet can furthermore be processed into an enteric coated tablet by providing coating with use of an about 5 to 10% solution of hydroxypropyl methylcellulose phthalate (about 10 to 20 mg) and castor oil (about 0.5 to 2.0 mg) in acetone-ethanol mixture. Referring to a specific example of producing injectable solutions, for example, about 2.0 to 50 mg per ampoule of sodium salt of the compound (I), (1) is dissolved in about 2 ml of physiological aqueous saline solution, and the solution is filled into an ampoule, followed by fusion and heat sterilization at about 110° C. for about 30 minutes, or (2) is dissolved in a solution of about 10 to 40 mg of mannitol or sorbitol in about 2 ml of sterilized distilled water is filled into an ampoule, followed by lyophilization and fusion to thereby prepare an injectable solution. On the occasion of using the lyophilized compound, the said ampoule is opened, and a physiological aqueous saline solution is poured into the ampoule to make a solution having a concentration of, for example 1.0 to 50 mg/ml of the compound. The solution can be used as an injectable preparation subcutaneously, intravenously or intramuscularly.

The present invention is illustrated in further detail by the following Reference Examples and Examples, which are only examples and do not limit the present invention. Modification within the scope of the present invention are permissible.

In the present specification, room temperature means 10°–35° C.

Reference Example 1

Production of methyl 4-[2-(2-amino-4-hydroxy-thieno[2,3-d]pyrimidin-5-yl)ethyl]benzoate To a solution of 2-amino-4-hydroxy-6-mercaptopyrimidine (144 mg) in dimethylformamide (DMF) was added sodium methylate (1 mmol). To the mixture was added methyl 4-(4-chloro-3-oxobutyl)benzoate (241 mg), then the reaction mixture was stirred for 12 hours at 150° C. The reaction mixture was cooled, then the solvent was distilled off under reduced pressure. The residue was purified by column chromatography on silica gel (carrier: 20 g; chloroform:methanol=50:1) to afford the title compound (94 mg; yield 29%).

$^1$H-NMR(DMSO-$d_6$) δ: 2.90–3.12(4H,m), 3.84(3H,s), 6.51(2H,s), 6.54(1H,s), 7.37(2H,d,J=8.2Hz), 7.88(2H,d,J=8.2Hz), 10.83(1H,s). IR(KBr) ν: 3460, 3100, 2930, 1720, 1680, 1605, 1490, 1405, 1280, 1180, 1105 cm$^{-1}$.

Reference Example 2

Production of 4-[2-(2-amino-4-hydroxythieno[2,3-d]pyrimidin-5-yl)ethyl]benzoic acid To a solution of methyl 4-[2-(2-amino-4-hydroxythieno [2,3-d]pyrimidin-5-yl)ethyl]benzoate (89 mg) obtained in Reference Example 1 in a mixture of tetrahydrofuran (2.7 ml)−water (0.8 ml) was added 1N aqueous solution of sodium hydroxide (1 ml). The mixture was stirred for 20 hours at room temperature. Tetrahydrofuran was distilled off from the reaction mixture, then the residue was neutralized with 1N HCl. Resulting precipitate was collected by filtration, and washed with water, methanol and ether to afford the title compound (69 mg; yield 81%).

$^1$H-NMR(DMSO-$d_6$) δ: 2.90–3.12(4H,m), 6.54(1H,s), 6.65(2H,s), 7.34(2H,d,J=8.2Hz), 7.86(2H,d,J=8.2Hz), 10.59(1H,s). IR(KBr) ν: 3430, 3120, 2920, 1700, 1670, 1650, 1610, 1480, 1360, 1310, 1280, 1175 cm$^{-1}$.

Reference Example 3

Production of methyl 4-[2-(2,4-diaminothieno[2,3-d]pyrimidin-5-yl)ethyl]benzoate In substantially the same manner as in Reference Example 1, the title compound (260 mg, yield 16%) was obtained from 2,4,6-triaminopyrimidine (957 mg) and methyl 4-(4-chloro-3-oxobutyl)benzoate (1.21 g).

$^1$H-NMR(DMSO-$d_6$) δ: 3.00(2H,t,J=8.0Hz), 3.16(2H,t,J=8.0Hz), 3.84(3H,s), 6.01(2H,s), 6.44(2H,s), 6.49(1H,s), 7.39(2H,d,J=8.2Hz), 7.87(2H,d,J=8.2Hz). IR(KBr) ν: 3450, 3300, 3100, 2950, 1720, 1650, 1635, 1610, 1550, 1505, 1435, 1280, 1180, 1110 cm$^{-1}$.

Reference Example 4

Production of 4-[2-(2,4-diaminothieno[2,3-d]pyrimidin-5-yl)ethyl]benzoic acid

In substantially the same manner as in Reference Example 2, methyl 4-[2-(2,4-diaminothieno[2,3-d]pyrimidin-5-ylethyl]benzoate (240 mg) obtained in Reference Example 3 was subjected to alkali hydrolysis to afford the title compound (201 mg; yield 88%).

$^1$H-NMR(DMSO-$d_6$) δ: 3.02(2H,t,J=8.0Hz), 3.14(2H,t,J=8.0Hz), 6.07(2H,s), 6.47(2H,s), 6.51(1H,s), 7.35(2H,d,J=8.2Hz), 7.84(2H,d,J=8.2Hz). IR(KBr) ν: 3400, 3340, 3180, 2930, 1660, 1620, 1610, 1560, 1510, 1450, 1375, 1280, 1175, 1100 cm$^{-1}$.

Reference Example 5

Production of methyl 4-[2-(2,4-diaminofuro[2,3-d]pyrimidin-5-yl)ethyl]benzoate

To a solution of 2,6-diamino-4-hydroxypyrimidine (631 mg) in dimethylformamide (10 ml) was added methyl 4-(4-chloro-3-oxobutyl)benzoate (1.21 g), and the mixture was stirred for 36 hours at 50° C. The solvent was distilled off under reduced pressure. The residue was purified by column chromatography on silica gel (carrier: 70 g; chloroform:methanol=30:1) to afford the title compound (192 mg; yield 12%)

$^1$H-NMR(DMSO-$d_6$) δ: 2.96(4H,s), 3.84(3H,s), 5.98(2H,s), 6.46(2H,s), 7.05(1H,s), 7.41(2H,d,J=8.2Hz), 7.88(2H,d,J=8.2Hz). IR(KBr) ν: 3480, 3410, 3340, 3140, 1715, 1660, 1630, 1610, 1580, 1490, 1460, 1435, 1375, 1310, 1280, 1180, 1110, 1060 cm$^{-1}$.

Reference Example 6

Production of 4-[2-(2,4-diaminofuro[2,3-d]pyrimidin-5-yl)ethyl]benzoic acid

In substantially the same manner as in Reference Example 2, methyl 4-[2-(2,4-diaminofuro[2,3-d]pyrimidin-5-yl)ethyl]benzoate (157 mg) obtained in Reference Example 5 was subjected to alkali hydrolysis to afford the title compound (119 mg; yield 80%).

$^1$H-NMR(DMSO-$d_6$) δ: 2.96(4H,s), 6.15(2H,s), 6.64(2H,s), 7.09(1H,s), 7.38(2H,d,J=8.2Hz), 7.86(2H,d,J=8.2Hz). IR(KBr) ν: 3490, 3420, 3380, 3140, 2930, 1670, 1630, 1610, 1595, 1580, 1460, 1415, 1390, 1315, 1270, 1170, 1065 cm$^{-1}$.

Example 1

Production of N(α)-[4-[3-(2,4-diamino-7H-pyrrolo [2,3-d]pyrimidin-5-yl)propyl]benzoyl]-N-(δ)-phthaloyl-L-ornithine methylester To a suspension of 4-[3-(2,4-diamino-7H-pyrrolo[2,3-d]pyrimidin-5-yl)propyl]benzoic acid (350 mg) and N(δ)-phthaloyl-L-ornithine methylester hydrochloride (420 mg) in dimethylformamide (DMF) (30 ml) was added dropwise diethyl cyanophosphate (220 mg) under ice-cooling. The mixture was stirred for 10 minutes, to which was added dropwise slowly triethylamine (390 mg), followed by stirring for 4 hours at room temperature. The solvent was distilled off under reduced pressure, and the residue was purified by column chromatography on silica gel (carrier: 14 g; chloroform:ethanol containing 1% ammonia=20:1–10:1) to afford the title compound (477 mg; yield 74%).

$^1$H-NMR(CDCl$_3$) δ: 1.70–2.10(6H,m), 2.50–2.75(4H,m), 3.72(2H,m), 3.76(3H,s), 4.60(2H,brs), 4.83(1H,m), 5.10(2H,brs), 6.45(1H,s), 6.91(1H,d,J=8.0Hz), 7.17(2H,d,J=8.0Hz), 7.60–7.85(6H,m), 9.13(1H,brs). IR(KBr) ν: 3390, 1735, 1710, 1610 cm$^{-1}$.

Example 2

In substantially the same manner as in Working Example 1, carboxylic acid (II) (1 mmol) was condensed with amino acid (III) (1.1 mmol) in dimethylformamide with the aid of diethyl cyanophosphate to synthesize the following compounds.

(1) N(α)-[4-[2-(2,4-diamino-7H-pyrrolo[2,3-d]pyrimidin-5-yl)ethyl]benzoyl]-N(δ)-phthaloyl-L-ornithine methylester $^1$H-NMR(CDCl$_3$) δ: 1.70–2.10(4H,m), 3.01(4H,brs), 3.74(2H,m), 3.78(3H,s), 4.70(2H,brs), 4.88(1H,m), 5.08(2H,brs), 6.41(1H,s), 6.80(1H,d,J=7.0Hz), 7.22(2H,d,J=8.2Hz), 7.65–7.80(4H,m), 7.84(2H,dd,J=5.4, 3.2Hz), 8.25(1H,brs). IR(KBr) ν: 3370, 1735, 1710, 1610 cm$^{-1}$.

(2) N(α)-[4-[3-(2,4-diamino-7H-pyrrolo[2,3-d]pyrimidin-5-yl)propyl]benzoyl]-N(ε)-phthaloyl-L-lysine methylester $^1$H-NMR(CDCl$_3$) δ: 1.20–1.80(4H,m), 1.90–2.10(4H,m), 2.60–2.80(4H,m), 3.70(2H,m), 3.78(3H,s), 4.57(2H,brs), 4.81(1H,m), 4.88(2H, brs), 6.50(1H,s), 6.80(1H,d,J=8.0Hz), 7.27(2H,d,J=8.2Hz), 7.65–7.85(6H,m), 8.25(1H,brs). IR(KBr) ν: 3370, 2930, 1740, 1710, 1610, 1575, 1400 cm$^{-1}$.

(3) Methyl 2(s)-[4-[3-(2,4-diamino-7H-pyrrolo[2,3-d]pyrimidin-5-yl)propyl]benzoyl]amino-4-phthaloylamino-butyrate $^1$H-NMR(CDCl$_3$) δ: 2.00(2H,m), 2.40(2H,m), 2.65(2H,t,J=7.8Hz), 2.76(2H,t,J=7.2Hz), 3.54(3H,s), 3.87(2H,m), 4.63(2H,brs), 4.85–5.00(3H,m), 6.49(1H,s), 7.27(2H,d,J=8:2Hz), 7.45(1H,d,J=8.2Hz), 7.72(2H,dd,J=5.6, 3.2Hz), 7.85(2H,dd,J=5.6, 3.2Hz), 7.86(2H,d,J=8.2Hz), 8.54(1H,brs). IR(KBr) ν: 3380, 2970, 1740, 1710, 1610, 1570, 1540, 1435, 1395, 720 cm$^{-1}$.

(4) N(α)-[4-[N-[2-(2,4-diamino-7H-pyrrolo[2,3-d]pyrimidin-5-yl)ethyl]-N-methyl]aminobenzoyl]-N-(δ)-phthaloyl-L-orithine methylester $^1$H-NMR(CDCl$_3$/CD$_3$OD) δ: 1.70–2.10(4H,m), 2.92(3H,s), 2.95(2H,t,J=7.0Hz), 3.70–3.80(3H,m), 3.78(3H,s), 4.78(1H,m), 6.48(1H,s), 6.72(2H,d,J=8.8Hz), 7.60–7.90(6H,m). IR(KBr) ν: 3380, 1735, 1710, 1635, 1600 cm$^{-1}$.

(5) N(α)-[3-chloro-4-[3-(2,4-diamino-7H-pyrrolo[2,3-d]pyrimidin-5-yl)propyl]benzoyl]-N(δ)-L-ornithine methylester $^1$H-NMR(CDCl$_3$) δ: 1.70–2.10(6H,m), 2.50–2.75(4H,m), 3.73(2H,m), 3.78(3H,s), 4.62(2H,brs), 4.85(1H,m), 5.11(2H,brs), 6.44(1H,s), 6.91(1H,d,J=8.0Hz), 7.38(1H,d,J=8.0Hz), 7.60–7.90(6H,m), 9.13(1H,brs). IR(KBr) ν: 3380, 1735, 1710, 1610 cm$^{-1}$.

(6) N(α)-[5-[3-(2,4-diamino-7H-pyrrolo[2,3-d]pyrimidin-5-yl)propyl]-2-thenoyl]-N-(δ)-phthaloyl-L-ornithine methylester $^1$H-NMR(CDCl$_3$/CD$_3$OD) δ: 1.70–2.10(6H,m), 2.71(2H,m), 2.91(2H,m), 3.73(2H,m), 3.76(3H,s), 4.77(1H,m), 6.47(1H,s), 6.79(1H,d,J=3.6Hz), 7.43(1H,d,J=3.6Hz), 7.60–7.90(4H,m). IR(KBr) ν: 3380, 2980, 1735, 1710, 1635, 1610, 1575, 1545, 1380 cm$^{-1}$.

(7) N(α)-[5-[N-(tert-butoxycarbonyl)-N-[2-(2,4-diamino-7H-pyrrolo[2,3-d]pyrimidin-5-yl)ethyl]amino]-2-thenoyl]-N(δ)-phthaloyl-L-ornithine methylester $^1$H-NMR(CDCl$_3$/CD$_3$OD) δ: 1.51(9H,s), 1.70–2.10(4H,m), 3.02(2H,t,J=7.8Hz), 3.73(2H,m), 3.76(3H,s), 3.80–4.00(2H,m), 4.73(1H,m), 6.53(1H,s), 6.63(1H,d,J=4.2Hz), 7.39(1H,d,J=4.2 Hz), 7.60–7.90(4H,m). IR(KBr) ν: 3370, 2980, 1735, 1700, 1635, 1610, 1575, 1550, 1395 cm$^{-1}$.

(8) N(α)-[4-[2-(2,4-diaminofuro[2,3-d]pyrimidin-5-yl)ethyl]benzoyl]-N(δ)-phthaloyl-n-ornithine methylester $^1$H-NMR(DMSO-d$_6$) δ: 1.60–1.90(4H,m), 2.95(4H,brs), 3.60(2H,m), 3.62(3H,s), 4.44(1H,m), 6.08(2H,brs), 6.59(2H,brs), 7.07(1H,s), 7.35(2H,d,J=8.2Hz), 7.81(2H,d,J=8.2Hz), 7.85(4H,m), 8.61(1H,d,J=7.6Hz). IR(KBr) ν: 3370, 1740, 1710, 1630, 1570, 1540, 1395 cm$^{-1}$.

(9) N(α)-[4-[2-(2,4-diaminothieno[2,3-d]pyrimidin-5-yl)ethyl]benzoyl]-N(δ)-phthaloyl-L-ornithine methylester $^1$H-NMR(DMSO-d$_6$) δ: 1.60–1.90(4H,m), 3.00(2H,m), 3.16(2H,m), 3.60(2H,m), 3.62(3H,s), 4.41(1H,m), 6.05(2H,brs), 6.42(2H,brs), 6.50(1H,s), 7.35(2H,d,J=8.2Hz), 7.80(2H,d,J=8.2Hz), 7.84(4H,m), 8.62(1H,d,J=7.6Hz). IR(KBr) ν: 3450, 3400, 3320, 1740, 1710, 1640, 1560, 1200 cm$^{-1}$.

(10) N(α)-[4-[2-(2-amino-4-hydroxy-7H-pyrrolo[2,3-d]pyrimidin-5-yl)ethyl]benzoyl]-N(δ)-phthaloyl-L-ornithine methylester $^1$H-NMR(DMSO-d$_6$) δ: 1.60–1.90(4H,m), 2.80–3.00(4H,m), 3.62(3H,s), 3.63(2H,m), 4.44(1H,m), 5.99(2H,brs), 6.30(1H,d,J=1.8Hz), 7.27(2H,d,J=8.2Hz), 7.74(2H,d,J=8.2Hz), 7.85(4H,m), 8.61(1H,d,J=7.6Hz), 10.13(1H,brs), 10.59(1H,brs). IR(KBr) ν: 3360, 1740, 1710, 1660, 1630, 1540, 1530, 1395, 710 cm$^{-1}$.

(11) N(α)-[4-[2-(2-amino-4-hydroxythieno[2,3-d]pyrimidin-5-yl)ethyl]benzoyl]-N(δ)-phthaloyl-L-ornithine methylester $^1$H-NMR(DMSO-d$_6$) δ: 1.60–1.90(4H,m), 3.03(2H,m), 3.13(2H,m), 3.62(3H,s), 3.63(2H,m), 4.65(1H,m), 5.90(2H,brs), 6.38(1H,s), 7.27(2H,d,J=8.2Hz), 7.74(2H,d,J=8.2Hz), 7.85(4H,m), 8.62(1H,d,7.6Hz), 10.76(1H,brs). IR(KBr) ν: 3450, 3320, 1740, 1710, 1670, 1635, 1600, 1535 cm$^{-1}$.

Example 3

Production of N(α)-[4-[3-(2,4-diamino-7H-pyrrolo[2,3-d]pyrimidin-5-yl)propyl]benzoyl]-N(δ)-(o-pyrrolidinocarbonylbenzoyl)-L-ornithine methylester To a solution of N(α)-[4-[3-(2,4-diamino-7H-pyrrolo[2,3-d]pyrimidin-5-yl)propyl]benzoyl]-N(δ)-phthaloyl-L-ornithine methylester (70 mg) in tetrahydrofuran (THF) (1 ml) was added pyrrolidine (20 mg), and the mixture was stirred for 10 hours at room temperature.

The solvent was distilled off under reduced pressure, and the residue was purified by means of column chromatography on silica gel (carrier: 8 g; chloroform:ethanol containing 1% ammonia=10:1) to afford the title compound (61 mg, yield 77%).

$^1$H-NMR(CDCl$_3$) δ: 1.60-2.10(10H,m), 2.63(2H,t,J=7.2Hz), 2.73(2H,t,J=7.0Hz), 3.15(2H,t,J=6.4Hz), 3.43(2H,m), 3.58(2H,t,J=6.8Hz), 3.77(3H,s), 4.70(2H,brs), 4.79(1H,m), 4.93(2H,brs), 6.45(1H,s), 7.22(2H,d,J=8.2Hz), 7.20-7.30(2H,m), 7.40-7.50(3H,m), 7.74(1H,m), 7.81(2H,d,J=8.2Hz), 8.53(1H,brs). IR(KBr) ν: 3330, 1735, 1610, 1570, 1540, 1490, 1450, 1430 cm$^{-1}$.

Example 4

Production of N(α)-[4-[3-(2,4-diamino-7H-pyrrolo[2,3-d]pyrimidin-5-yl)propyl]benzoyl]-N(δ)-hemiphthaloyl-L-ornithine To a solution of N(α)-[4-[3-(2,4-diamino-7H-pyrrolo[2,3-d]pyrimidin-5-yl)propyl]benzoyl]-N(δ)-phthaloyl-L-ornithine methylester (70 mg) in a mixture of methanol (1 ml) and tetrahydrofuran (THF) (0.5 ml) was added, under ice-cooling, 1N aqueous solution of sodium hydroxide (1 ml), and the mixture was stirred for three hours at room temperature. The organic solvent was distilled off under reduced pressure. The residue was subjected to filtration with a membrane filter. The filtrate was neutralized with 1N HCl to cause precipitation of crystals. The crystals were collected by filtration, washed with water and dried to afford the title compound (61 mg; yield 87%).

$^1$H-NMR(DMSO-d$_6$) δ: 1.60(2H,m), 1.83(4H,m), 2.50-2.75(4H,m), 3.30(2H,m), 4.37(1H,m), 5.60(2H,brs), 6.21(2H,brs), 6.47(1H,s), 7.29(2H,d,J=8.2Hz), 7.30-7.55(3H,m), 7.73(1H,dd,J=7.0, 1.8Hz), 7.82(2H,d,J=8.2Hz), 8.32(1H,m), 8.48(1H,d,J=8.2Hz), 10.54(1H,brs). IR(KBr) ν: 3330, 3200, 1660, 1640, 1540 cm$^{-1}$.

Example 5

By substantially the same manner as in Working Example 4, methyl ester of carboxylic acid (0.2 mmol) produced in Working Example 2 was subjected to alkali hydrolysis to synthesize the following compounds.

(1) N(α)-[4-[2-(2,4-diamino-7H-pyrrolo[2,3-d]pyrimidin-5-yl)ethyl]benzoyl]-N(δ)-hemiphthaloyl-L-ornithine $^1$H-NMR (DMSO-d$_6$) δ: 1.50-2.00(4H,m), 2.95(4H,m), 3.21(2H,m), 4.40(1H,m), 5.62(2H,brs), 6.26(2H,brs), 6.40(1H,s), 7.31(2H,d,J=8.2Hz), 7.35-7.55(3H,m), 7.73(1H,dd,J=7.0, 1.8Hz), 7.81(2H,d,J=8.2Hz), 8.31(1H,t,J=8.2Hz), 8.46(1H,d,J=7.6Hz), 10.50(1H,brs). IR(KBr) ν: 3330, 3200, 2920, 1640, 1545 cm$^{-1}$.

(2) N(α)-[4-[3-(2,4-diamino-7H-pyrrolo[2,3-d]pyrimidin-5-yl)propyl]benzoyl]-N(ε)-hemiphthaloyl-L-lysine $^1$H-NMR(DMSO-d$_6$) δ: 1.35-1.60(4H,m), 1.70-1.95(4H,m), 2.60-2.80(4H,m), 3.20(2H,m), 4.35(1H,m), 5.50(2H,brs), 6.08(2H,brs), 6.45(1H,s), 7.27(2H,d,J=8.2Hz), 7.36(1H,m), 7.46(2H,m), 7.73(1H,dd,J=7.0, 2.6Hz), 7.80(2H,d,J=8.2Hz), 8.34(1H,m), 8.44(1H,d,J=7.6Hz), 10.47(1H,brs). IR(KBr) ν: 3330, 3200, 2930, 1640, 1540, 1380 cm$^{-1}$.

(3) N(α)-[4-[N-[2-(2,4-diamino-7H-pyrrolo[2,3-d]pyrimidin-5-yl)ethyl]-N-methyl]aminobenzoyl]-N(δ)hemiphthaloyl-L-ornithine $^1$H-NMR(DMSO-d$_6$) δ: 1.50-2.00(4H,m), 2.89(2H,t,J=7.0Hz), 2.92(3H,s), 3.21(2H,m), 3.60(2H,t,J=7.0Hz), 4.40(1H,m), 5.51(2H,brs), 6.13(2H,brs), 6.43(1H,s), 6.72(2H,d,J=8.8Hz), 7.35-7.55(3H,m), 7.73(1H,m), 7.74(2H,d,J=8.8Hz), 8.31(1H,t,J=8.2Hz), 8.37(1H,d,J=7.6Hz), 10.53(1H,brs). IR(KBr) ν: 3330, 3200, 2930, 1670, 1640, 1545, 1380, 1200 cm$^{-1}$.

(4) N(α)-[3-chloro-4-[3-(2,3-diamino-7H-pyrrolo[2,3-d]pyrimidin-5-yl)propyl]benzoyl]-N(δ)-hemiphthaloyl-L-ornithine $^1$H-NMR(DMSO-d$_6$) δ: 1.60(2H,m), 1.83(4H,m), 2.50-2.75(4H,m), 3.30(2H,m), 4.37(1H,m), 5.63(2H,brs), 6.20(2H,brs), 6.46(1H,s), 7.30-7.55(4H,m), 7.70-7.80(2H,m), 7.93(1H,d,J=1.8Hz), 8.32(1H,m), 8.48(1H,d,J=8.2Hz), 10.54(1H,brs). IR(KBr) ν: 3330, 3200, 1660, 1640, 1540 cm$^{-1}$.

(5) N(α)-[5-[3-(2,4-diamino-7H-pyrrolo[2,3-d]pyrimidin-5-yl)propyl]-2-thenoyl]-N(δ)-hemiphthaloyl-L-ornithine $^1$H-NMR (DMSO-d$_6$) δ: 1.60-2.10(6H,m), 2.71(2H,m), 2.85(2H,m), 3.30(2H,m), 4.37(1H,m), 5.57(2H,brs), 6.17(2H,brs), 6.47(1H,s), 6.88(1H,d,J=3.6Hz), 7.30-7.55(3H,m), 7.68(1H,d,J=3.6Hz), 7.75(1H,m), 8.32(1H,m), 8.48(1H,d,J=8.2Hz), 10.49(1H,brs). IR(KBr) ν: 3340, 3200, 1680, 1660, 1610, 1540, 1455, 1400, 1300 cm$^{-1}$.

(6) N(α)-[5-[N-(tert-butoxycarbonyl)-N-[2-(2,4-diamino-7H-pyrrolo[2,3-d]pyrimidin-5-yl)ethyl]amino]-2-thenoyl]-N(δ)-hemiphthaloyl-L-ornithine $^1$H-NMR(DMSO-d$_6$) δ: 1.04(9H,s), 1.60-2.10(4H,m), 2.95(2H,m), 3.30(2H,m), 4.10(2H,m), 4.30(1H,m), 5.55(2H,brs), 6.15(2H,brs), 6.45(1H,s), 6.72(1H,d,J=4.2Hz), 7.30-7.55(4H,m), 7.75(1H,m), 8.32(1H,m), 8.48(1H,d,J=8.2Hz), 10.53(1H,brs). IR(KBr) ν: 3370, 3200, 2970, 1695, 1660, 1610, 1580, 1455, 1400, 1300 cm$^1$.

(7) N(α)-[5-[N-[2-(2,4-diamino-7H-pyrrolo[2,3-d]pyrimidin-5-yl)ethyl]amino]-2-thenoyl]-N(δ)-hemiphthaloyl-L-ornithine $^1$H-NMR(DMSO-d$_6$/D$_2$O) δ: 1.60-2.10(4H,m), 2.93(2H,t,J=6.6Hz), 3.24(2H,t,J=6.6Hz), 3.60(2H,m), 4.30(1H,m), 5.85(1H,d,J=4.0Hz), 6.50(1H,s), 7.30-7.55(4H,m), 7.75(1H,m). IR(KBr) ν: 3340, 2940, 1660, 1610, 1550, 1455, 1400, 1300 cm$^{-1}$.

(8) N(α)-[4-[2-(2,4-diaminofuro[2,3-d]pyrimidin-5-yl)ethyl]benzoyl]-N(δ)-hemiphthaloyl-L-ornithine $^1$H-NMR(DMSO-d$_6$) δ: 1.60-1.90(4H,m), 2.95(4H,brs), 3.60(2H,m), 4.40(1H,m), 6.08(2H,brs), 6.57(2H,brs), 7.08(1H,s), 7.35(2H,d,J=8.2Hz), 7.35-7.60(3H,m), 7.75(1H,m), 7.81(2H,d,J=8.2Hz), 8.30(1H,m), 8.61(1H,d,J=7.6Hz). IR(KBr) ν: 3330, 1630, 1570, 1540, 1395 cm$^{-1}$.

(9) N(α)-[4-[2-(2,4-diaminothieno[2,3-d]pyrimidin-5-yl)ethyl]benzoyl]-N(δ)-hemiphthaloyl-L-ornithine $^1$H-NMR(DMSO-d$_6$) δ: 1.60-1.90(4H,m), 3.00(2H,m), 3.15(2H,m), 3.60(2H,m), 3.63(3H,m), 4.41(1H,m), 6.13(2H,brs), 6.52(1H,s), 6.55(2H,brs), 7.35(2H,d,J=8.2Hz), 7.35-7.60(3H,m), 7.75(1H,m), 7.80(2H,d,J=8.2Hz), 8.31(1H,m), 8.62(1H,d,J=7.6Hz). IR(KBr) ν: 3340, 1630, 1570, 1550 cm$^{-1}$.

(10) N(α)-[4-[2-(2-amino-4-hydroxy-7H-pyrrolo[2,3-d]pyrimidin-5-yl)ethyl]benzoyl]-N(δ)-hemiphthaloyl-L-ornithine $^1$H-NMR(DMSO-d$_6$) δ: 1.50-2.00(4H,m), 2.85(2H,m), 2.98(2H,m), 3.30(2H,m), 4.37(1H,m), 5.99(2H,brs), 6.29(1H,d,J=1.8Hz), 7.28(2H,d,J=8.2Hz), 7.39(1H,dd,J=6.8, 1.6Hz), 7.40-7.60(2H,m), 7.74(1H,dd,J=7.2, 1.6Hz), 7.79(2H,d,J=8.2Hz), 8.28(1H,t,J=5.4Hz), 8.48(1H,d,J=7.8Hz), 10.13(1H,brs), 10.59(1H,brs). IR(KBr) ν: 3340, 3200, 1690, 1640 cm$^{-1}$.

(11) N(α)-[4-[2-(2-amino-4-hydroxythieno[2,3-d]pyrimidin-5-yl)ethyl]benzoyl]-N(δ)-hemiphthaloyl-L-ornithine $^1$H-NMR(DMSO-d$_6$) δ: 1.50–2.00(4H,m), 2.90–3.10(4H,m), 3.30(2H,m), 4.39(1H,m), 6.53(2H,brs), 6.55(1H,s), 7.32(2H,d,J=8.2Hz), 7.37(1H,dd,J=6.8, 1.6 Hz), 7.40–7.60(2H,m), 7.75(1H,dd,J=7.2, 1.6Hz), 7.81(2H,d,J=8.2Hz), 8.30(1H,t,J=5.4Hz), 8.51(1H,d,J=7.8Hz), 10.85(1H,brs). IR(KBr) ν: 3340, 3200, 1690, 1640, 1540, 1505 cm$^{-1}$.

(12) 2(s)-[4-[3-(2,4-diamino-7H-pyrrolo[2,3-d]pyrimidin-5yl) propyl]benzoylamino]-4-hemiphthaloylaminobutyric acid $^1$H-NMR (DMSO-d$_6$) δ: 1.75–2.20(4H,m), 2.70(4H,m), 3.28(2H,m), 4.49(1H,m), 5.84(2H,brs), 6.41(2H,brs), 6.51(1H,s), 7.29(2H,d,J=8.2Hz), 7.30–7.55(3H,m), 7.76(1H,dd,J=7.0, 1.8Hz), 7.81(2H,d,J=8.2Hz), 8.30(1H,m), 8.53(1H,d,J=7.2Hz), 10.68(1H,brs). IR(KBr) ν: 3325, 3200, 2930, 1640, 1545, 1535, 1500, 1380 cm$^{-1}$.

Example 6

Production of methyl N(α)-[4-[3-(2,4-diamino-7H-pyrrolo[2,3-d]pyrimidin-5-yl)propyl]benzoyl]-N-(3-borophenyl)-L-glutaminate To a DMF solution of 4-[3-(2,4-diamino-7H-pyrrolo[2,3-d]pyrimidin-5-yl)propyl]benzoic acid (700 mg) and methyl N-(3-borophenyl)-L-glutaminate hydrochloride (720 mg) were added diethyl cyanophosphate (560 ml) and triethylamine (910 mg). The mixture was stirred for 2 hours at room temperature. The reaction mixture was concentrated under reduced pressure, then the concentrate was washed with water, followed by purification by column chromatography on silica gel (carrier: 5 g; chloroform:methanol=10:1) to afford the subject compound (1.03 g; yield 80%).

$^1$H-NMR(DMSO-d$_6$) δ: 1.75–2.30(4H,m), 2.46(2H,m), 2.50(2H,m), 2.71(2H,m), 3.67(3H,s), 4.47(1H,m), 5.39(2H,brs), 5.96(2H,brs), 6.43(1H,s), 7.24(1H,t,J=8.2Hz), 7.31(2H,d,J=8.2Hz), 7.69(1H,d,J=7.4Hz), 7.81(1H,s), 7.83(2H,d,J=8.2Hz), 7.98(2H,s), 8.71(1H,d,J=7.4Hz), 9.85(1H,d,J=4.4Hz), 10.41(1 H,brs). IR (KBr) ν: 3340, 2950, 1735, 1665, 1645, 1610, 1545, 1430, 1200, 720 cm$^{-1}$.

Example 7

In substantially the same manner as in Example 6, carboxylic acid (1 mmol.) and methyl N-substituted-L-glutaminate hydrochloride (1.1 mmol.) were subjected to condensation using diethyl cyanophosphate (1.5 mmol.) in DMF in the presence of triethylamine (4 mmol.) to synthesize the following compounds:

(1) Methyl N(α)-[4-[2-(2,4-diamino-7H-pyrrolo[2,3-d]pyrimidin-5-yl)ethyl]benzoyl]-N-(3-borophenyl)-L-glutaminate $^1$H-NMR (CD$_3$OD) δ: 2.10–2.45(2H,m), 2.56(2H,m), 3.03(4H,m), 3.75(3H,s), 4.66(1H,dd,J=9.0Hz, 5.0Hz), 6.46(1H,s), 7.20–7.30(3H,m), 7.38(1H,m), 7.53(1H,m), 7.73(1H,brs), 7.75(2H,d,J=8.2Hz)

(2) Methyl N(α)-[4-[2-(2,4-diamino-7H-pyrrolo[2,3-d]pyrimidin-5-yl)ethyl]benzoyl]-N-(3-ethoxycarbonylphenyl)-L-glutaminate $^1$H-NMR(DMSO-d$_6$) δ: 1.32(3H,t,J=7.2Hz), 1.8–2.37(2H,m), 2.46(2H,m), 2.96(4H,m), 3.66(3H,s), 4.30(2H,q,J=7.2Hz), 4.49(1H,m), 5.37(2H,brs), 5.99(2H,brs), 6.35(1H,d,J=2.0Hz), 7.33(2H,d,J=8.2Hz), 7.43(1H,t,J=8.0Hz), 7.62(1H,dt,J=8.0Hz, 1.4Hz), 7.81(2H,d,J=8.2Hz), 7.83(1H,dd,J=8.0Hz, 1.4 Hz), 8.23(1H,t,J=1.4Hz), 8.71(1H,d,J=7.2Hz), 10.16(1H,s), 10.35(1H,d,J=2.0Hz). IR(KBr) ν: 3470, 3380, 3200, 2990, 2960, 2940, 2850, 1720, 1610, 1580, 1555, 1490, 1435, 1370, 1290, 1175, 1105, 1085, 1020, 760, 685, 600, 550 cm$^{-1}$.

(3) Methyl N(α)-[4-[2-(2,4-diamino-7H-pyrrolo[2,3-d]pyrimidin-5-yl)ethyl]benzoyl]-N-(4-ethoxycarbonylphenyl)-L-glutaminate $^1$H-NMR(DMSO-d$_6$) δ: 1.31(3H,t,J=7.0Hz), 1.8–2.35(2H,m), 2.50(2H,t,J=5.6Hz), 2.97(4H,m), 3.66(3H,s), 4.28(2H,q,J=7.0Hz), 4.48(1H,m), 5.37(2H,brs), 5.99(2H,brs), 6.36(1H,s), 7.34(2H,d,J=8.2Hz), 7.71(2H,d,J=8.8Hz), 7.81(2H,d,J=8.2Hz), 7.90(2H,d,J=8.8Hz), 8.72(1H,d,J=7.6Hz), 10.28(1H,s), 10.37(1H,brs). IR(KBr) ν: 3375, 3180, 2975, 2920, 2850, 1735, 1700, 1605, 1575, 1535, 1500, 1420, 1405, 1365, 1305, 1275, 1250, 1215, 1175, 1105, 1020, 855, 770, 750 cm$^{-1}$.

(4) Methyl N(α)-[4-[2-(2,4-diamino-7H-pyrrolo[2,3-d]pyrimidin-5-yl)ethyl]benzoyl]-N-(3-hydroxyphenyl)-L-glutaminate $^1$H-NMR (DMSO-d$_6$) δ: 1.8–2.3(2H,m), 2.46(2H,t,J=7.4Hz), 2.98(4H,m), 3.66(3H,s), 4.46(1H,m), 6.42(1H,d,J=6.8Hz), 6.47(2H, brs), 6.53(1H,s), 6.93(1H,d,J=6.8Hz), 7.00(1H,t,J=6.8Hz), 7.10(2H,brs), 7.17(1H,s), 7.34(1H,d,J=8.2Hz), 7.83(2H,d,J=8.2Hz), 8.72(1H,d,J=7.0Hz), 9.35(1H,s), 9.82(1H,s), 11.04(1H,brs).

(5) Methyl N(α)-[4-[2-(2,4-diamino-7H-pyrrolo[2,3-d]pyrimidin-5-yl)ethyl]benzoyl]-N-(4-hydroxyphenyl)-L-glutaminate $^1$H-NMR(DMSO-d$_6$) δ: 1.9–2.3(2H,m), 2.41(2H,t,J=7.4Hz), 2.96(4H,m), 3.65(3H,s), 4.46(1H,m), 5.38(2H,brs), 6.00(2H,brs), 6.40(2H,d,J=1.0Hz), 6.69(2H,d,J=8.8 Hz), 7.34(2H,d,J=8.8Hz), 7.813(2H,d,J=8.0Hz), 8.72(1H,d,J=7.8Hz), 9.14(1H,s), 9.67(1H,s), 10.36(1H,s). IR(KBr) ν: 3475, 3380, 3310, 2950, 2925, 2910, 2850, 1740, 1640, 1615, 1585, 1545, 1515, 1500, 1440, 1405, 1380, 1340, 1305, 1255, 1240, 1160, 1105, 1090, 1005, 950, 825, 790, 735, 690, 635, 520 cm$^{-1}$.

(6) Methyl N(α)-[4-[2-(2,4-diamino-7H-pyrrolo[2,3-d]pyrimidin-5-yl)ethyl]benzoyl]-N-[3-(1H-tetrazol-5-yl)phenyl]-L-glutaminate $^1$H-NMR(DMSO-d$_6$) δ: 1.90–2.35(2H,m), 2.50(2H,m), 2.94(4H,m), 3.65(3H,s), 4.48(1H,m), 5.82(2H,brs), 6.43(1H,s), 6.48(2H,brs), 7.34(2H,d,J=8.0Hz), 7.36(1H,t,J=8.0Hz), 7.66(1H,d,J=8.0Hz), 7.83(2H,d,J=8.0Hz), 8.22(1H,s), 8.74(1H,d,J=7.4Hz), 10.08(1H,s), 10.65(1H,s). IR(KBr) ν: 3400, 3200, 2930, 2850, 1735, 1640, 1610, 1570, 1545, 1500, 1470, 1430, 1415, 1380, 1345, 1315, 1295, 1270, 1210, 1090, 1055, 1030, 800, 755, 690 cm$^{-1}$.

(7) Ethyl N-[N(α)-[4-[2-(2,4-diamino-7H-pyrrolo[2,3-d]pyrimidin-5-yl)ethyl]benzoylamino]-4(S)-methoxycarbonylbutyryl]-glycinate $^1$H-NMR(DMSO-d$_6$) δ: 1.18(3H,t,J=7.2Hz), 1.8–2.2(2H,m), 2.30(2H,t,J=7.2Hz), 2.96(4H,m), 3.64(3H,s), 3.80(2H,d,J=6.0Hz), 4.07(2H,q,J=7.2Hz), 4.41(1H,m), 5.47(2H,brs), 6.09(2H,brs), 6.37(1H,s), 7.33(2H,d,J=9.5Hz), 7.80(2H,d,J=9.5Hz), 8.32(1H,t,J=6.0Hz), 8.70(1H,d,J=6.6Hz), 10.42(1H,brs).

(8) Methyl N(α)-[4-[2-(2,4-diamino-7H-pyrrolo[2,3-d]pyrimidin-5-yl)ethyl]benzoyl]-N-(2methoxycarbonylphenyl]-L-glutaminate ¹H-NMR(CDCl₃) δ: 2.38(2H,m), 2.64(2H,m), 2.90(4H,m), 3.75(3H,s), 3.88(3H,s), 4.80(1H,m), 6.38(1H,s), 7.07(2H,d,J=8.0Hz), 7.07(1H,t,J=8.0Hz), 7.50(1H,t,J=8.0Hz), 7.65(2H,d,J=8.0Hz), 7.67(1H,d,J=8.0Hz), 7.97(1H,dd,J=1.2Hz, 8.0Hz), 8.62(1H,d,J=7.8Hz), 11.14(1H,brs) IR(KBr) ν: 3300, 3200, 2980, 2950, 2670, 2450, 1740, 1680, 1650, 1605, 1590, 1525, 1500, 1445, 1435, 1310, 1295, 1260, 1200, 1175, 1130, 1085, 830, 800, 760, 720 cm⁻¹

(9) Methyl N(α)-[4-[2-(2,4-diamino-7H-pyrrolo[2,3-d]pyrimidin-5-yl)ethyl]benzoyl]-N-(3-cyanophenyl)-L-glutaminate ¹H-NMR (CDCl₃+CD₃OD) δ: 2.05-2.45(2H,m), 2.52(2H,t,J=5.4Hz), 2.99(4H,s), 3.78(3H,s), 4.79(1H,m), 6.44(2H,s), 7.18(2H,d,J=8.4Hz), 7.34(2H,m), 7.69(2H,d,J=8.4Hz), 7.74(1H,m), 7.91(1H,s). IR(KBr) ν: 3380, 2920, 2850, 2230, 1735, 1605, 1545, 1480, 1425, 1320, 1305, 1285, 1255, 1210, 1165, 1090, 1015, 795, 755, 680 cm⁻¹

(10) Methyl N(α)-[4-[2-(2,4-diamino-7H-pyrrolo[2,3-d]pyrimidin-5-yl)ethyl]benzoyl]-N-(4-cyanophenyl)-L-glutaminate ¹H-NMR(DMSO-d₆) δ: 1.9-2.35(2H,m), 2.56(2H,m), 2.96(4H,m), 3.65(3H,s), 4.49(1H,m), 5.36(2H,s), 5.99(2H,s), 6.35(1H,d,J=1.8Hz), 7.33(2H,d,J=8.2Hz), 7.75(4H,s), 7.80(2H,d,J=8.2Hz), 8.70(1H,d,J=7.6Hz), 10.37(2H,s). IR(KBr) ν: 3390, 3200, 2930, 2850, 2230, 1740, 1610, 1580, 1535, 1505, 1330, 1315, 1260, 1220, 1180, 1090, 1020, 990, 840, 800, 760, 550 cm⁻¹

(11) Methyl N(α)-[4-[2-(2,4-diamino-7H-pyrrolo[2,3-d]pyrimidin-5-yl)ethyl]benzoyl]-N-(4-(1H-tetrazole-5-yl)phenyl]-L-glutaminate ¹H-NMR (DMSO-d₆) δ: 1.4-2.35(2H,m), 2.50(2H,m), 2.97(4H,m), 3.66(3H,s), 5.70(2H,brs), 6.41(1H,s), 7.34(2H,d,J=8.0Hz), 7.71(2H,d,J=8.6Hz), 7.82(2H,d,J=8.0Hz), 7.93(2H,d,J=8.6Hz), 8.73(1H,d,J=8.0Hz), 10.14(1H,s), 10.58(1H,s). IR(KBr) ν: 3400, 3300, 2920, 2850, 1735, 1635, 1605, 1535, 1500, 1445, 1420, 1370, 1335, 1300, 1245, 1220, 1170, 1155, 1100, 1060, 1030, 1005, 840, 830, 755, 680 cm⁻¹

(12) Methyl N(α)-[4-[2-(2,4-diamino-7H-pyrrolo[2,3-d]pyrimidin-5-yl)ethyl]benzoyl]-N-[3-(methoxycarbonylmethyl)phenyl]-L-glutaminate ¹H-NMR(DMSO-d₆) δ: 1.80-2.40(2H,m), 2.47(2H,t,J=7.2Hz), 3.61(3H,s), 3.62(2H,s), 3.65(3H,s), 4.46(1H,m), 5.64(2H,brs), 6.27(2H,s), 6.40(1H,d,J=1.0Hz), 6.91(1H,d,J=7.6Hz), 7.22(1H,d,J=7.6Hz), 7.33(2H,d,J=8.0Hz), 7.46(1H,d,J=7.6Hz), 7.49(1H,s), 7.81(2H,d,J=8.0Hz), 8.69(1H,d,J=7.2Hz), 9.92(1H,s), 10.51(1H,d,J=1.0Hz). IR(KBr) ν: 3350, 3200, 2950, 2850, 1735, 1610, 1570, 1550, 1490, 1435, 1330, 1305, 1260, 1200, 1170, 1090, 1010, 795, 770, 720, 690, 600 cm⁻¹

(13) Methyl N(α)-[4-[2-(2,4-diamino-7H-pyrrolo[2,3-d]pyrimidin-5-yl)ethyl]benzoyl]-N-(1H-tetrazole-5-yl)-L-glutaminate ¹H-NMR(DMSO-d₆) δ: 2.00-2.35(2H,m), 2.61(2H,m), 2.96(4H,m), 3.64(3H,s), 4.49(1H,m), 5.60(1H,s), 6.85(2H,s), 7.33(2H,d,J=7.8Hz), 7.49(2H,s), 7.80(2H,d,J=7.8Hz), 8.68(1H,d,J=7.6Hz), 11.26(1H,s), 11.97(1H,s). IR(KBr) ν: 3370, 3200, 2920, 1715, 1640, 1610, 1590, 1540, 1500, 1430, 1200, 1180, 1130, 1035, 720 cm⁻¹

Example 8

Production of N(α)-[4-[3-(2,4-diamino-7H-pyrrolo [2,3-d]pyrimidin-5-yl)propyl]benzoyl]-N-(3-borophenyl)-L-glutamine To a methanol/tetrahydrofuran (2:1; 15 ml) solution of methyl N(α)-[4-[3-(2,4-diamino-7H-pyrrolo[2,3-d]pyrimidin-5-yl)propyl]benzoyl]-N-(3-borophenyl)-L-glutaminate (1 g) was added a 1N aqueous solution (6 ml) of sodium hydroxide (6 ml), and the mixture was stirred for 5 hours at room temperature. The reaction mixture was concentrated under reduced pressure. The concentrate was dissolved in water, whose pH was adjusted to 4 with 1N hydrochloric acid. Resulting precipitates were collected by filtration, washed with water, then dried under reduced pressure to afford the subject compound (839 mg; yield 86%).

¹H-NMR(DMSO-d₆) δ: 1.84(2H,m), 1.90-2.30(4H,m), 2.45(2H,m), 2.71(4H,m), 4.23(1H,m), 5.71(2H,brs), 6.29(2H,brs), 6.49(1H,s), 7.24(1H,t,J=8.0Hz), 7.31(2H,d,J=8.0Hz), 7.46(1H,d,J=7.2Hz), 7.70(1H,brd,J=8.4Hz), 7.82(1H,brs), 7.84(2H,d,J=8.0Hz), 7.98(2H,brs), 8.55(1H,d,J=7.6Hz), 9.85(1H,s), 10.60(1H,brs). IR(KBr) ν: 3320, 3200, 2930, 1660, 1640, 1545, 1490, 1425, 1380, 1340, 705 cm⁻¹.

Example 9

In substantially the same manner as in Example 8, the carboxylic acid ester (1 g) produced in Example 7 was subjected to alkali hydrolysis to synthesize the following compounds:

(1) N(α)-[4-[2-(2,4-diamino-7H-pyrrolo[2,3-d]pyrimidin-5-yl)ethyl]benzoyl]-N-(3-borophenyl)-L-glutamine ¹H-NMR(DMSO-d₆) δ: 1.90-2.30(4H,m), 2.97(4H,m), 4.41(1H,m), 5.74(2H,brs), 6.41(3H,brs), 7.23(1H,t,J=8.0Hz), 7.33(2H,d,J=8.0Hz), 7.46(1H,d,J=7.2Hz), 7.70(1H,brd,J=8.2Hz), 7.82(1H,brs), 7.82(2H,d,J=8.0Hz), 7.99(2H,brs), 8.57(1H,d,J=7.6Hz), 9.85(1H,s), 10.58(1H,brs).

(2) N(α)-[4-[2-(2,4-diamino-7H-pyrrolo[2,3-d]pyrimidin-5-yl)ethyl]benzoyl]-N-(3-carboxyphenyl)-L-glutamine ¹H-NMR(DMSO-d₆) δ: 1.9-2.4(2H,m), 2.44(2H,m), 2.96(4H,m), 4.41(1H,m), 5.66(2H,brs), 6.32(2H,brs), 6.40(1H,s), 7.33(2H,d,J=8.4Hz), 7.39(2H,t,J=7.8Hz), 7.60(1H,dt,J=7.8Hz, 1.2Hz), 7.78(1H,dd,J=7.8Hz, 1.2Hz), 7.79(2H,d,J=8.4Hz), 8.22(1H,t,J=1.2Hz), 8.55(1H,d,J=7.6Hz), 10.12(1H,s), 10.53(1H,s). IR(KBr) ν: 3350, 3200, 2930, 2850, 1645, 1600, 1545, 1500, 1440, 1385, 1300, 1260, 1190, 1095, 1020, 905, 820, 760 cm⁻¹.

(3) N(α)-[4-[2-(2,4-diamino-7H-pyrrolo[2,3-d]pyrimidin-5-yl)ethyl]benzoyl]-N-(4-carboxyphenyl)-L-glutamine ¹H-NMR(DMSO-d₆) δ: 1.8-2.35(2H,m), 2.50(2H,m), 2.96(4H,m), 4.43(1H,m), 5.70(2H,brs), 6.36(2H,brs), 6.41(1H,s), 7.33(2H,d,J=8.4Hz), 7.73(2H,d,J=8.8Hz), 7.81(2H,d,J=8.4Hz), 7.87(2H,d,J=8.8 Hz), 8.55(1H,d,J=7.6Hz), 10.25(1H,s), 10.56(1H,brs). IR(KBr) ν: 3375, 3200 (sh.), 2920, 1640, 1600, 1455, 1405, 1380, 1305, 1255, 1100, 855, 770 cm⁻¹.

(4) N(α)-[4-[2-(2,4-diamino-7H-pyrrolo[2,3-d]pyrimidin-5-yl)ethyl]benzoyl]-N-(3-hydroxyphenyl)-L-glutamine ¹H-NMR(DMSO-d₆) δ: 1.8-2.3(2H,m), 2.46(2H,t,J=7.4 Hz), 2.99(4H,m), 4.39(1H,m), 5.97(2H,brs), 6.42(1H,d,J=8.0Hz), 6.46(1H,s), 6.62(2H,brs), 6.92(1H,d,J=8.0Hz), 7.04(1H,t,J=8.0Hz), 7.17(1H,s), 7.34(2H,d,J=8.2Hz), 7.83(2H,d,J=8.2Hz), 8.57(1H,d,J=7.6Hz), 9.34(1H,s), 9.80(1H,s), 10.73(1H,brs). IR(KBr) $\nu$: 3330, 3200, 2920, 2850, 1640, 1610, 1545, 1495, 1445, 1385, 1340, 1225, 1185, 1155, 1090, 855, 770, 690 cm$^{-1}$.

(5) N($\alpha$)-[4-[2-(2,4-diamino-7H-pyrrolo[2,3-d]pyrimidin-5-yl)ethyl]benzoyl]-N-(4-hydroxyphenyl)-L-glutamine $^1$H-NMR(DMSO-d$_6$) $\delta$: 1.85–2.30(2H,m), 2.94(2H,t,J=7.2Hz), 2.96(4H,m), 4.39(1H,m), 5.58(2H,brs), 6.21(2H,brs), 6.38(1H,s), 6.36(2H,d,J=8.8Hz), 7.33(2H,d,J=8.2Hz), 7.34(2H,d,J=8.8Hz), 7.81(2H,d,J=8.2Hz), 8.56(1H,d,J=7.8Hz), 9.14(1H,s), 9.67(1H,s), 10.48(1H,brs). IR(KBr) $\nu$: 3400, 3340, 3220, 2930, 2855, 1650, 1545, 1515, 1450, 1400, 1340, 1305, 1240, 1170, 1100, 835, 770 cm$^{-1}$.

(6) N($\alpha$)-[4-[2-(2,4-diamino-7H,pyrrolo[2,3-d]pyrimidin-5-yl)ethyl]benzoyl]-N-[3-(1H-tetrazol-5-yl)phenyl]-L-glutamine $^1$H-NMR (DMSO-d$_6$) $\delta$: 1.8–2.4(2H,m), 2.50(2H,m), 2.96(4H,m), 4.42(1H,m), 6.10(2H,brs), 6.48(1H,s), 6.77(2H,brs), 7.33(2H,d,J=8.0Hz), 7.43(1H,d,J=7.6Hz), 7.67(2H,m), 7.82(2H,d,J=8.0Hz), 8.30(1H,s), 8.58(1H,d,J=7.0Hz), 10.13(1H,s), 10.81(1H,s). IR(KBr) $\nu$: 3340, 3200, 2925, 2850, 1645, 1570, 1545, 1500, 1455, 1400, 1300, 1280, 1255, 1190, 1090, 800, 760, 745, 690, 630, 590, 550 cm$^{-1}$.

(7) N-[N-($\alpha$)-[4-[2-(2,4-diamino-7H-pyrrolo[2,3-d]pyrimidin-5-yl)ethyl]benzoyl-L-$\gamma$-glutamyl]glycine $^1$H-NMR(DMSO-d$_6$) $\delta$: 1.80–2.15(2H,m), 2.26(2H,t,J=5.8Hz), 2.96(4H,s), 3.68(1H,d,J=5.6Hz), 3.87(1H,d,J=5.6Hz), 4.27(1H,m), 5.48(2H,brs), 6.12(2H,brs), 6.38(1H,s), 7.33(2H,d,J=8.2Hz), 7.78(2H,d,J=8.26Hz), 8.11(1H,t,J=5.6Hz), 8.48(1H,d,J=7.2Hz), 10.44(1H,brs). IR(KBr) $\nu$: 3400, 3170, 2920, 1635, 1540, 1495, 1455, 1385, 1290, 1250, 1230 cm$^{-1}$.

(8) N($\alpha$)-[4-[2-(2,4-diamino-7H-pyrrolo[2,3-d]pyrimidin-5-yl)ethyl]benzoyl]-N-(2-carboxyphenyl)-L-glutamine $^1$H-NMR(DMSO-d$_6$) $\delta$: 1.9–2.4(2H,m), 2.50(2H,m), 3.00(4H,m), 4.40(1H,m), 6.64(1H,s), 6.67(2H,brs), 7.07(1H,dt,J=1.2Hz, 7.8Hz), 7.23(2H,d,J=8.0Hz), 7.29(2H,s), 7.47(1H,dt,J=1.6Hz, 8.6Hz), 7.83(2H,d,J=8.0Hz), 8.04(1H,dd,J=1.6Hz, 8.4Hz), 8.52(1H,d,J=8.4Hz), 8.56(1H,d,J=8.4Hz), 11.36(1H,s), 2.03(1H,s). IR(KBr) $\nu$: 3320, 3200, 2910, 2830, 1655, 1640, 1580, 1520, 1495, 2440, 1370, 1285, 1240, 750 cm$^{-1}$.

(9) N($\alpha$)-[4-[2-(2,4-diamino-7H-pyrrolo[2,3-d]pyrimidin-5-yl)ethyl]benzoyl]-N-(3-cyanophenyl)-L-glutamine $^1$H-NMR(DMSO-d$_6$) $\delta$: 1.92–2.34(2H,m), 2.5(2H,m), 2.96(4H,m), 4.44(1H,m), 5.66(2H,brs), 6.30(2H,brs), 6.40(1H,s), 7.33(2H,d,J=8.0Hz), 7.48(2H,m), 7.81(3H,d,J=8.0Hz), 8.08(1H, s), 8.57(1H,d,J=7.0Hz), 10.35(1H,s), 10.54(1H,s). IR(KBr) $\nu$: 3350, 3200, 2925, 2850, 2225, 1640, 1585, 1545, 1500, 1480, 1450, 1430, 1390, 1330, 1300, 1285, 1255, 1190, 1170, 1095, 1015, 790, 755, 680 cm$^{-1}$.

(10) N($\alpha$)-[4-[2-(2,4-diamino-7H-pyrrolo[2,3-d]pyrimidin-5-yl)ethyl]benzoyl]-N-(4-cyanophenyl)-L-glutamine $^1$H-NMR(DMSO-d$_6$) $\delta$: 1.5–2.45(4H,m), 2.96(4H,m), 4.40(1H,m), 5.54(2H,s), 6.19(2H,brs), 6.38(1H,s), 7.32(2H,d,J=8.2Hz), 7.75(4H,s), 7.80(2H,d,J=8.2Hz), 8.54(1H,d,J=8.0Hz), 10.39(1H,s), 10.46(1H,s). IR(KBr) $\nu$: 3410, 2930, 2855, 2230, 1645, 1600, 1535, 1510, 1455, 1410, 1310, 1260, 1175, 1100, 840 555 cm$^{-1}$.

(11) N($\alpha$)-[4-[2-(2,4-diamino-7H-pyrrolo[2,3-d]pyrimidin-5-yl)ethyl]benzoyl-N-[4-(1H-tetrazole-5-yl)phenyl]-L-glutamine $^1$H-NMR(DMSO-d$_6$) $\delta$: 1.8–2.35(2H,m), 2.50(2H,m), 2.97(4H,m), 4.43(1H,m), 6.15(2H,brs), 6.47(1H,s), 6.81(2H,s), 7.33(2H,d,J=8.2Hz), 7.76(2H,d,J=8.7Hz), 7.82(2H,d,J=8.2Hz), 7.95(2H,d,J=8.7Hz), 8.58(1H,d,J=8.0Hz), 10.22(1H,s), 10.84(1H,s). IR(KBr) $\nu$: 3400, 3200, 2930, 2850, 1640, 1570, 1540, 1500, 1450, 1430, 1385, 1335, 1310, 1255, 1185, 1155, 1095, 1075, 1020, 1000, 845, 750, 590 525 cm$^{-1}$.

(12) N($\alpha$)-[4-[2-(2,4-diamino-7H-pyrrolo[2,3-d]pyrimidin-5-yl)ethyl]benzoyl-N-[3-(carboxylmethyl)phenyl]-L-glutamine $^1$H-NMR(DMSO-d$_6$) $\delta$: 1.90–2.40(2H,m), 2.46(2H,t,J=7.0Hz), 2.96(4H,m), 3.50(2H,s), 4.41(1H,m), 5.47(2H,brs), 6.11(2H,s), 6.35(1H,d,J=8.0Hz), 6.37(1H,s), 7.20(1H,t,J=8.0Hz), 7.33(2H,d,J=8.4Hz), 7.47(1H,d,J=8.0Hz), 7.49(1H,s), 7.81(2H,d,J=8.4Hz), 8.54(1H,d,J=7.0Hz), 9.93(1H,s), 10.41(1H,s). IR(KBr) $\nu$: 3330, 3200, 2920, 1660, 1630, 1610, 1595, 1555, 1540, 1500, 1435, 1380, 1350, 1285, 1255, 1210, 1180, 1160, 1090, 1070, 770, 720, 660 cm$^{-1}$.

(13) N($\alpha$)-[4-[2(2,4-diamino-7H-pyrrolo[2,3-d]pyrimidin-5-yl)ethyl]benzoyl-N-(1H-tetrazole-5-yl)-L-glutamine $^1$H-NMR(DMSO-d$_6$) $\delta$: 1.95–2.50(2H,m), 2.60(2H,m), 2.96(4H,m), 4.43(1H,m), 5.88(2H,brs), 6.43(1H,s), 6.52(2H,s), 7.32(2H,d,J=8.4Hz), 7.79(2H,d,J=8.4Hz), 8.54(1H,d,J=8.0Hz), 10.56(1H,s), 11.88(1H,brs). IR(KBr) $\nu$: 3380, 3270, 3200, 2910, 1680, 1630, 1605, 1540, 1490, 1450, 1380, 1330, 1240, 1155, 1040 cm$^{-1}$.

Example 10

Production of N($\alpha$)-[4-[2-(2,4-diamino-7H-pyrrolo [2,3-d]pyrimidin-5-yl)ethyl]benzoyl]-N($\gamma$)-hemiphthaloyl-L-2,4-diaminobutyric acid In substantially the same manner as in Example 6, 4-[2-(2,4-diamino-7H-pyrrolo[2,3-d]pyrimidin-5-yl)ethyl]benzoic acid (566 mg) and methyl N($\gamma$)-phthaloyl-L-2,4-diaminobutyrate hydrochloride (625 mg) were subjected to condensation with diethyl cyanophosphate in the presence of triethylamine to afford methyl N($\alpha$)-[4-[2-(2,4-diamino-7H-pyrrolo[2,3-d]pyrimidin-5-yl)ethyl]benzoyl]-N($\gamma$)-phthaloyl-L-2,4-diaminobutyrate.

$^1$H-NMR(DMSO-d$_6$) $\delta$: 2.00–2.35(2H,m), 2.97(4H,m), 3.61(3H,s), 4.44(1H,m), 5.57(2H,brs), 6.20(2H,brs), 6.41(1H,s), 7.32(2H,d,J=8.2Hz), 7.75(2H,d,J=8.2Hz), 7.83(4H,s), 8.74(1H,d,J=7.6Hz), 10.49(1H,brs). IR(KBr) $\nu$: 3370, 3200, 1950, 1770, 1735, 1710, 1660, 1610, 1575, 1545, 1500, 1430, 1400, 1200, 1185, 720 cm$^{-1}$.

The whole amount of the above-mentioned ester was subjected to hydrolysis with sodium hydroxide, in substantially the same manner as in Example 8, to obtain the subject compound (850 mg; yield 82%).

$^1$H-NMR(DMSO-d$_6$) $\delta$: 1.75–2.20(2H,m), 2.96(4H,brs), 3.32(2H,m), 4.51(1H,m), 5.77(2H, brs), 6.41(3H, brs), 7.32(2H,d,J=8.0Hz), 7.35–7.55(3H,m), 7.70–7.85(3H,m), 8.31(1H,m), 8.53(1H,d,J=7.4Hz), 10.59(1H,brs).

Example 11

Production of N($\alpha$)-[4-[2-(2,4-diamino-7H-pyrrolo [2,3-d]pyrimidin-5-yl)ethyl]benzoyl]-N($\delta$)-(3,4-methylenedioxybenzoyl)-L-ornithine To a DMF solution of 4-[2-(2,4-diamino-7H-pyrrolo[2,3-d]pyrimidin-5-yl)ethyl]benzoic acid (1.52 g) and methyl ester of N(δ)-t-butyloxycarbonyl-L-ornithine (1.3 g) was added diethyl cyanophosphate (1.4 g). The mixture was stirred for one hour at room temperature in the presence of triethylamine (3.0 g). The reaction mixture was concentrated under reduced pressure. The concentrate was purified by column chromatography on silica gel (carrier: 30 g; chloroform:ethanol containing 1% ammonium=20:1–15:1) to afford methyl N(α)-[4-[2-(2,4-diamino-7H-pyrrolo[2,3-d]pyrimidin-5-yl)ethyl]benzoyl]-N-(δ)-(t-butyloxycarbonyl)-L-ornithinate (2.30 g; yield 85%).

$^1$H-NMR(DMSO-d$_6$) δ: 1.37(9H,s), 1.40–1.60(2H,m), 1.70–1.85(2H,m), 2.90–3.15(6H,m), 3.64(3H,s), 4.40(1H,m), 6.61(1H,s), 6.81(1H,t,J=7.0Hz), 6.97(2H,brs), 7.33(2H,d,J=8.2Hz), 7.63(2H,brs), 7.80(2H,d,J=8.2Hz), 8.63(1H,d,J=7.4Hz), 11.35(1H,brs).

To a dichloromethane (1 ml) solution of the above-mentioned methyl ornithinate (200 mg) was added dropwise, under ice-cooling, trifluoroacetic acid (1 ml), and the mixture was stirred for 20 minutes at room temperature. The reaction mixture was concentrated under reduced pressure. The concentrate was dissolved in DMF. To the solution were added 3,4-methylenedioxybenzoic acid (68 mg) and ethyl cyanophosphate (150 mg). The mixture was stirred for 10 minutes, to which was added dropwise, under ice-cooling, triethylamine (500 mg), followed by stirring for further two hours at room temperature. The reaction mixture was concentrated under reduced pressure. The concentrate was purified by column chromatography on silica gel (eluent; chloroform: 1% ammonia ethanol=15:1) to afford methyl N(δ)-(3,4-methylenedioxybenzoyl)-L-ornithinate. The whole amount of this product was dissolved in methanol (6 ml), to which was added, under ice-cooling, an aqueous solution of sodium hydroxide (1 ml), and the mixture was stirred for 5 hours at room temperature. The reaction mixture was concentrated under reduced pressure. The concentrate was dissolved in water, whose pH was adjusted to 4 with dilute hydrochloric acid. Resulting precipitates were collected by filtration, washed with water and dried under reduced pressure to afford the subject compound (108 mg; yield 51%).

$^1$H-NMR(DMSO-d$_6$) δ: 1.45–1.95(4H,m), 2.96(4H,brs), 3.25(2H,m), 4.39(1H,m), 5.83(2H,brs), 6.09(2H,s), 6.43(1H,s), 6.47(2H,brs), 6.97(1H,d,J=8.4Hz), 7.33(2H,d,J=8.0Hz), 7.38(1H,s), 7.43(1H,d,J=8.4Hz), 7.81(2H,d,J=8.0Hz), 8.33(1H,brt,J=5.2Hz), 8.53(1H,d,J=7.6Hz), 10.63(1H,brs). IR(KBr) ν: 3340, 3200, 2930, 1640, 1540, 1500, 1485, 1440, 1400, 1360, 1300, 1260, 1040 cm$^{-1}$.

Example 12

In substantially the same manner as in Example 11, methyl N(α)-[4-[2-(2,4-diamino-7H-pyrrolo[2,3-d]pyrimidin-5-yl)ethyl]benzoyl]-N(δ)-(t-butyloxy carbonyl)-L-ornithinate (1 mmol.) was converted into amino group with trifluoroacetic acid, which was subjected to condensation with diethyl cyanophosphate in the presence of carboxylic acid (1,1 mmol.) and triethylamine, followed by alkali hydrolysis to afford the following compounds:

(1) N(α)-[4-[2-(2,4-diamino-7H-pyrrolo[2,3-d]pyrimidin-5-yl)ethyl]benzoyl]-N(δ)-(3-carboxy-2-naphthoyl)-L-ornithine.

$^1$H-NMR(DMSO-d$_6$) δ: 1.60–2.05(4H,m), 2.96(4H,brs), 3.35(2H,m), 4.43(1H,m), 5.77(2H,brs), 6.42(3H,brs), 7.32(2H,d,J=8.0Hz), 7.60–7.70(2H,m), 7.83(2H,d,J=8.0Hz), 7.97(1H,s), 7.95–8.15(2H,m), 8.36(1H,s), 8.40–8.60(2H,m), 10.62(1H,brs). IR(KBr) ν: 3350, 3220, 2930, 1705, 1650, 1540, 1500, 1460, 1380, 1300 cm$^{-1}$.

(2) N(α)-[4-[2-(2,4-diamino-7H-pyrrolo[2,3-d]pyrimidin-5-yl)ethyl]benzoyl]-N(δ)-(2-hydroxybenzoyl)-L-ornithine $^1$H-NMR(DMSO-d$_6$) δ: 1.50–1.95(4H,m), 2.96(4H,brs), 3.33(2H,m), 4.41(1H,m), 5.73(2H,brs), 6.37(3H,brs), 6.41(1H,s), 6.80–6.95(2H,m), 7.32(2H,d,J=8.0Hz), 7.39(1H,m), 7.80(2H,d,J=8.0Hz), 7.84(1H,m), 8.53(1H,d,J=7.8Hz), 8.84(1H,m), 10.57(1H,brs). IR(KBr) ν: 3340, 3200, 2930, 1640, 1595, 1540, 1490, 1450, 1390, 1300, 1250, 755 cm$^{-1}$.

(3) N(α)-[4-[3-(2,4-diamino-7H-pyrrolo[2,3-d]pyrimidin-5-yl)propyl]benzoyl-N(δ)-(o-pyrrolidinocarbonylbenzoyl)-L-ornithin $^1$H-NMR(DMSO-d$_6$) δ: 1.50–2.00(8H,m), 2.97(4H,m), 3.09(2H,t,J=6.4Hz), 3.22(2H,m), 3.38(2H,m), 4.39(1H,m), 5.63(2H,brs), 6.28(2H,brs), 6.40(1H,s), 7.32(2H,d,J=8.2Hz), 7.25–7.65(4H,m), 7.82(2H,d,J=8.2Hz), 8.36(1H,t,J=5.0Hz), 8.51(1H,d,J=7.8Hz), 10.52(1H,brs). IR(KBr) ν: 3330, 1610, 1570, 1540, 1490, 1450, 1430 cm$^{-1}$.

(4) N(α)-[4-[2-(2,4-diamino-7H-pyrrolo[2,3-d]pyrimidin-5-yl)ethyl]benzoyl-N(δ)-(4-carboxybenzoyl)-L-ornithine $^1$H-NMR(DMSO-d$_6$) δ: 1.60–2.00(4H,m), 2.96(4H,brs), 3.30(2H,m), 4.41(1H,m), 5.45(2H,brs), 6.09(2H,brs), 6.37(1H,s), 7.33(2H,d,J=8.2Hz), 7.80(2H,d,J=8.2Hz), 7.92(2H,d,J=8.6Hz), 8.00(2H,d,J=8.6Hz), 8.51(1H,d,J=8.0Hz), 8.66(1H,t,J=5.8Hz), 10.41(1H,brs). IR(KBr) ν: 3330, 3200, 2930, 1640, 1570, 1540, 1500, 1455, 1385, 1290, 1190, 730 cm$^{-1}$.

(5) N(α)-[4-[2-(2,4-diamino-7H-pyrrolo[2,3-d]pyrimidin-5-yl)ethyl]benzoyl-N(δ)-(3(E)-carboxyl-2-propenoyl)-L-ornithine $^1$H-NMR(DMSO-d$_6$) δ: 1.40–1.90(4H,m), 2.96(4H,brs), 3.16(2H,m), 4.32(1H,m), 5.48(2H,brs), 6.12(2H,brs), 6.37(1H,s), 6.51(1H,d,J=15.4Hz), 6.83(1H,d,J=15.4Hz), 7.32(2H,d,J=8.0Hz), 7.78(2H,d,J=8.0Hz), 8.38(1H,d,J=7.4Hz), 8.47(1H,m), 10.42(1H,brs). IR(KBr) ν: 3325, 3200, 2925, 1645, 1620, 1565, 1540, 1500, 1460, 1390, 1330, 1190, 1090, 975 cm$^{-1}$.

(6) N(α)-[4-[2-(2,4-diamino-7H-pyrrolo[2,3-d]pyrimidin-5-yl)ethyl]benzoyl-N(δ)-(3-carboxylpropyonyl)-L-ornithine $^1$H-NMR(DMSO-d$_6$) δ: 1.40–1.90(4H,m), 2.20–2.50(4H,m), 2.96(4H,brs), 3.05(2H,m), 4.34(1H,m), 5.58(2H,brs), 6.22(2H,brs), 6.39(1H,s), 7.33(2H,d,J=8.2Hz), 7.80(2H,d,J=8.2Hz), 7.86(1H,t,J=7.6Hz), 8.49(1H,d,J=7.4Hz), 10.48(1H,brs). IR(KBr) ν: 3330, 3200, 2930, 1640, 1545, 1500, 1455, 1400 cm$^{-1}$.

(7) N(α)-[4-[2-(2,4-diamino-7H-pyrrolo[2,3-d]pyrimidin-5-yl)ethyl]benzoyl-N(δ)-(3,4,5-trimethoxybenzoyl)-L-ornithine $^1$H-NMR(DMSO-d$_6$) δ: 1.50–2.00(4H,m), 2.95(4H,brs), 3.29(2H,m), 3.69(3H,s), 3.81(6H,s), 4.38(1H,m), 5.45(2H,brs), 6.08(2H,brs), 6.36(1H,s), 7.17(2H,s), 7.32(2H,d,J=8.2Hz), 7.80(2H,d,J=8.2 Hz), 8.40–8.55(2H,m), 10.40(1H,brs). IR(KBr) ν: 3340, 3200, 2940, 1640, 1590, 1540, 1460, 1410, 1335, 1235, 1185, 1125, 1000, 760 cm$^{-1}$.

(8) N(α)-[4-[2-(2,4-diamino-7H-pyrrolo[2,3-d]pyrimidin-5-yl)ethyl]benzoyl-N(δ)-(4-acetamidobenzoyl)-L-ornithine $^1$H-NMR(DMSO-d$_6$) δ: 1.45–1.95(4H,m), 2.06(3H,s), 2.96(4H,brs), 3.27(2H,m), 4.39(1H,m), 5.83(2H,brs), 6.43(1H,s), 6.50(2H,brs), 7.33(2H,d,J=8.0Hz), 7.63(2H,d,J=8.4Hz), 7.79(2H,d,J=8.4Hz), 7.81(2H,d,J=8.0Hz), 8.36(1H,m), 8.53(1H,d,J=7.8Hz), 10.16(1H,s), 10.65(1H,brs). IR(KBr) ν: 3320, 3200, 2930, 1640, 1530, 1500, 1460, 1400, 1370, 1315, 1260, 1180 cm$^{-1}$.

(9) N(α)-[4-[2-(2,4-diamino-7H-pyrrolo[2,3-d]pyrimidin-5-yl)ethyl]benzoyl-N(δ)-(2,6-dimethylbenzoyl)-L-ornithine $^1$H-NMR(DMSO-d$_6$) δ: 1.50–2.00(4H,m), 2.19(6H,s), 2.96(4H,brs), 4.38(1H,m), 5.45(2H,brs), 6.07(2H,brs), 6.36(1H,s), 7.01(2H,d,J=7.8Hz), 7.16(1H,dd,J=8.7, 6.4Hz), 7.33(2H,d,J=8.0Hz), 7.79(2H,d,J=8.0Hz), 8.29(1H,t,J=5.0Hz), 8.51(1H,d,J=7.7Hz), 10.40(1H,brs). IR(KBr) ν: 3330, 3200, 2925, 1640, 1600, 1560, 1540, 1500, 1460, 1400, 1300, 770 cm$^{-1}$.

Example 13

Each of carboxylic acids obtained in Examples 9(1), 9(2), 5(1), 10 and 12(1), respectively, was dissolved in an aqueous solution of sodium hydroxide having the equivalent mole to the carboxylic acid. And the solution was lyophilized to obtain the following sodium salt.

(1) Sodium N(α)-[4-[2-(2,4-diamino-7H-pyrrolo[2,3-d]pyrimidin-5-yl)ethyl]benzoyl-N-(3-borophenyl-L-glutaminate $^1$H-NMR(DMSO-d$_6$) δ: 1.85–2.20(2H,m), 2.34(2H,t,J=8.0Hz), 2.95(4H,m), 4.08(1H,m), 5.35(2H,s), 5.95(2H,s), 6.37(1H,s), 7.20(1H,t,J=7.8Hz), 7.32(2H,d,J=8.2Hz), 7.40(1H,d,J=7.8Hz), 7.65–7.80(4H,m), 7.86(1H,d,J=6.2Hz), 10.31(1H,brs), 10.35(1H,brs). IR(KBr) ν: 3400, 1650, 1610, 1580, 1540, 1490, 1430, 1410, 1340 cm$^{-1}$.

(2) Disodium N(α)-[4-[2-(2,4-diamino-7H-pyrrolo[2,3-d]pyrimidin-5-yl)ethyl]benzoyl-N-(3-carboxyphenyl)-L-glutaminate $^1$H-NMR(DMSO-d$_6$) δ: 1.90–2.10(2H,m), 2.32(2H,t,J=7.4Hz), 2.94(4H,m), 4.01(1H,m), 5.34(2H,s), 5.95(2H,s), 6.36(1H,s), 7.13(1H,t,J=7.9Hz), 7.32(2H,d,J=8.2Hz), 7.50(1H,d,J=7.8Hz), 7.65(1H,d,J=7.8Hz), 7.69(2H,d,J=8.2Hz), 7.85(1H,d,J=6.0Hz), 7.91(1H,t,J=1.2Hz), 10.34(1H,s), 10.37(1H,s). IR(KBr) ν: 3370, 1650, 1610, 1570, 1560, 1545, 1530, 1490, 1430, 1385, 770 cm$^{-1}$.

(3) Disodium N(α)-[4-[2-(2,4-diamino-7H-pyrrolo[2,3-d]pyrimidin-5-yl)ethyl]benzoyl-N(δ)-hemiphthaloyl-L-ornithinate $^1$H-NMR(DMSO-d$_6$) δ: 1.40–1.60(2H,m), 1.70–2.00(2H,m), 2.94(4H,m), 3.20(2H,m), 4.11(1H,m), 5.36(2H,s), 5.96(2H,s), 6.37(1H,s), 7.20–7.50(5H,m), 7.64(1H,dd,J=7.8, 1.8Hz), 7.76(2H,d,J=8.0Hz), 7.96(1H,d,J=6.6Hz), 10.10(1H,brs), 10.37(1H,s). IR(KBr) ν: 3380, 1610, 1580, 1490, 1430, 1390, 1310, 1190, 1090 cm$^{-1}$.

(4) Disodium N(α)-[4-[2-(2,4-diamino-7H-pyrrolo[2,3-d]pyrimidin-5-yl)ethyl]benzoyl-N(γ)-hemiphthaloyl-L-2,4-diaminobutyrate $^1$H-NMR(DMSO-d$_6$) δ: 1.70–2.10(2H,m), 2.95(4H,m), 3.17(2H,m), 4.03(1H,m), 5.34(2H,s), 5.94(2H,s), 6.36(1H,s), 7.15–7.45(5H,m), 7.63(1H,dd,J=7.6, 1.4Hz), 7.72(2H,d,J=8.2Hz), 7.88(1H,d,J=6.6Hz), 10.25(1H,brs), 10.34(1H,brs). IR(KBr) ν: 3390, 1610, 1585, 1550, 1530, 1490, 1430, 1395, 1310 cm$^{-1}$.

(5) Disodium N(α)-[4-[2-(2,4-diamino-7H-pyrrolo[2,3-d]pyrimidin-5-yl)ethyl]benzoyl-N(δ)-(3-carboxyl-2-naphthoyl)-L-ornithinate $^1$H-NMR(DMSO-d$_6$) δ: 1.40–1.60(2H,m), 1.70–2.10(2H,m), 2.92(4H,m), 3.20(2H,m), 4.15(1H,m), 5.34(2H,s), 5.93(2H,s), 6.36(1H,s), 7.30(2H,d,J=8.0Hz), 7.45–7.55(2H,m), 7.75(2H,d,J=8.0Hz), 7.85–8.00(3H,m), 7.97(1H,s), 8.25(1H,s), 10.35(1H,brs). IR(KBr) ν: 3400, 1685, 1610, 1580, 1550, 1490, 1460, 1435, 1400, 1350, 1325, 1300, 1205, 1180, 1130 cm$^{-1}$.

The compounds of this invention have highly specific toxicities to various tumor cells (especially to cells of human lung cancer) and show excellent therapeutic effects on methotrexate-resistant tumor cells as well.

What is claimed is:

1. A compound of the formula,

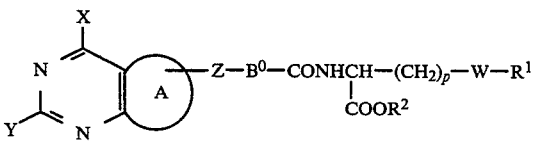

wherein the ring A stands for an optionally hydrogenated pyrrole; B$^0$ stands for a cyclopentylene, cyclohexylene, 1,3- or 3,5,cyclopentadien-1,3-ylene, cyclopenten-(1,3-, 1,4- or 3,5-)ylene, cyclopentan-1,3-ylene, phenyl-(1,3- or 1,4-)ylene, cyclohexan-(1,3- or 1,4-)ylene, cyclohexen(1,3-, 1,4-, 1,5-, 3,5- or 3,6-)ylene, 1,3-cyclohexadien-(1,3-, 1,4-, 1,5-, 2,4-, 2,5- or 2,6-)ylene, 1,4-cyclohexadien-(1,3-, 1,4-, or 1,5-)ylene, 1,2-phenylene, 1,3-phenylene, 1,4-phenylene, thiophen-(2,4-, 2,5- or 3,4-)ylene, furan-(2,4-, 2,5- or 3,4-)ylene, pyrrol-(1,3-, 2,4-, 2,5- or 3,4-)ylene, thiazol-(2,4- or 2,5-)ylene, imidazol-(1,4-, 2,4- or 2,5-)ylene, thiadiazol-2,5-ylene, pyridin-(2,4-, 2,5-, 2,6-, or 3,5-)ylene, pyran-(2,4-, 2,5-, 2,6-, 3,5-, 3,6-, or 4,6-)ylene, pyrazin-(2,5- or 2,6-)ylene, pyrimidin-(2,4- or 2,5-)ylene, pyridazin-3,5-ylene or a partially or completely reduced form thereof, which may be substituted with 1 or 2 substituents selected from the group consisting of a C$_{1-4}$ alkyl group, C$_{2-4}$ alkenyl group, C$_{2-4}$ alkynyl group, C$_{3-8}$ cycloalkyl group, halogen atom, hydroxyl group, C$_{1-4}$ alkoxy, di-C$_{1-4}$ alkylamino group, halogeno-C$_{1-4}$ alkyl group, oxo, C$_{1-4}$ acyl group and C$_{1-4}$ alkoxy-C$_{1-4}$ alkyl group; X stands for an amino group, hydroxyl group or mercapto group; Y stands for (1) hydrogen atom,
(2) a halogen atom,
(3) cyano group,
(4) carboxyl group,
(5) carbamoyl group,
(6) amino group,
(7) nitro group,
(8) hydroxyl group,
(9) mercapto group,
(10) a C$_{1-4}$ alkyl group, C$_{2-4}$ alkenyl group, C$_{2-4}$ alkynyl group, C$_{3-8}$ cycloalkyl group, a C$_{1-4}$ alkoxy group, C$_{1-4}$ alkylthio group, C$_{1-4}$ alkyl-carbonylamino group or C$_{1-4}$ alkylcarbonyloxy group,
(11) a C$_{6-10}$ aryl group, C$_{6-10}$ aryloxy group, C$_{6-10}$ arylthio group, C$_{6-10}$ arylcarbonylamino group or a C$_{6-10}$ arylcarbonyloxy group,

(12) a heterocyclic group, heterocyclic-oxy group, heterocyclic-thio group, heterocyclic-carbonylamino group or heterocyclic-carbonyloxy group wherein the heterocyclic group is selected from the group consisting of pyrrolyl, imidazolyl, pyrazolyl, thienyl, furyl, thiazolyl, thiadiazolyl, oxazolyl, oxadiazolyl, pyridyl, pyranyl, pyrazinyl, pyrimidinyl, pyridazinyl, dioxoranyl, piperidino, morpholino, N-methylpiperazinyl, N-ethylpiperazinyl and dioxanyl,

(13) an amino group substituted with one or two groups selected from the group consisting of a $C_{1-4}$ alkyl, $C_{2-4}$ alkenyl, $C_{2-4}$ alkynyl, $C_{6-10}$ aryl, pyrrolyl, imidazolyl, pyrazolyl, thienyl, furyl, thiazolyl, thiadiazolyl, oxazolyl, oxadiazolyl, pyridyl, pyranyl, pyrazinyl, pyrimidinyl, pyridazinyl, dioxoranyl, piperidino, morpholino, N-methylpiperazinyl, N-ethylpiperazinyl and dioxanyl, or

(14) a group mentioned in the above (10) to (12), which is substituted with one or two substituents selected from the group consisting of a $C_{1-4}$ alkyl group, $C_{2-4}$ alkenyl group, $C_{2-4}$ alkynyl group, $C_{3-8}$ cycloalkyl group, halogen, hydroxyl group, oxo group, $C_{1-4}$ alkoxy group, di-$C_{1-4}$ alkylamino group, halogeno-$C_{1-4}$ alkyl group, $C_{1-4}$ acyl group, hydroxy-$C_{1-4}$ alkyl group, and $C_{1-4}$ alkoxy-$C_{1-4}$ alkyl group;

Z is a $C_{1-5}$ alkylene, $C_{2-5}$ alkenylene or $C_{2-5}$ alkynylene group which may be substituted with one or two substituents selected from the group consisting of a $C_{1-4}$ alkyl group, $C_{2-4}$ alkenyl group, $C_{2-4}$ alkynyl group, $C_{3-8}$ cycloalkyl group, halogen, hydroxyl group, oxo, $C_{1-4}$ alkoxy group, di-$C_{1-4}$ alkylamino group, halogeno-$C_{1-4}$ alkyl group, $C_{1-4}$ acyl group, hydroxy-$C_{1-4}$ alkyl group and $C_{1-4}$ alkoxy-$C_{1-4}$ alkyl group, or a group of the formula: —$Z^1$—$Z^2$—$Z^3$— wherein $Z^1$ and $Z^3$ independently stand for a bond, a $C_{1-4}$ alkylene group, $C_{2-4}$ alkenylene or $C_{2-4}$ alkynylene, and $Z^2$ stands for —O—, a group of the formula: —S(O)n′— wherein n′ denotes an integer of 0 to 2, or a group of the formula: —NR$^4$— wherein R$^4$ stands for (1) a hydrogen atom, (2) a $C_{1-4}$ alkoxycarbonyl group or (3) a $C_{1-4}$ alkyl group, $C_{2-4}$ alkanyl group, $C_{2-4}$ alkynyl group or $C_{3-8}$ cycloalkyl group, wherein the groups represented by $Z^1$, $Z^3$ and R$^4$ may be substituted with 1 or 2 substituents selected from the group consisting of a $C_{1-4}$ alkyl group, $C_{2-4}$ alkenyl group, $C_{2-4}$ alkynyl group, $C_{3-8}$ cycloalkyl group, halogen, hydroxyl group, oxo, $C_{1-4}$ alkoxy group, di-$C_{1-4}$ alkylamino group, halogeno-$C_{1-4}$ alkyl group, $C_{1-4}$ acyl group, hydroxy-$C_{1-4}$ alkyl group and $C_{1-4}$ alkoxy-$C_{1-4}$ alkyl group;

W stands for a group represented by

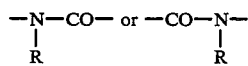

wherein R stands for (1) a hydrogen atom or (2) a $C_{1-4}$ alkyl, $C_{2-4}$ alkenyl or $C_{3-4}$ cycloalkyl which may be substituted by one to three substituents selected from the group consisting of a $C_{1-4}$ alkyl, 2-4 alkenyl, $C_{2-4}$ alkynyl, $C_{3-8}$ cycloalkyl, halogen, hydroxy, oxo, $C_{1-4}$ alkoxy, di-$C_{1-4}$ alkyl amino, halogeno-$C_{1-4}$ alkyl, $C_{1-4}$ acyl, hydroxy-$C_{1-4}$ alkyl and $C_{1-4}$ alkoxy-$C_{1-4}$ alkyl, or (3) may form a ring with R$^1$ when taken together with the adjacent

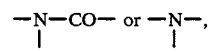

wherein the ring is selected from the group consisting of pyrrolyl, imidazolyl, pyrazolyl, piperidino, morpholino, dihydropyridyl, tetrahydropyridyl, N-methylpiperazinyl, N-ethylpiperazinyl, azacycloheptyl, azacyclooctyl, isoindolyl, indolyl, 2-pyrrolidinon-1-yl, 2-piperazinon-1-yl, hexahydro-2-azepinon-1-yl, octahydro-2-azocinon-1-yl, 2-oxoindolin-1-yl, 1-oxoisoindolin-2-yl, 2-oxo-1,2,3,4-tetrahydroquinolin-1-yl, 1-oxo-1,2,3,4-tetrahydroisoquinolin-2-yl, 1-oxo-5H-benzo-1,2,3,4-tetrahydro-2-azepin-2-yl, 1-oxobenzo-1,2,3,4,5,6-hexahydro-2-azocin-2-yl, 2-oxo-5H-benzo-1,2,3,4-tetrahydro-1-azepin-1-yl, 2-oxobenzo-1,2,3,4,5,6-hexahydro-1-azocin-1-yl, succinimide, glutarimide, 1,4-butanedicarboximide, 1,5-pentanedicarboximide, 1,2-cyclohexanedicarboximide, and phthalimide which may be substituted by one or two substituents selected from the group consisting of $C_{1-4}$ alkyl, 2-4 alkenyl, $C_{2-4}$ alkynyl, $C_{3-8}$ cycloalkyl, halogen, hydroxy, oxo, $C_{1-4}$ alkoxy, di-$C_{1-4}$ alkyl amino, halogeno-$C_{1-4}$ alkyl, $C_{1-4}$ acyl, hydroxy-$C_{1-4}$ alkyl and $C_{1-4}$ alkoxy-$C_{1-4}$ alkyl and which may be cyclized with a benzene, naphthalene, thiophene, furan, pyrrol, imidazole, pyrazole, thiazole, isothiazole, thiadiazole, oxazole, isoxazole, oxadiazole, furazane, pyran, pyridine, pyrazine, pyrimidine, pyridazine or their partially reduced or completely reduced forms, dioxolan, dioxane, piperidine, morpholine, N-methylpiperazine or N-ethylpiperazine; R$^1$ stands for (1) a $C_{1-4}$ alkyl, $C_{2-4}$ alkenyl or $C_{3-4}$ cycloalkyl, (2) a 5- or 6-membered cyclic hydrocarbon group selected from the group consisting of cyclopentadienyl, cyclopentenyl, cyclopentyl, cyclohexyl, cyclohexenyl, cyclohexanedienyl, phenyl, and their partially and completely reduced forms, or a 5- or 6-membered heterocyclic group selected from the group consisting of thienyl, furyl, pyrrolyl, thiazolyl, imidazolyl, thiadiazolyl, tetrazolyl, pyridyl, pyranyl, pyrazinyl, pyrimidinyl, pyridazinyl and their partially and completely reduced forms, or a condensed cyclic group selected from the group consisting of naphthyl, indenyl, benzothiazolyl, benzooxazolyl, quinolyl, isoquinolyl, quinazolyl and their partially and completely reduced forms which may be substituted by one or two substituents selected from the group consisting of a $C_{1-4}$ alkyl, $C_{2-4}$ alkenyl, $C_{2-4}$ alkynyl, $C_{3-6}$ cycloalkyl, $C_{5-6}$ cycloalkenyl, $C_{7-8}$ aralkyl, phenyl, 5- or 6-membered heterocyclic ring, $C_{1-4}$ alkoxy, phenoxy, $C_{1-4}$ alkanoyl group, benzoyl, $C_{1-4}$ alkanoyloxy group, benzoyloxy, carboxyl, $C_{1-4}$ alkoxy-carbonyl, $C_{1-4}$ alkoxy-carbonyl-$C_{1-4}$ alkyl, carboxyl-$C_{1-4}$ alkyl, carbamoyl, N-$C_{1-4}$ alkyl carbamoyl, 1-aziridinylcarbonyl, 1-azetidinylcarbonyl, 1-pyrrolidinylcarbonyl, 1-piperidinylcarbonyl, N-methylpiperazinylcarbonyl, morpholinocarbonyl, N,N-dimethylcarbamoyl, N,N-diethylcarbamoyl, N,N-dipropylcarbamoyl and N,N-dibutylcarbamoyl, halogen atom, mono-, di- or tri-halogeno-$C_{1-4}$ alkyl group oxo, amidino group, imino group, amino group, mono-$C_{1-4}$ alkylamino, di-$C_{1-4}$ alkylamino, aziridinyl, azetidinyl, pyrrolidinyl, pyrrolynyl, pyrrolyl, imidazolyl, pyrazolyl, imidazolidinyl, piperidino, morpholino, dihydropyridyl, pyridyl, N-methylpiperazinyl, N-ethylpiperazinyl, $C_{1-4}$ alkanoylamido, benzamido group, carbamoylamino group, N-$C_{1-4}$ alkyl carbamoylamino, 1-aziridinylcarbonylamino, 1-azetidinylcarbonylamino, 1-pyrrolidinylcarbonylamino, 1-piperidinylcarbonylamino, N-methylpiperazinyl-carbonylamino, morpholinocarbonylamino, N,N-dimethylcarbamoylamino, N,N-diethylcarbamoylamino, N,N-dipropylcarbamoylamino, N,N-dibutylcarbamoylamino, $C_{1-3}$ alkylene dioxy, —B-(OH)$_2$, hydroxyl, epoxy (—O—), nitro, cyano, mercapto, sulfo, sulfino, phosphono, dihydroxyboryl, sulfamoyl, $C_{1-4}$ alkyl sulfamoyl, 1-pyrrolidinylsulfonyl, 1-piperidinylsulfonyl, N-methyl-1-piperazinylsulfonyl and morpholinosulfonyl, di-$C_{1-4}$ alkyl sulfamoyl, $C_{1-4}$ alkylthio, phenylthio, $C_{1-4}$ alkyl sulfinyl, phenylsulfinyl, $C_{1-4}$ alkyl sulfonyl and phenylsulfonyl, wherein the 5- or 6-membered heterocyclic ring may be substituted by one or two substituents selected from the group consisting of a $C_{1-4}$ alkyl group, $C_{1-4}$ alkoxy group, halogen atom, hydroxyl group, carboxyl group, sulfo group, phosphono group, amidino group, amino group, methylamino group, ethylamino group, dimethylamino group, diethylamino group, morpholino group, piperidyl group, N-methylpiperazyl group, pyridyl group, trimethylammonium group, triethylammonium group, pyridinium group, tetrazolyl group and carboxylmethyl group; COOR$^2$ stands for an optionally esterified carboxyl group; and p denotes an integer of 1 to 4, provided that when —W—R$^1$ denotes a moiety represented by the formula:

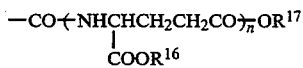

wherein COOR$^{16}$ and COOR$^{17}$ are, independently, an optionally esterified carboxyl group and n denotes an integer of 1 to 5, p denotes, 1, 3 or 4, or its salt.

2. A compound as claimed in claim 1, wherein the ring A is substituted at nitrogen atom with a $C_{1-4}$ alkyl group, $C_{2-4}$ alkenyl group, $C_{2-4}$ alkynyl, $C_{3-6}$ cycloalkyl group, $C_{1-4}$ alkanoyl group, benzoyl group, a benzoyl group substituted with 1 to 3 substituents selected from a halogen atom and a $C_{1-4}$ alkoxy group, hydroxy-$C_{1-4}$ alkyl group, $C_{1-4}$ alkoxy-$C_{1-4}$ alkyl, phenyl group, phenyl group substituted with 1 to 3 substituents selected from a halogen atom and a $C_{1-4}$ alkoxy group, benzyl group or benzyl group substituted with 1 to 3 substituents selected from a halogen atom, $C_{1-4}$ alkoxy and phenyl group.

3. A compound as claimed in claim 1, wherein the ring A is substituted at carbon atom thereof with 1 or 2 substituents selected from the group consisting of a $C_{1-4}$ alkyl group, a $C_{2-4}$ alkenyl group, $C_{2-4}$ alkynyl group, $C_{3-8}$ cycloalkyl group, halogen atom, $C_{1-4}$ alkanoyl group, benzoyl group, benzoyl group substituted with 1 to 3 substituents selected from a halogen atom and a $C_{1-4}$ alkoxy group, cyano group, carboxyl group, carbamoyl group, nitro group, hydroxyl group, hydroxy-$C_{1-4}$ alkyl group, $C_{1-4}$ alkoxy-$C_{1-4}$ alkyl group, $C_{1-4}$ alkoxy group, mercapto group, $C_{1-4}$ alkylthio group, amino group, amino group substituted with one or two $C_{1-4}$ alkyl groups and $C_{1-4}$ alkanoyl amino group.

4. A compound as claimed in claim 1, wherein the ring A stands for a pyrrole.

5. A compound as claimed in claim 1, wherein B$^0$ stands for a phenyl-1,4-ylene, thiophen-2,5-ylene thiazol-2,5-ylene or pyridin-2,5-ylene which may be substituted with 1 or 2 substituents selected from the group consisting of a $C_{1-4}$ alkyl group, $C_{2-4}$ alkenyl group, $C_{2-4}$ alkynyl group, $C_{3-8}$ cycloalkyl group, halogen atom, hydroxyl group, $C_{1-4}$ alkoxy group, di-$C_{1-4}$ alkylamino group, halogeno-$C_{1-4}$ alkyl group, oxo, $C_{1-4}$ acyl group, $C_{1-4}$ alkoxy-$C_{1-4}$ alkyl group.

6. A compound as claimed in claim 1, wherein B$^0$ stands for a phenyl-1,4-ylene.

7. A compound as claimed in claim 1, wherein X stands for an amino group or hydroxy group.

8. A compound as claimed in claim 1, wherein X stands for an amino group.

9. A compound as claimed in claim 1, wherein Y stands for hydrogen atom, a $C_{1-4}$ alkyl group, an amino group or hydroxyl group.

10. A compound as claimed in claim 1, wherein Y stands for an amino group.

11. A compound as claimed in claim 1, wherein Z stands for a $C_{1-5}$ alkylene group.

12. A compound as claimed in claim 1, wherein Z stands for ethylene.

13. A compound as claimed in claim 1, wherein Z stands for trimethylene.

14. A compound as claimed in claim 1, wherein Z is —NR$^4$—.

15. A compound as claimed in claim 1, wherein Z stands for a group of the formula: —Z$^{1'}$—NR$^{4'}$— wherein R$^{4'}$ stands for hydrogen atom, a $C_{1-4}$ alkyl group which may be substituted by a $C_{1-4}$ alkoxy-carbonyl group, formyl group and a $C_{1-4}$ alkoxycarbonyl group and Z$^{1'}$ stands for a $C_{1-4}$ alkyl group.

16. A compound as claimed in claim 1, wherein Z stands for a group of the formula: —(CH$_2$)$_2$—NH—, —(CH$_2$)$_2$—N(CH$_3$)— or —(CH$_2$)—N(Boc)—.

17. A compound as claimed in claim 1, wherein w stands for a group: —NHCO—.

18. A compound as claimed in claim 1, wherein w stands for a group: —CONH—.

19. A compound as claimed in claim 25, wherein the ring which formed by R with R$^1$, taken together with adjacent —N—CO— or —N— stands for a group:

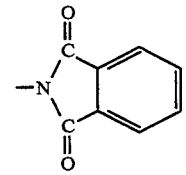

which may be substituted by one to three substituents selected from the group consisting of a $C_{1-4}$ alkyl, $C_{2-4}$ alkenyl, $C_{2-4}$ alkynyl, $C_{3-8}$ cycloalkyl, halogen, hydroxy, oxo, $C_{1-4}$ alkoxy, di-$C_{1-4}$ alkyl amino, halogeno-$C_{1-4}$ alkyl, $C_{1-4}$ acyl, hydroxy-$C_{1-4}$ alkyl and $C_{1-4}$ alkoxy-$C_{1-4}$ alkyl.

20. A compound as claimed in claim 1, wherein R$^1$ stands for a $C_{1-4}$ alkyl, $C_{2-4}$ alkenyl, $C_{2-4}$ alkynyl, phenyl, cyclohexyl, naphthyl, thienyl, cyclopentyl or tetrazolyl which may be substituted by one or two substituents selected from the group consisting of a $C_{1-4}$ alkyl, $C_{2-4}$ alkenyl, $C_{2-4}$ alkynyl, $C_{3-6}$ cycloalkyl, $C_{5-6}$ cycloalkenyl, $C_{7-8}$ aralkyl, phenyl, 5- or 6-membered heterocyclic ring, $C_{1-4}$ alkoxy, phenoxy, $C_{1-4}$ alkanoyl group, benzoyl, $C_{1-4}$ alkanoyloxy group, benzoyloxy, carboxyl, $C_{1-4}$ alkoxy-carbonyl, $C_{1-4}$ alkoxy-carbonyl-$C_{1-4}$ alkyl, carboxyl-$1_{-4}$ alkyl, carbamoyl, N-$C_{1-4}$ alkyl carbamoyl, 1-aziridinylcarbonyl, 1-azetidinylcarbonyl, 1-pyrrolidinylcarbonyl, 1-piperidinylcarbonyl, N-methylpiperazinylcarbonyl, morpholinocarbonyl, N,N-dimethylcarbamoyl, N,N-diethylcarbamoyl, N,N- dipropylcarbamoyl and N,N-dibutylcarbamoyl, halogen atom, mono-, di- or tri-halogeno-$C_{1-4}$ alkyl group oxo, amidino group, imino group, amino group, mono-$C_{1-4}$ alkylamino, di-$C_{1-4}$ alkylamino, aziridinyl, azetidinyl, pyrrolidinyl, pyrrolynyl, pyrrolyl, imidazolyl, pyrazolyl, imidazolidinyl, piperidino, morpholino, dihydropyridyl, pyridyl, N-methylpiperazinyl, N-ethylpiperazinyl, $C_{1-4}$ alkanolyamido, benzamido group, carbamoylamino group, N-$C_{1-4}$ alkyl carbamoylamino, 1-aziridinylcarbonylamino, 1-azetidinylcarbonylamino, 1-pyrrolidinylcarbonylamino, 1-piperidinylcarbonylamino, N-methylpiperazinylcarbonylamino, morpholinocarbonylamino, N,N-dimethylcarbamoylamino, N,N-diethylcarbamoylamino, N,N-dipropylcarbamoylamino, N,N-dibutycarbamoylamino, $C_{1-3}$ alkylene dioxy, —$B(OH)_2$-, hydroxyl, epoxy (—O—), nitro, cyano, mercapto, sulfo, sulfino, phosphono, dihydroxyboryl, sulfamoyl, $C_{1-4}$ alkyl sulfamoyl, 1-pyrrolidinylsulfonyl, 1-piperidinylsulfonyl, N-methyl-1-piperazinylsulfonyl and morpholinosulfonyl, di-$C_{1-4}$ alkyl sulfamoyl, $C_{1-4}$ alkylthio, phenylthio, $C_{1-4}$ alkyl sulfinyl, phenylsulfinyl, $C_{1-4}$ alkyl sulfonyl and phenylsulfonyl, wherein the 5- or 6-membered heterocyclic ring which may be substituted by one or two substituents selected from the group consisting of a $C_{1-4}$ alkyl group, $C_{1-4}$ alkoxy group, halogen atom, hydroxyl group, carboxyl group, sulfo group, phosphono group, amidino group, amino group, methylamino group, ethylamino group, dimethylamino group, diethylamino group, morpholino group, piperidyl group, N-methylpiperazyl group, pyridyl group, trimethylammonium group, triethylammonium group, pyridinium group tetrazolyl group and carboxylmethyl group.

21. A compound as claimed in claim 1, wherein $R^1$ stands for a $C_{1-4}$ alkyl, $C_{2-4}$ alkenyl, $C_{2-4}$ alkynyl, phenyl, naphthyl or tetrazolyl which may be substituted by substituents selected from the group consisting of a hydroxy, carboxyl, —$B(OH)_2$, tetrazolyl, methylenedioxy, $C_{1-4}$ alkyl, $C_{1-4}$ alkoxy, $C_{1-4}$ alkoxy-carbonyl, carboxyl-$C_{1-4}$ alkyl, $C_{1-4}$ alkoxy-carbonyl-$C_{1-4}$ alkyl, $C_{1-4}$ alkanoylamide and 1-pyrrolidynylcarbonyl group.

22. A compound as claimed in claim 1, wherein $R^1$ stands for a $C_{1-4}$ alkyl, $C_{2-4}$ alkenyl or $C_{2-4}$ alkynyl, which may be substituted by substituents selected from the group consisting of a carboxyl and $C_{1-4}$ alkoxy-carbonyl group.

23. A compound as claimed in claim 1, wherein $R^1$ stands for a phenyl, naphthyl or tetrazolyl which may be substituted by substituents selected from the group consisting of a hydroxy, carboxyl, —$B(OH)_2$-, tetrazolyl, methylenedioxy, $C_{1-4}$ alkyl, $C_{1-4}$ alkoxy, $C_{1-4}$ alkoxy-carbonyl, carboxyl-$C_{1-4}$ alkyl, $C_{1-4}$ alkoxy-carbonyl-$C_{1-4}$ alkyl, $C_{1-4}$ alkanoylamide and 1-pyrrolidynylcarbonyl group.

24. A compound as claimed in claim 1, wherein $COOR^2$ stands for a carboxyl group which may be esterified with (1) a $C_{1-5}$ alkyl group, (2) a benzyl group which may be substituted by one to three substituents selected from the group consisting of nitro or a $C_{1-4}$ alkoxy group, or (3) a phenyl group which may be substituted by one to three substituents selected from the group consisting of nitro and a $C_{1-4}$ alkoxyl group.

25. A compound as claimed in claim 1, wherein $COOR^2$ stands for a carboxyl group which may be esterified with (1) a $C_{1-5}$ alkyl group, or (2) a benzyl group.

26. A compound as claimed in claim 1, wherein $COOR^2$ stands for COOH or $COOCH_3$.

27. A compound as claimed in claim 1, wherein p denotes an integer of 2 to 4.

28. A compound as claimed in claim 1, wherein p denotes 2 or 3.

29. A compound as claimed in claim 1, wherein X stands for an amino group, and Y stands for an amino group.

30. A compound as claimed in claim 1, wherein X stands for an amino group, Y stands for an amino group and ring A stands for a pyrrole.

31. A compound as claimed in claim 1, wherein X stands for an amino group, Y stands for an amino group, ring A stands for a pyrrole and B stands for a phenyl-1,4-ylene.

32. A compound as claimed in claim 1, wherein $R^1$ stands for an optionally substituted cyclic group when p denotes 2 and W stands for a group: —CO—NH—.

33. A compound as claimed in claim 1 represented by the formula:

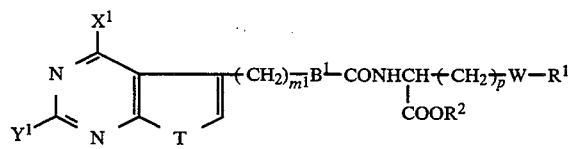

wherein T stands for a nitrogen atom; $B^1$ stands for $B^0$; $X^1$ stands for an amino group, hydroxyl group or mercapto group; $Y^1$ stands for Y; W is as defined in claim 1; $R^1$ is as defined in claim 1; $COOR^2$ stands for an optionally esterified carboxyl group; $m^1$ denotes an integer of 1 to 5; and p denotes an integer of 1 to 4, provided that when —W—$R^1$ denotes a moiety represented by the formula:

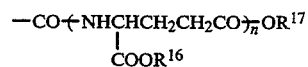

wherein $COOR^{16}$ and $COOR^{17}$ are, independently, an optionally esterified carboxyl group and n denotes an integer of 1 to 5, p denotes 1, 3 or 4, or its salt.

34. A compound as claimed in claim 1 represented by the formula:

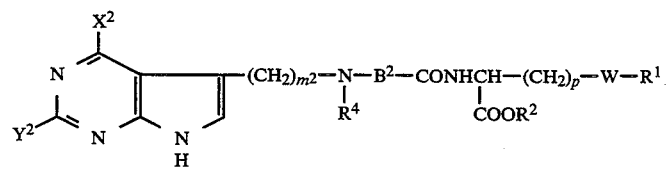

wherein B² stands for B⁰; X² stands for an amino group, hydroxyl group or mercapto group; Y² stands for Y; R⁴ stands for (1) a hydrogen atom, (2) a $C_{1-4}$ alkoxy-carbonyl group or (3) a $C_{1-4}$ alkyl group, $C_{2-4}$ alkenyl group, $C_{2-4}$ alkynyl group or $C_{3-8}$ cycloalkyl group which may be substituted by one or two substituents selected from the group consisting of a $C_{1-4}$ alkyl group, $C_{2-4}$ alkenyl group, $C_{2-4}$ alkynyl group, $C_{3-8}$ cycloalkyl group, halogen, hydroxyl group, oxo, $C_{1-4}$ alkoxy group, di-$C_{1-4}$ alkylamino group, halogeno-$C_{1-4}$ alkyl group, $C_{1-4}$ acyl group, hydroxy-$C_{1-4}$ alkyl group and $C_{1-4}$ alkoxy-$C_{1-4}$ alkyl group; W is as defined in claim 1; R¹ is as defined in claim 1; COOR² stands for an optionally esterified carboxyl group; m² denotes an integer of 1 to 4; and p denotes an integer of 1 to 4, provided that when —W—R¹ denotes a moiety represented by the formula:

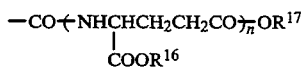

wherein COOR¹⁶ and COOR¹⁷ are, independently, an optionally esterified carboxyl group and n denotes an integer of 1 to 5, p denotes, 1, 3 or 4, or its salt.

35. A compound as claimed in claim 1, which is a compound of the formula:

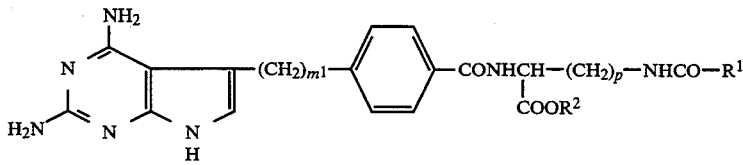

wherein m¹ denotes an integer of 1 to 5; the other symbols are as defined in claim 1, or its salt.

36. A compound as claimed in claim 35, wherein R¹ stands for a phenyl group which may be substituted.

37. A compound as claimed in claim 35, wherein R¹ stands for a phenyl group which may be substituted by a carboxyl-$C_{1-4}$ alkyl group.

38. A compound as claimed in claim 35, wherein R¹ stands for a naphthyl group which may be substituted.

39. A compound as claimed in claim 35, wherein R¹ stands for a naphthyl group which may be substituted by a carboxyl-$C_{1-4}$ alkyl group.

40. A compound as claimed in claim 35, wherein COOR² stands for a carboxyl group which may be substituted by a $C_{1-4}$ alkyl group.

41. A compound as claimed in claim 35, wherein p denotes an integer of 2 to 4.

42. A compound as claimed in claim 35, wherein R¹ stands for a tetrazolyl group which may be substituted.

43. N(α)-[4-[2-(2,4-diamino-7H-pyrrolo[2,3-d]pyrimidin-5-yl)ethyl]benzoyl]-N(δ)-hemiphthaloyl-L-ornithine or its salt.

44. N(α)-[4-[2-(2,4-diamino-7H-pyrrolo[2,3-d]pyrimidin-5-yl)ethyl]benzoyl]-N-(3-carboxyphenyl)-L-glutamine or its salt.

45. N(α)-[4-[2-(2,4-diamino-7H-pyrrolo[2,3-d]pyrimidin-5-yl)ethyl]benzoyl]-N(δ)-(3-carboxy-2-naphthoyl)-L-ornithine or its salt.

46. N(α)-[4-[2-(2,4-diamino-7H-pyrrolo[2,3-d]pyrimidin-5-yl)ethyl]benzoyl]-N-(1H-tetrazol-5-yl)-L-glutamine or its salt.

47. N(α)-[4-[2-(2,4-diamino-7H-pyrrolo[2,3-d]pyrimidin-5-yl)ethyl]benzoyl]-N(δ)-hemiphthaloyl-L-ornithine.

48. N(α)-[4-[2-(2,4-diamino-7H-pyrrolo[2,3-d]pyrimidin-5-yl)ethyl]benzoyl]-N-(3-carboxyphenyl)-L-glutamine.

49. Disodium N(α)-[4-[2-(2,4-diamino-7H-pyrrolo[2,3-d]pyrimidin-5-yl)ethyl]benzoyl]-N-(3-carboxyphenyl)-L-glutaminate.

50. N(α)-[4-[2-(2,4-diamino-7H-pyrrolo[2,3-d]pyrimidin-5-yl)ethyl]benzoyl]-N(δ)-(3-carboxy-2-naphthoyl)-L-ornithine.

51. N(α)-[4-[2-(2,4-diamino-7H-pyrrolo[2,3-d]pyrimidin-5-yl)ethyl]benzoyl]-N-(1H-tetrazol-5-yl)-L-glutamine.

52. An anti-tumor composition which comprises a pharmaceutically effective amount of a compound or its salt as claimed in claim 1.

53. An anti-tumor composition which comprises an effective amount of a compound as claimed in claim 1 or a pharmaceutically acceptable salt thereof, together with a pharmaceutically acceptable carrier or carriers.

54. A method for treating or preventing tumor which comprises administrating an effective amount of a compound as claimed in claim 1 or its pharmaceutically acceptable salt together with a pharmaceutically acceptable carrier or diluent to mammal.

55. A method of inhibiting cell proliferation comprising administering to a mammal in need thereof an effective amount of a compound of claim 1 or a pharmaceutically acceptable salt thereof in combination with a pharmaceutically acceptable carrier or diluent.

56. The method as claimed in claim 55, wherein the cell proliferation is human lung cancer cell proliferation.

* * * * *